(12) United States Patent
Barton et al.

(10) Patent No.: US 6,649,350 B2
(45) Date of Patent: *Nov. 18, 2003

(54) ELECTROCHEMICAL SENSOR USING INTERCALATIVE, REDOX-ACTIVE MOIETIES

(75) Inventors: Jacqueline K. Barton, San Marino, CA (US); Elizabeth M. Boon, Pasadena, CA (US); Shana O. Kelley, Pasadena, CA (US); Michael G. Hill, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/953,242

(22) Filed: Sep. 13, 2001

(65) Prior Publication Data

US 2002/0146716 A1 Oct. 10, 2002

Related U.S. Application Data

(63) Continuation-in-part of application No. 09/753,362, filed on Dec. 29, 2000, now Pat. No. 6,461,820, which is a continuation of application No. 09/056,995, filed on Apr. 8, 1998, now Pat. No. 6,221,586.
(60) Provisional application No. 60/043,146, filed on Apr. 9, 1997.

(51) Int. Cl.[7] .......................... C12Q 1/68; C12N 15/11

(52) U.S. Cl. ........................................ 435/6; 536/24.3

(58) Field of Search ............................... 435/6; 536/24.3

(56) References Cited

U.S. PATENT DOCUMENTS

| | | |
|---|---|---|
| 5,001,051 A | 3/1991 | Miller et al. |
| 5,312,527 A | 5/1994 | Mikkelsen et al. |
| 5,543,326 A | 8/1996 | Heller et al. |
| 5,705,348 A | 1/1998 | Meade et al. |
| 6,063,573 A | 5/2000 | Kayyem |
| 6,071,699 A | 6/2000 | Meade et al. |
| 6,087,100 A | 7/2000 | Meade et al. |
| 6,090,933 A | 7/2000 | Kayyem et al. |
| 6,096,273 A | 8/2000 | Kayyem et al. |

FOREIGN PATENT DOCUMENTS

| | | |
|---|---|---|
| WO | WO 95/15971 | 6/1995 |

OTHER PUBLICATIONS

Hashimoto, Koji, et al., "Sequence–Specific Gene Detection with a Gold Electrode Modified with DNA Probes and an Electrochemically Active Dye," *Anal. Chem.* 1994, 66, 3830–3833.

Maeda, Mizuo, et al., "DNA–Immobilized Gold Electrode for DNA–Binding Drug Sensor," Analytical Science, Feb. 1992, vol. 8, pp. 83–84.

Arkin, M.R., Stemp, E.D.A., Barton, J.K., "Long–Range Oxidation of Guanine by Ru(III) in Duplex DNA," (1997) Chem. and Biol., vol. 4, pp. 389–400.

Beratan, D.N., Priyadarshy, S., and Risser S.M., "DNA: Insulator or Wire?," (1997) Chem. and Biol., vol. 4, pp. 3–8.

Brun A.M. and Harriman A., "Dynamics of Electron Transfer between Intercalated Polycyclic Molecules: Effect of Interspersed Bases," (1992) J. Am. Chem. Soc. vol. 114, pp. 3656–3660.

Carter, M. T. et al., "Voltammetric Studies of the Interaction of Metal Chelates with DNA. 2. Tris–Chelated Complexes of Cobalt (III) and Iron (III) with 1,10–Phenanthroline and 2,2'–Bipyridine," (1989) J. Am. Chem. Soc., vol. 111, pp. 8901–8911.

Carter, M. T. and Bard, A. B., "Electrochemical Investigations of the Interaction of Metal Chelates with DNA. 3. Electrogenerated Chemiluminescent Investigation of the Interaction of Tris(1,10–phenanthroline)ruthenium(II) with DNA," (1999) Bioconj. Chem., vol. 1, pp. 257–263.

Drmanac, R., Drmanac, S., Strezoska, Z., Paunesku, T., Labat, I., Zeremski, M., Snoddy, J., Funkhouser, W. K., Koop, B., Hood, L. and Crkvenjakov, R., "DNA Sequence Determination by Hybridization: A Strategy for Efficient Large–Scale Sequencing", (1993) Science, vol. 260, pp. 1649–1652.

Hashimoto, Koji, et al., "*Novel DNA sensor for electrochemical gene detection*" (1994) *Analytica Chimica Acta*, 286:219–224.

Johnston, Dean H., et al., "*Electrochemical Measurement of the Solvent Accessibility of Nucleobases Using Electron Transfer between DNA and Metal Complexes*" (1995) *J. Am. Chem. Soc.* 117:8933–8938.

Chemical Abstracts, vol. 120, No. 11, Mar. 14, 1994, Abstract No. 126263c, Hashimoto, koji, et al., "*DNA sensor: a novel electrochemical gene detection method using carbon electrode immobilized DNA probes*", p. 246, col. 2.

Chemical Abstracts, vol. 127, No. 2, Jul. 14, 1997, Abstract No. 13828s, Wang, Joseph, et al., "*Detection of point mutation in the p53 gene using a peptide nucleic acid biosensor*", p. 135, col. 1.

(List continued on next page.)

*Primary Examiner*—John S. Brusca
(74) *Attorney, Agent, or Firm*—Gray Cary Ware & Freidenrich, LLP; Lisa A. Haile; Kelly K. Reynolds

(57) ABSTRACT

Compositions and methods for electrochemical detection and localization of genetic point mutations, common DNA lesions and other base-stacking perturbations within oligonucleotide duplexes adsorbed onto electrodes and their use in biosensing technologies are described. An intercalative, redox-active moiety (such as an intercalator or nucleic acid-binding protein) is adhered and/or crosslinked to immobilized DNA duplexes at different separations from an electrode and probed electrochemically in the presence or absence of a non-intercalative, redox-active moiety. Interruptions in DNA-mediated electron-transfer caused by base-stacking perturbations, such as mutations or binding of a protein to its recognition site are reflected in a difference in electrical current, charge and/or potential.

69 Claims, 18 Drawing Sheets

OTHER PUBLICATIONS

Elghanian, R., Storhoff, J.J., Mucic, R.C., Letsinger, R.L., and Mirkin, C.A., "Selective Colorimetric Detection of Polynucleotides Based on the Distance–Dependent Optical Properties of Gold Nanoparticles," (1997) Science, vol. 277, pp. 1078–1081.

Fukui, K. and Tanaka, K., "Distance Dependence of Photoinduced Electron Transfer in DNA," (1998) Angew. Chem. Int. Ed. Engl., vol. 37, pp. 158–161.

Hall, D.B., Homlin, R.E., and Barton, J.K., "Oxidative DNA Damage Through Long–Range Electron Transfer," (1996) Nature vol. 382, pp. 731–735.

Hall D.B. and Barton, J.K., "Sensitivity of DNA–Mediated Electron Transfer of the Intervening P–Stack: A Probe for the Integrity of the DNA Base Stack," (1997) J. Am. Chem. Soc., vol. 119, pp. 5045–5046.

Hashimoto, K. et al., "Novel DNA Sensor for Electrochemical Gene Detection," (1994) Anal. Chim. Acta, vol. 286, pp. 219–224.

Herne, T. and Tarlov, M.J., "Characterization of DNA Probes Immobilized on Gold Surfaces," (1997) J. Am. Chem. Soc., vol. 119, pp. 8916–8920.

Homlin, R.E., Dandliker, P.J., and Barton, J.K., "Charge Transfer through the DNA Base Stack," (1997) Angew. Chem. Int. Ed. Engl., vol. 36, pp. 2714–2730.

Jackson, B. A. and Barton, J. K., "Recognition of DNA Base Mismatches by a Rhodium Intercalator," (1997) J. Am. Chem. Soc., vol. 119, pp. 12986–12987.

Johnston, D. H., Glasgow, K. C. and Thorp, H. H., "Electrochemical Measurement of the Solvent Accessibility of Nucleobases Using Electron Transfer between DNA and Metal Complexes" (1995) J. Am. Chem. Soc., vol. 117, pp. 8933–8938.

Kelley, S.O., Barton, J.K., Jackson, N.M., Hill, M.G., "Electrochemistry of Methylene Blue Bound to a DNA–Modified Electrode," (1997) Bioconj. Chem., vol. 8, pp. 31–37.

Kelley, S.O., Homlin, R.E., Stemp, E.D.A., and Barton, J.K., "Photoinduced Electron Transfer in Ethidium–Modified DNA Duplexes: Dependence on Distance and Base Stacking", (1997) J. Am. Chem. Soc., vol. 119, pp. 9861–9870.

Lamture, J. B. et al., "Direct Detection of Nucleic Acid Hybridization on the Surface of a Charge Coupled Device", (1994) Nucl. Acids Res., vol. 22, pp. 2121–2125.

Lewis, F.D., Wu, T., Zhang, Y., Letsinger, R.L., Greenfield, S.R., and Wasielewski M.R., "Distance–Dependent Electron Transfer in DNA Hairpins," (1997) Science, vol. 277, pp. 673–676.

Lipshutz, R. J., Morris, D., Chee, M., Hubbell, E., Kozal, M. J., Shah, N., Shen, N., Yang, R., and Fodor, S. P., "Using Oligonucleotide Probe Arrays to Access Genetic Diversity," (1995) Biotechniques, vol. 19, pp. 442–447.

Maeda, M. et al., "$Mg^{2+}$–Selective Electrode Comprising Double–Helical DNA as Receptive Entity," (1994) Chem. Lett., pp. 1805–1808.

Meade, T. J. and Kayyem, J.F., "Electron Transfer through DNA: Site–Specific Modification of Duplex DNA with Ruthenium Donors and Acceptors," (1995) Angew. Chem. Int. Ed. Engl., vol. 34, pp. 352–354.

Murphy, C.J., Arkin; M.A., Ghatlia, N.D., Bossman, S., Turro, N.J., and Barton, J.K., "Fast Photoinduced Electron Transfer through DNA Intercalation," (1994) Proc. Natl. Acad. Sci. USA, vol. 91, pp. 5315–5319.

Murphy, C.J., Arkin; M.A., Jenkins, Y., Ghatlia, N.D., Bossman, S., Turro, N.J., and Barton, J.K., "Long–Range Photoinduced Electron Transfer through a DNA Helix," (1993) Science, vol. 262, pp. 1025–1029.

Netzel T.L., "Electron Transfer Reactions in DNA," (1997) Chem. Educ., vol. 74, pp. 646–651.

Purugganan, M. D. et al, "Accelerated Electron Transfer between Metal Complexes Mediated by DNA," (1988) Science, vol. 241, pp. 1645–1649.

Rodriguez, M., and Bard, A. J., "Electrochemical Studies of the Interaction of Metal Chelates with DNA. 4. Voltammetric and Electrogenerated Chemiluminescent Studies of the Interaction of Tris(2,2'–bipyridine)osmium(II) with DNA," (1990) Anal. Chem., vol. 62, 2658–2662.

Warmann, J.M., de Haas, M.P., and Rupprecht, A., "DNA: A Molecular Wire?," (1996) Chem. Phys. Lett., vol. 249, pp. 319–322.

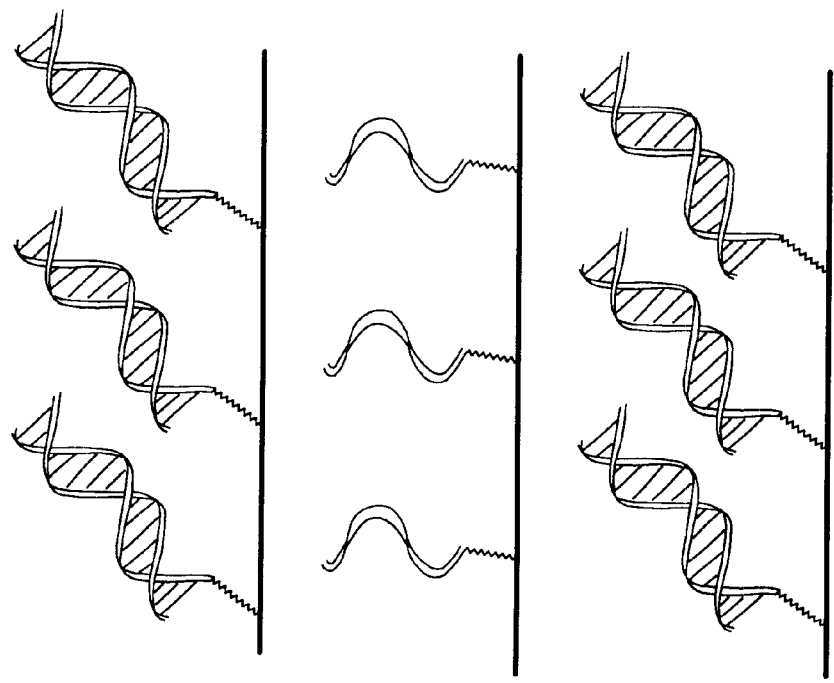
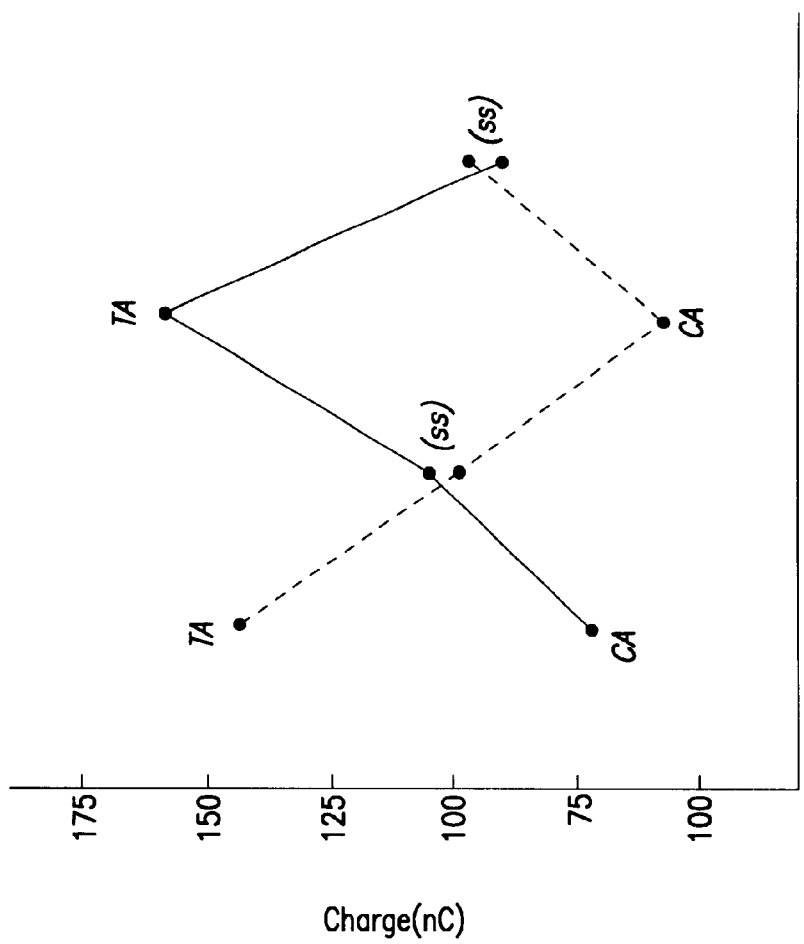
FIG. 6

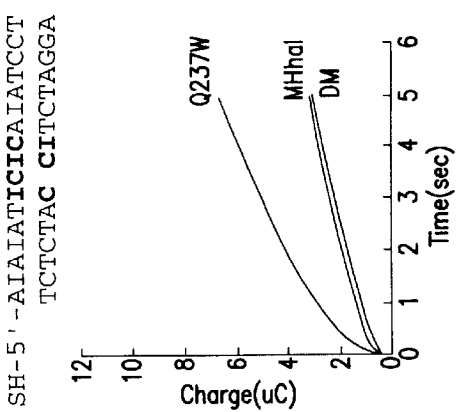
FIG. 18A
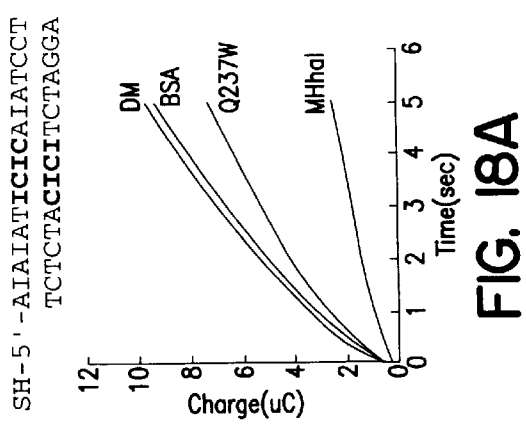
FIG. 18B
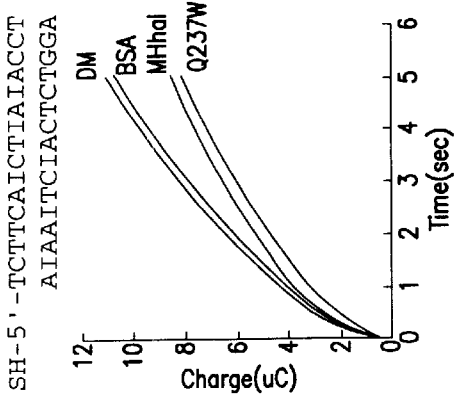
FIG. 18C
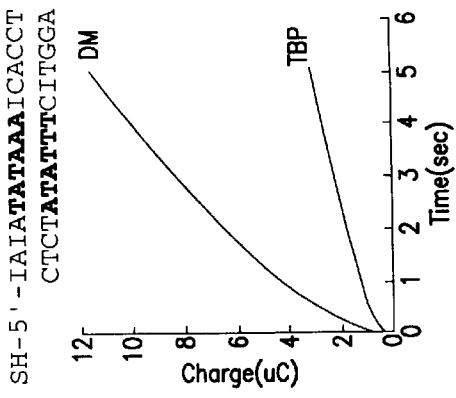
FIG. 18D
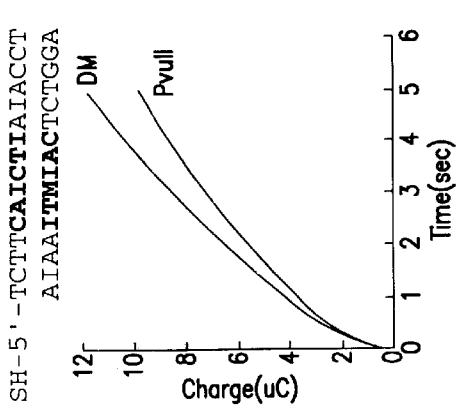
FIG. 18E
FIG. 18F

ELECTROCHEMICAL SENSOR USING INTERCALATIVE, REDOX-ACTIVE MOIETIES

RELATED APPLICATIONS

This application is a continuation-in-part of Ser. No. 09/753,362, filed Dec. 29, 2000, U.S. Pat. No. 6,461,820 which is a continuation of Ser. No. 09/056,995, filed Apr. 8, 1998, now issued U.S. Pat. No. 6,221,586, which claims priority under §119(e) to U.S. Provisional application Serial No. 60/043,146, filed Apr. 9, 1997, the contents of which are hereby incorporated by reference in their entirety.

GOVERNMENT RIGHTS

The U.S. Government may have certain rights in this invention pursuant to Grant No. GM 49216 awarded by the National Instituted of Health.

FIELD OF THE INVENTION

The present invention relates to the detection and localization of base-pair mismatches and other perturbations in base-stacking within an oligonucleotide duplex.

DESCRIPTION OF RELATED ART

It is now well known that mutations in DNA can lead to severe consequences in metabolic functions (e.g., regulation of gene expression, modulation of protein production) which ultimately are expressed in a variety of diseases. For example, a significant number of human cancers are characterized by a single base mutation in one of the three ras genes (Bos, 1989). In order to unravel the genetic components of such diseases, it is of utmost importance to develop DNA sensors that are capable of detecting single-base mismatches rapidly and efficiently and to establish routine screening of disease-related genetic mutations based on such sensors (Skogerboe, 1993; Southern, 1996; Chee, 1996; Eng, 1997).

Various methods that have been developed for the detection of differences between DNA sequences rely on hybridization events to differentiate native versus mutated sequences and are limited by the small differences in base-pairing energies caused by point mutations within extended polynucleotides (Millan, 1993; Hashimoto, 1994; Xu, 1995; Wang, 1996; Lockhart, 1996; Alivisatos, 1996; Korriyoussoufi, 1997; Elghanian, 1997; Lin, 1997; Herne, 1997). Typically, a nucleic acid hybridization assay to determine the presence of a particular nucleotide sequence (i.e. the "target sequence") in either RNA or DNA comprises a multitude of steps. First, an oligonucleotide probe having a nucleotide sequence complementary to at least a portion of the target sequence is labeled with a readily detectable atom or group. When the labeled probe is exposed to a test sample suspected of containing the target nucleotide sequence, under hybridizing conditions, the target will hybridize with the probe. The presence of the target sequence in the sample can be determined qualitatively or quantitatively in a variety of ways, usually by separating the hybridized and non-hybridized probe, and then determining the amount of labeled probe which is hybridized, either by determining the presence of label in probe hybrids or by determining the quantity of label in the non-hybridized probes. Suitable labels may provide signals detectable by luminescence, radioactivity, colorimetry, x-ray diffraction or absorption, magnetism or enzymatic activity, and may include, for example, fluorophores, chromophores, radioactive isotopes, enzymes, and ligands having specific binding partners. However, the specific labeling method chosen depends on a multitude of factors, such as ease of attachment of the label, its sensitivity and stability over time, rapid and easy detection and quantification, as well as cost and safety issues. Thus, despite the abundance of labeling techniques, the usefulness, versatility and diagnostic value of a particular system for detecting a material of interest is often limited.

Some of the currently used methods of mismatch detection include single-strand conformation polymorphism (SSCP) (Thigpen, 1992; Orita, 1989), denaturing gradient gel electrophoresis (DGGE) (Finke, 1996; Wartell, 1990; Sheffield, 1989), RNase protection assays (Peltonen and Pulkkinen, 1986; Osborne, 1991), allele-specific oligonucleotides (Wu, 1989), allele-specific PCR (Finke, 1996), and the use of proteins which recognize nucleotide mismatches, such as the E. coli mutS protein (Modrich, 1991).

In the first three methods, the appearance of a new electrophoretic band is observed by polyacrylamide gel electrophoresis. SSCP detects the differences in speed of migration of single-stranded DNA sequences in polyacrylamide gel electrophoresis under different conditions such as changes in pH, temperature, etc. A variation in the nucleotide base sequence of single-standed DNA segments (due to mutation or polymorphism) may lead to a difference in spatial arrangement and thus in mobility. DGGE exploits differences in the stability of DNA segments in the presence or absence of a mutation. Introduction of a mutation into double-stranded sequences creates a mismatch at the mutated site that destabilizes the DNA duplex. Using a gel with an increasing gradient of formamide (denaturation gradient gel), the mutant and wild-type DNA can be differentiated by their altered migration distances. The basis for the RNase protection assay is that the RNase A enzyme cleaves mRNA that is not fully hybridized with its complementary strand, whereas a completely hybridized duplex is protected from RNase A digestion. The presence of a mismatch results in incomplete hybridization and thus cleavage by RNase A at the mutation site. Formation of these smaller fragments upon cleavage can be detected by polyacrylamide gel electrophoresis. Techniques based on mismatch detection are generally being used to detect point mutations in a gene or its mRNA product. While these techniques are less sensitive than sequencing, they are simpler to perform on a large number of tumor samples. In addition to the RNase A protection assay, there are other DNA probes that can be used to detect mismatches, through enzymatic or chemical cleavage. See, e.g., Smooker and Cotton, 1993; Cotton, 1988; Shenk, 1975. Other enzymatic methods include for example the use of DNA ligase which covalently joins two adjacent oligonucleotides which are hybridized on a complementary target nucleic acid, see, for example Landegren (1988). The mismatch must occur at the site of ligation.

Alternatively, mismatches can also be detected by shifts in the electrophoretic mobility of mismatched duplexes relative to matched duplexes (Cariello, 1988). With either riboprobes or DNA probes, the cellular mRNA or DNA which may contain a mutation can be amplified using polymerase chain reaction (PCR) prior to hybridization. Changes in DNA of the gene itself can also be detected using Southern hybridization, especially if the changes are gross rearrangements, such as deletions and insertions.

DNA sequences of the specified gene which have been amplified by use of PCR may also be screened using allele-specific oligonucleotide probes. These probes are nucleic acid oligomers, each of which is complementary to a corresponding segment of the investigated gene and may or may not contain a known mutation. The assay is performed by detecting the presence or absence of a hybridization signal for the specific sequence. In the case of allele-specific PCR, the PCR technique uses unique primers which selectively hybridize at their 3'-ends to a particular mutated sequence. If the particular mutation is not present, no amplification product is observed.

In addition, restriction fragment length polymorphism (RFLP) probes for the gene or surrounding marker genes can be used to score alteration of an allele or an insertion in a polymorphic fragment. However, since the recognition site of restriction endonucleases ranges in general between 4 to 10 base pairs, only a small portion of the genome is monitored by any one enzyme.

Another means for identifying base substitution is direct sequencing of a nucleic acid fragment. The traditional methods are based on preparing a mixture of randomly-termiated, differentially labeled DNA fragments by degradation at specific nucleotides, or by dideoxy chain termination of replicating strands (Maxam & Gilbert, 1980; Sanger, 1977). Resulting DNA fragments in the range of 1 to 500 basepairs are then separated on a gel to produce a ladder of bands wherein the adjacent samples differ in length by one nucleotide. The other method for sequencing nucleic acids is sequencing by hybridization (SBH, Drmanac, 1993). Using mismatch discriminative hybridization of short n-nucleotide oligomers (n-mers), lists of constitutent n-mers may be determined for target DNA. The DNA sequence for the target DNA may be assembled by uniquely overlapping scored oligonucleotides. Yet another approach relies on hybridization to high-density arrays of oligonucleotides to determine genetic variation. Using a two-color labeling scheme simultaneous comparison of a polymorphic target to a reference DNA or RNA can be achieved (Lipshutz, 1995; Chee, 1996; Hacia, 1996).

Each of these known prior art methods for detecting base pair mismatches has limitations that affect adequate sensitivity, specificity and ease of automation of the assay. In particular, these methods are unable to detect mismatches independent of sequence composition and require carefully controlled conditions, and most methods detect multiple mismatches only. Additional shortcomings that limit these methods include high background signal, poor enzyme specificity, and/or contamination.

Over the last decade, attention has also focused on DNA as a medium of charge transfer in photoinduced electron transfer reactions and its role in mutagenesis and carcinogenesis. For example, studies were performed using various octahedral metal complexes (which bind tightly to DNA by intercalation) as donors and acceptors for photoinduced electron transfer. Dppz complexes of ruthenium, osmium, cobalt, nickel, and rhenium showed tight intercalative binding and unique photophysical and electrochemical properties. No photoluminesence was observed upon irradiation of the metal complexes in aqueous solution in absence of DNA (as a result of quenching by proton transfer from the solvent), whereas in the presence of DNA excitation of the complex afforded significant, long-wavelength emission (because now the intercalated complex was protected from quenching). Studies using rhodium intercalators containing phenanthrenequinone-diimine (phi) ligands displayed tight DNA binding by preferential intercalation, some with affinities and specifities approaching DNA-binding proteins.

Photoinduced electron transfer using DNA as a molecular bridge has been established in various systems. Using metal complexes intercalated into the base stack of DNA as donor and acceptor it has been proposed that the DNA π-stack could promote electron transfer at long range. Additionally, the products of redox-triggered reactions of DNA bases have been detected at sites remote from intercalating oxidants (Hall, 1996; Dandliker, 1997; Hall, 1997; Arkin, 1997). For example, it has been shown that a metallointercalator can promote oxidative DNA damage through long-range hole migration from a remote site. Oligomeric DNA duplexes were prepared with a rhodium intercalator covalently attached to one end and separated spatially from 5'-GG-3' doublet sites of oxidation. Rhodium-induced photooxidation occurred specifically at the 5'-G in the 5'-GG-3' doublets and was observed up to 37 Å away from the site of rhodium intercalation. In addition it was found that rhodium intercalators excited with 400 nm light, initiated the repair of a thymine dimer incorporated site-specifically in the center of a synthetic 16-mer oligonucleotide duplex. The repair mechanism was thought to proceed via oxidation of the dimer by the intraligand excited state of the rhodium complex, in which an electron deficiency (hole) is localized on the intercalated phi ligand. Like electron transfer between metallointercalators, the efficiencies of long-range oxidative processes were found to be remarkably sensitive to the coupling of the reactants into the base stack (Holmlin, 1997) and depended upon the integrity of the base stack itself (Kelley, 1997c, 1997d; Hall, 1997; Arkin, 1997) as well as on the oxidation potential. Perturbations caused by mismatches or bulges greatly diminished the yields of DNA-mediated charge transport.

Other studies have reported electron transfer through DNA using nonintercalating ruthenium complexes coordinated directly to amino-modified sugars at the terminal position of oligonucleotides (Meade, 1995). In this system it was suggested that electron transfer is protein-like. In proteins, where the energetic differences in coupling depend upon σ-bonded interactions, small energetic differences between systems do not cause large differences in electronic coupling. In the DNA double helix however, π-stacking can contribute to electronic coupling such that small energetic differences could lead to large differences in coupling efficiency. Most recently, Lewis and coworkers measured rates of photo-oxidation of a guanine base in a DNA hairpin by an associated stilbene bound at the top of the hairpin (Lewis, 1997). By systematically varying the position of the guanine base within the hairpin and measuring the rate of electron transfer, a value for β, the electronic coupling parameter, could be made. Here, β was found to be intermediate between that seen in proteins, with σ bonded arrays, and that found for a highly coupled π-bonded array.

Electrochemical studies of small molecule/DNA complexes have focused primarily on solution-phase phenomena, in which DNA-induced changes in redox potentials and/or diffusion constants of organic and inorganic species have been analyzed to yield association constants (Carter, 1989, 1990; Rodriguez, 1990; Welch, 1995; Kelly, 1986; Molinier-Jumel, 1978; Berg, 1981; Plambeck, 1984). In addition, rates of guanine oxidation catalyzed by electrochemically oxidized transition-metal complexes have been used to evaluate the solvent accessibility of bases for the detection of mismatches in solution (Johnston, 1995). Electrochemical signals triggered by the association of small molecules with DNA have also been applied in the design of other novel biosensors. Toward this end, oligonucleotides have been immobilized on electrode surfaces by a variety of linkages for use in hybridization assays. These include thiols on gold (Hashimoto, 1994a, 1994b; Okahata, 1992), carbodiimide coupling of guanine residues on glassy carbon (Millan, 1993), and alkane bisphosphonate films on $Al^{3+}$-treated gold (Xu, 1994, 1995). Both direct changes in mass (measured at a quartz crystal microbalance) (Okahata, 1992) and changes in current (Hashimoto, 1994a, 1994b; Millan, 1993) or electrogenerated chemiluminesence (Xu, 1994, 1995) due to duplex-binding molecules have been used as reporters for double stranded DNA. Gold surfaces modified with thiolated polynucleoti des have also been used for the detection of metal ions and DNA-binding drugs (Maeda, 1992, 1994).

Other known electrochemical sensors used in an increasing number of clinical, environmental, agricultural and biotechnological applications include enzyme based biosensors. Amperometric enzyme electrodes typically require some form of electrical communication between the electrode and the active site of the redox enzyme that is reduced or oxidized by the substrate. In one type of enzyme electrode, a non-natural redox couple mediates electron transfer from the substrate-reduced enzyme to the electrode. In this scheme, the enzyme is reduced by its natural substrate at a given rate; the reduced enzyme is in turn, rapidly oxidized by a non-natural oxidizing component of a redox couple that diffuses into the enzyme, is reduced, diffuses out and eventually diffuses to an electrode where it is oxidized.

Electrons from a substrate-reduced enzyme will be transferred either to the enzyme's natural re-oxidizer or, via the redox-centers of the polymer to the electrode. Only the latter process contributes to the current. Thus, it is desirable to make the latter process fast relative to the first. This can be accomplished by (a) increasing the concentration of the redox centers, or (b) assuring that these centers are fast, i.e. that they are rapidly oxidized and reduced.

Most natural enzymes are not directly oxidized at electrodes but require a mediator either bound to the electrode or in solution. It has, however, been shown that enzymes can be chemically modified by binding to their proteins redox couples, whereupon, if in the reduced state, they transfer electrons to an electrode. It has also been shown that when redox polycations in solution electrostatically complex polyanionic enzymes, electrons will flow in these complexes from the substrate to the enzyme, and from the enzyme through the redox polymer, to an electrode. In addition, systems have been developed where a redox-active polymer, such as poly(vinyl-pyridine), has been introduced which electrically connects the enzyme to the electrode. In this case, the polycationic redox polymer forms electrostatic complexes with the polyanionic glucose oxidase in a manner mimicking the natural attraction of some redox proteins for enzymes, e.g., cytochrome c for cytochrome c oxidase.

The present invention provides a new approach for the detection of mismatches and common DNA lesions by DNA-mediated charge transport. This electrochemical method is based on DNA-mediated electron transfer using intercalative, redox-active species and detects differences in electrical current or charge generated with fully base-paired duplexes versus duplexes containing a base-stacking perturbation, such as a mismatch. Carried out at an addressable multielectrode array, this method allows the processing of multiple sequences in the course of a single measurement, thus significantly improving the efficiency of screening for multiple genetic defects, including detection of only a small number of mutated DNA samples within a large pool of wild-type sequences and detection of single-base lesions in RNA/DNA hybrids and duplex DNA. Most importantly, the assay reports directly on the structural difference in base pair stacking within the hybridized duplex, rather than on a thermodynamic difference based on the condition-dependent hybridization event itself. Consequently, mismatch detection becomes independent of the sequence composition and sensors based on this approach offer fundamental advantages in scope, sensitivity and accuracy over any other existing methods.

SUMMARY OF THE INVENTION

The present invention provides a highly sensitive and accurate method for the detection of genetic point mutations and common DNA lesions in nucleic acid sequences and its application as a biosensor by DNA-mediated charge transport. The invention also provides an electrochemical assay of protein binding to DNA-modified electrodes based upon the detection of associated perturbations in DNA base stacking using DNA charge transport. In a particular embodiment, the invention relates to electrodes that are prepared by modifying their surfaces with oligonucleotide duplexes combined with an intercalative, redox-active species and their use as sensors based on an electrochemical process in which electrons are transferred between the electrode and the redox-active species. In another embodiment, the invention also relates to detection of base-pair mismatches, base flipping, or other base-stacking perturbations due to protein-nucleic acid interactions. Additionally, the protein-DNA interaction allows a method of electrical monitoring of DNA enzymatic reactions in a duplex nucleic acid sequence.

One aspect of the invention relates to methods for determining the presence of point mutations sequentially in a series of oligonucleotide duplexes using an intercalative, redox-active moiety. A preferred method includes: (a) contacting at least one strand of a first nucleic acid molecule with a strand of a second nucleic acid molecule under hybridizing conditions, wherein one of the nucleic acid molecules is derivatized with a fanctionalized linker, (b) depositing this duplex onto an electrode or an addressable multielectrode array, (c) contacting the adsorbed duplex which potentially contains a base-pair mismatch with an intercalative, redox-active moiety under conditions suitable to allow complex formation, (d) measuring the amount of electrical current or charge generated as an indication of the presence of a base-pair mismatch within the adsorbed duplex, (e) treating the complex under denaturing conditions in order to separate the complex, yielding a monolayer of single-stranded oligonucleotides, and (f) rehybridizing the single-stranded oligonucleotides with another target sequence. Steps (c) through (f) can then be repeated for a sequential analysis of various oligonucleotide probes. Attenuated signals, as compared to the observed signals for fully base-paired, i.e. wild-type, sequences, will correspond to mutated sequences.

In some instances, it may be desirable to crosslink the intercalative, redox-active species to the duplex and perform the assay comprised of steps (a) through (d) only.

Another preferred method relates to the detection of point mutations utilizing electrocatalytic principles. More specifically, this method utilizes an electrode-bound double-stranded DNA monolayer which is immersed in a solution comprising an intercalative, redox-active species, which binds to the monolayer, and a non-intercalative redox-active species which remains in solution. This method includes: (a) contacting at least one strand of a first nucleic acid molecule with a strand of a second nucleic acid molecule under hybridizing conditions, wherein one of the nucleic acid molecules is derivatized with a functionalized linker, (b) depositing this duplex which potentially contains a base-pair mismatch onto an electrode or an addressable mnultielectrode array, (c) immersing this complex in an aqueous solution comprising an intercalative, redox-active moiety and a non-intercalative, redox-active moiety under conditions suitable to allow complex formation, (d) measuring the amount of electrical current or charge generated as an indication of the presence of a base-pair mismatch within the adsorbed duplex, (e) treating the complex under denaturing conditions in order to separate the complex, yielding a monolayer of single-stranded oligonucleotides, and (f) rehybridizing the single-stranded oligonucleotides with another target sequence. Steps (c) through (f) can then be repeated for a sequential analysis of various oligonucleotide probes. Utilizing this method, pronounced currents and thus increased signals will be observed due to the electrocatalytic reduction of the non-intercalative, redox-active moiety by the surface-bound, redox-active moiety.

In yet another embodiment, the invention provides an electrocatalytic assay that enables the detection of all possible single base mismatches, a small number of mutated DNA samples within a large pool of wild-type sequences, several naturally occurring base lesions and single base lesions in either DNA or RNA/DNA hybrids. Specifically, this method utilizes an electrode-bound double-stranded DNA monolayer which is immersed in a solution comprising an intercalative, redox-active species, which binds to the monolayer surface, and a non-intercalative redox-active species which remains in solution. This method includes, contacting a first single stranded nucleic acid probe sequence, which may be derivatized, with a second single stranded nucleic acid target sequence to form a duplex, wherein the second single stranded nucleic acid target sequence is hybridized to a monolayer of first single stranded nucleic acid probe sequences on an electrode; wherein the monolayer is prepared by first attaching a duplex comprising the first single stranded nucleic acid probe sequence to the electrode, dehydridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film; immersing the nucleic acid-modified film in a solution comprising an intercalative, redox-active moiety and a non-intercalative redox-active moiety; and measuring the electrical current or charges of the catalytic reduction of the non-intercalative, redox-active species by the intercalative, redox-active moiety wherein a difference of the electric current or charge from the electrical current or charge of a nucleic acid duplex not having one or more single-base sequence lesions is indicative of the presence or absence of one or more single-base sequence lesions in the target sequence. The last two steps can be repeated for a sequential analysis of various oligonucleotide probes. Utilizing this method, pronounced currents and thus increased signals will be observed due to the electrocatalytic reduction of the non-intercalative, redox-active moiety by the surface-bound, redox-active moiety.

In general, owing to their relatively high thermodynamic stability and their minor modification to the DNA duplex, these lesions have been very difficult to detect, with post-labeling procedures the preferred methods of analysis. These lesions do, however, appear to perturb electronic coupling within the DNA duplex. As a result, DNA mediated charge transport coupled to electrocatalysis is sensitive to those perturbations.

Yet another aspect of the invention relates to a method of detecting the presence or absence of a protein and includes: (a) contacting at least one strand of a first nucleic acid molecule with a strand of a second nucleic acid molecule under hybridizing conditions, wherein one of the nucleic acid molecules is derivatized with a functionalized linker and wherein the formed duplex is designed such to contain the recognition site of a nucleic acid-binding protein of choice, (b) depositing this duplex onto an electrode or an addressable multielectrode array, (c) contacting the adsorbed duplex with an intercalative, redox-active moiety under conditions suitable to allow complex formation, (d) potentially crosslinking the intercalative, redox-active moiety to the duplex, (e) immersing the complex in a first sample solution to be analyzed for the presence of the nucleic acid-binding protein, (f) measuring the amount of electrical current or charge generated as an indication of the presence or absence of the nucleic acid-binding protein in the sample solution, (g) treating the complex under appropriate conditions to remove the nucleic acid-binding protein, and (h) immersing it in a second sample solution to be analyzed for the presence of the nucleic acid-binding protein in order to separate the complex. Steps (e) through (h) can then be repeated for a sequential analysis of various sample solutions. Attenuated signals, as compared to signals measured for a reference solution without the nucleic acid-binding protein, indicate the presence of the nucleic acid-binding protein which is binding to its recognition site, thus causing a perturbation in base-stacking.

In another aspect, the invention relates to an electrochemical assay of protein binding to nucleic acid-modified electrodes, based on the detection of base flipping in the DNA base stacking using DNA charge transport and includes: a) at least one strand of a single stranded derivatized nucleic acid sequence containing a protein binding sequence and an electrochemical probe binding sequence is hybridized to a second single stranded nucleic acid sequence to form a duplex, wherein the second single stranded nucleic acid sequence is hybridized to a monolayer of first single stranded nucleic acid sequences on an electrode. The monolayer is prepared by first attaching a duplex comprising the first single stranded nucleic acid sequence to the electrode, and dehybridizing the duplex, such that the first single stranded nucleic acid sequence remains attached to the electrode, and wherein the hybrid of the first single stranded nucleic acid sequence and the second single stranded sequence form a double stranded nucleic acid-modified film; b) to this film is added an electrochemical probe, which binds to the electrochemical probe binding sequence of the first single stranded nucleic acid sequence; c) to the double stranded nucleic acid modified film is added a protein, which binds to the protein binding sequence of the first single stranded nucleic acid sequence; and d) the charges produced are measured and compared to the charges measured without the protein and a difference of the electrical current of charge from the electrical current or charge of a nucleic acid duplex not having a protein bound to the duplex DNA is indicative of the presence or absence of base flipping due to protein binding in the duplex.

Another aspect of the present invention relates to an electrochemical assay of protein binding to nucleic acid-modified electrodes based upon the detection of associated perturbations in the DNA base stacking, using DNA charge transport. The method includes: a) at least one strand of a single stranded derivatized nucleic acid sequence containing a protein binding sequence and an electrochemical probe binding sequence is hybridized to a second single stranded nucleic acid sequence to form a duplex, wherein the second single stranded nucleic acid sequence is hybridized to a monolayer of first single stranded nucleic acid sequences on an electrode. Wherein the monolayer is prepared by first attaching a duplex comprising the first single stranded nucleic acid sequence to the electrode, and dehybridizing the duplex, such that the first single stranded nucleic acid sequence-remains attached to the electrode, and wherein the hybrid of the first single stranded nucleic acid sequence and the second single stranded sequence form a double stranded nucleic acid-modified film; b) to this film is added an electrochemical probe, which binds to the electrochemical probe binding sequence of the first single stranded nucleic acid sequence; c) to the double stranded nucleic acid modified film is added a protein, which binds to the protein binding sequence of the first single stranded nucleic acid sequence; and d) the charges produced are measured and compared to the charges measured without the protein and a difference of the electrical current of charge from the electrical current or charge of a nucleic acid duplex not having a protein bound to the duplex DNA is indicative of the presence or absence of perturbations in the DNA base stacking due to protein binding in the duplex.

Yet another aspect of the invention relates to a method of electrochemical monitoring of DNA enzymatic reactions in a duplex nucleic acid sequence associated with protein binding to the duplex nucleic acid sequence, using DNA charge transport, and includes: a) at least one strand of a single stranded derivatized nucleic acid sequence containing a protein binding sequence and an electrochemical probe binding sequence is hybridized to a second single stranded nucleic acid sequence to form a duplex, wherein the second single stranded nucleic acid sequence is hybridized to a monolayer of first single stranded nucleic acid sequences on an electrode. Wherein the monolayer is prepared by first attaching a duplex comprising the first single stranded nucleic acid sequence to the electrode, and dehybridizing the duplex, such that the first single stranded nucleic acid sequence remains attached to the electrode, and wherein the hybrid of the first single stranded nucleic acid sequence and the second single stranded sequence form a double stranded nucleic acid-modified film; b) to this film is added an electrochemical probe, which binds to the electrochemical probe binding sequence of the first single stranded nucleic acid sequence; c) to the double stranded nucleic acid modified film is added a protein, which binds to the protein binding sequence of the first single stranded nucleic acid sequence; and d) the charges produced are measured and compared to the charges measured without the protein and a difference of the electrical current of charge from the electrical current or charge of a nucleic acid duplex not having a protein bound to the duplex DNA is indicative of the presence or absence of an enzymatic reaction of the duplex.

The invention also relates to the nature of the redox-active moieties. The requirements of a suitable intercalative, redox-active moiety include the position of its redox potential with respect to the window within which the oligonucleotide-surface linkage is stable, as well as the synthetic feasibility of covalent attachment to the oligonucleotide. In addition, chemical and physical characteristics of the redox-active intercalator may promote its intercalation in a site-specific or a non-specific manner. In a preferred embodiment, the redox-active species is in itself an intercalator or a larger entity, such as a nucleic acid-binding protein, that contains an intercalative moiety.

The nature of the non-intercalative, redox-active species for the electrocatalysis based assays depends primarily on the redox potential of the intercalative, redox-active species utilized in that assay.

Yet another aspect of the invention relates to the composition and length of the oligonucleotide probe and methods of generating them. In a preferred embodiment, the probe is comprised of two nucleic acid strands of equal length. In another preferred embodiment the two nucleic acid strands are of uneven length, generating a single-stranded overhang of desired sequence composition (i.e. a "sticky end"). The length of the oligonucleotide probes range preferably from 12 to 25 nucleotides, while the single-stranded overhangs are approximately 5 to 10 nucleotides in length. These single-stranded overhangs can be used to promote site-specific adsorption of other oligonucleotides with the complementary overhang or of enzymes with the matching recognition site.

The invention further relates to methods of creating a spatially addressable array of adsorbed duplexes. A preferred method includes (a) generating duplexes of variable sequence composition that are derivatized with a functionalized linker, (b) depositing these duplexes on different sites on the multielectrode array, (c) treating the complex under denaturing conditions to yield a monolayer of single-stranded oligonucleotides, and (d) hybridizing these single-stranded oliglonucleotides with a complementary target sequence. Another preferred method includes (a) depositing 5 to 10 base-pair long oligonucleotide duplexes that are derivatized on one end with a functionalized linker and contain single-stranded overhangs (approximately 5 to 10 nucleotides long) of known sequence composition at the opposite end onto a multielectrode array, and (b) contacting these electrode-bound duplexes under hybridizing conditions with single-stranded or double-stranded oligonucleotides that contain the complementary overhang.

Another aspect of the invention is directed towards the nature of the electrode, methods of depositing an oligonucleotide duplex (with or without a redox-active moiety adsorbed to it) onto an electrode, and the nature of the linkage connecting the oligonucleotide duplex to the electrode. In a preferred embodiment, the electrode is gold and the oligonucleotide is attached to the electrode by a sulfur linkage. In another preferred embodiment the electrode is carbon and the linkage is a more stable amide bond. In either case, the linker connecting the oligonucleotide to the electrode is preferably comprised of 5 to 20 covalent bonds.

Another aspect of the present invention relates to an electrochemical assay of protein binding to nucleic acid-modified electrodes based upon the detection of base flipping in the DNA base stacking, using DNA charge transport. This assay provides a method for probing protein-dependent changes in nucleic acid structure.

Another aspect of the present invention relates to an electrochemical assay of protein binding to nucleic acid-modified electrodes based upon the detection of associated perturbations in the DNA base stacking, using DNA charge transport. This assay provides a method for probing protein-dependent changes in nucleic acid structure.

Yet another aspect of the invention relates to a method of electrochemical monitoring of DNA enzymatic reactions in a duplex nucleic acid sequence associated with protein binding to the duplex nucleic acid sequence, using DNA charge transport. This assay provides a method for probing protein-dependent changes in nucleic acid structure.

Yet another aspect of the invention relates to various methods of detection of the electrical current or charge generated by the electrode-bound duplexes combined with an intercalative, redox-active species. In a preferred embodiment, the electrical current or charge is detected using electronic methods, for example voltammetry or amperommetry, or optical methods, for example fluorescence or phosphoresence. In another preferred embodiment, the potential at which the electrical current is generated is detected by chronocoulometry.

(SEQ ID NOS: 4–11)
5'CGCGATGACTGTACT (TA, $T_m$ = 68° C.),

5'CGCGACGACTGTACT (CA, $T_m$ = 56° C.),

5'CGCGATGTCTGTACT (TT, $T_m$ = 57° C.),

5'CGCGATCACTGTACT (CC, $T_m$ = 56° C.),

5'CGCGATGGCTGTACT (GT, $T_m$ = 62° C.),

5'CGCGATGAATGTACT (GA, $T_m$ = 60° C.),

5'CGCGATGCCTGTACT (CT, $T_m$ = 58° C.).

Figure 5:
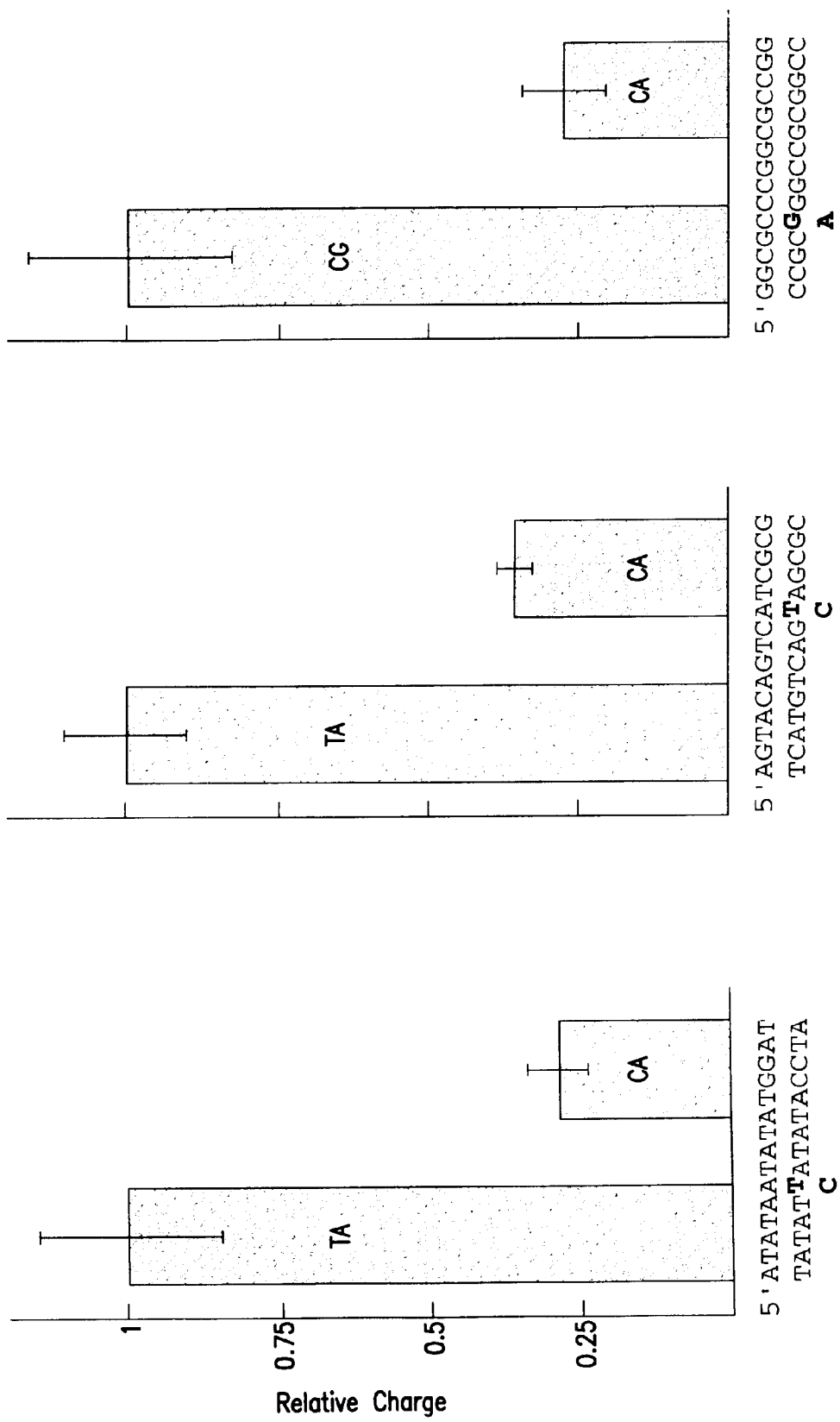

FIG. 5 describes the charge obtained for DNA-modified electrodes in the presence of 1.0 μM daunomycin the identified duplexes of varying percentages of GC content were either fully base-paired or contained a single CA mismatch. Mismatch detection measuring the electrical current or charge generated was independent of the sequence composition (SEQ ID NOS. 13–14).

FIG. 6 describes the charges ($Q_c$) measured during the in situ detection of a CA mismatch. Electrodes were derivatized with the sequence SH-5'AGTACAGTC$\underline{A}$TCGCG, where either a C or a T was incorporated into the complement across from the underlined A. Using cyclic voltarmmetry, the electrochemical response of daunomycin non-covalently bound to duplex-modified electrodes was measured first for the intact TA or CA duplexes (TA vs. CA), secondly (after denaturation of the duplex) for the single stranded oligonucleotide (ss), thirdly (after rehybridization with the opposite complement) again for the duplex (CA vs. TA), and lastly (after repeating the denaturation step) again for the single-stranded oligonucleotide (ss) (SEQ ID NO: 4).

Figure 7:
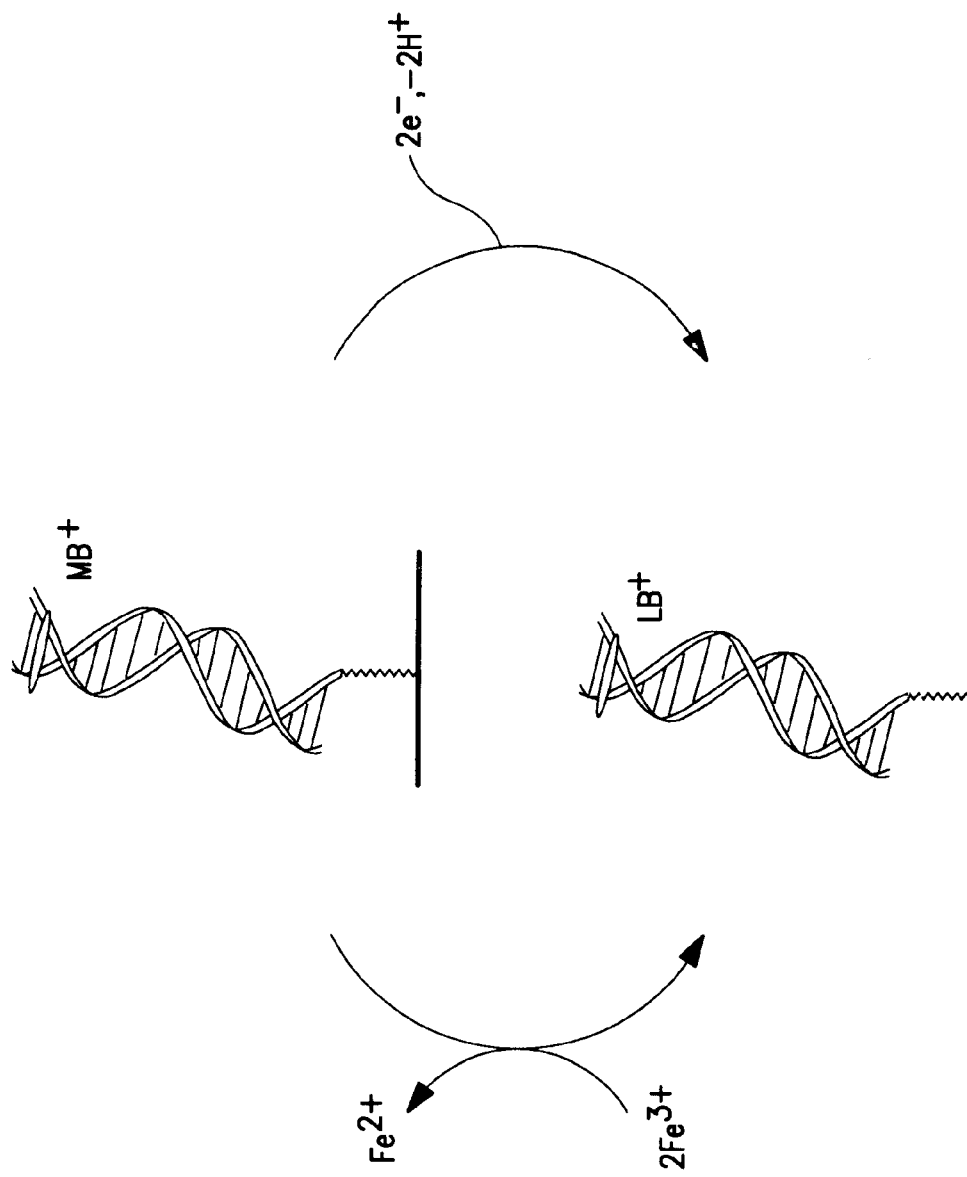

FIG. 7 represents a schematic illustration of electrocatalytic reduction of ferricyanide Methylene blue ($MB^+$) is reduced electrochemically through the DNA base stack to form leucomethylene blue ($LB^+$). Ferricyanide is then reduced by $LB^+$, causing the regeneration of $MB^+$ and the observation of catalytic currents.

Figure 8:
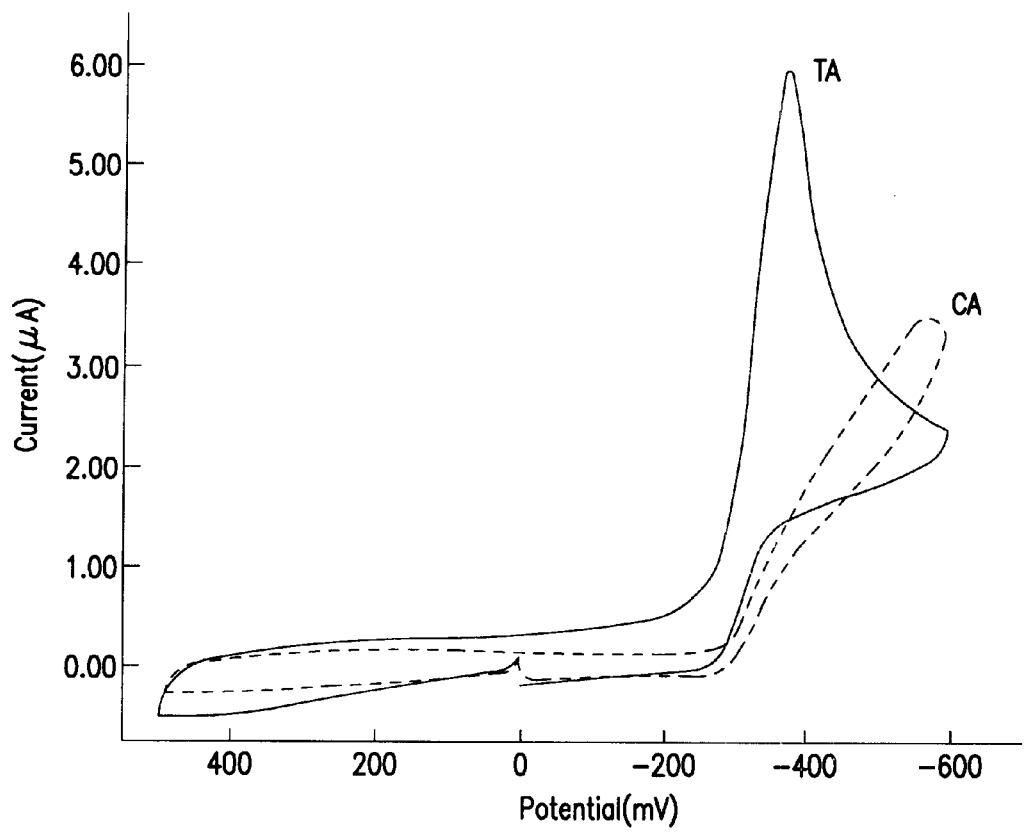

FIG. 8 illustrates cyclic voltammograms of gold electrodes modified with thiol-terminated duplexes containing TA and CA basepairs immersed in a solution containing 1.0 μM methylene blue and 1.0 mM ferricyanide. The oligonucleotide SH-5'AGTACAGTC$\underline{A}$TCGCG was hybridized with the corresponding complements containing either a T or a C opposite from the underlined A (SEQ ID NO: 4).

Figure 9:
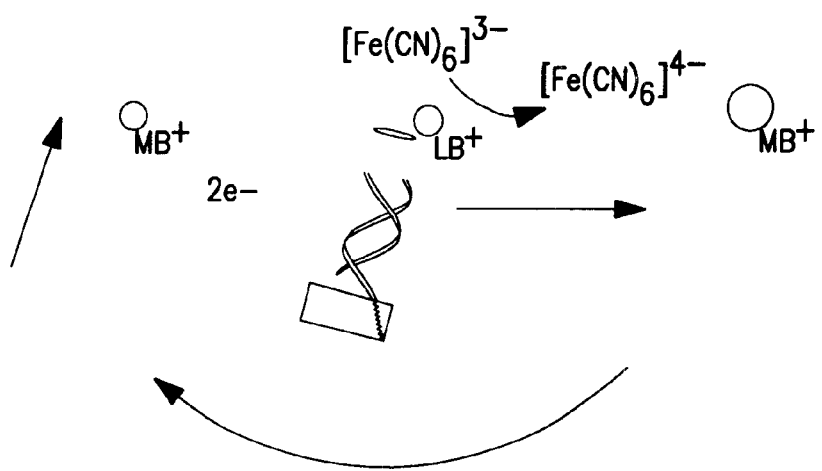

FIG. 9 illustrates the reduction of ferricyanide in the electrocatalytic process. Electrons flow from the electrode surface to intercalated $MB^+$ in a DNA-mediated reaction. The reduced form of $MB^+$, leucomethylene blue ($LB^+$), in turn, reduces solution-borne ferricyanide, so that more electrons can flow to $MB^+$ and the catalytic cycle continues.

Figure 10:
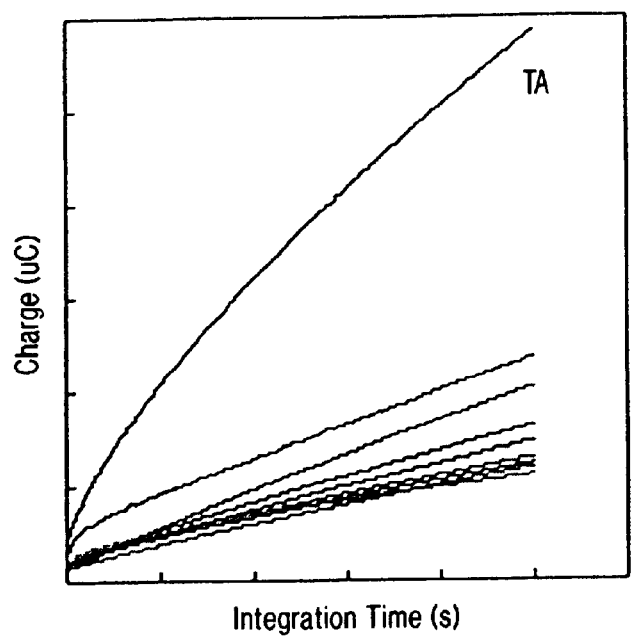

FIG. 10 illustrates the charge over time results of chronocoulometry at −350 mV of 2.0 mM Fe(CN)63-plus 0.5 mM MB+(pH 7) at a gold electrode modified with the thiol-terminated sequence SH-5'-AGTACAGTCATCGCG hybridized to a fully base paired complement (TA) and complements that introduce single base mismatches. From the top, the first line is the TA fully paired complement, the second and third lines are purine—purine mismatches, the fourth and fifth lines are purine-pyrimidine mismatches, the sixth line is a purine—purine mismatch, the seventh line is a purine-pyrimidine mismatch and the eighth and ninth lines are pyrimidine—pyrimidine mismatches. These experiments were carried out under completely hybridizing conditions at ambient temperatures in 5 mM sodium phosphate, 50 mM NaCl, pH 7.0. Mismatch detection is based on diminished DNA-mediated electron transfer efficiency due to the local base stack perturbation caused by a mismatch. The discrimination between Watson-Crick and mismatched sequences increases with sampling time (SEQ ID NO: 4).

Figure 11:
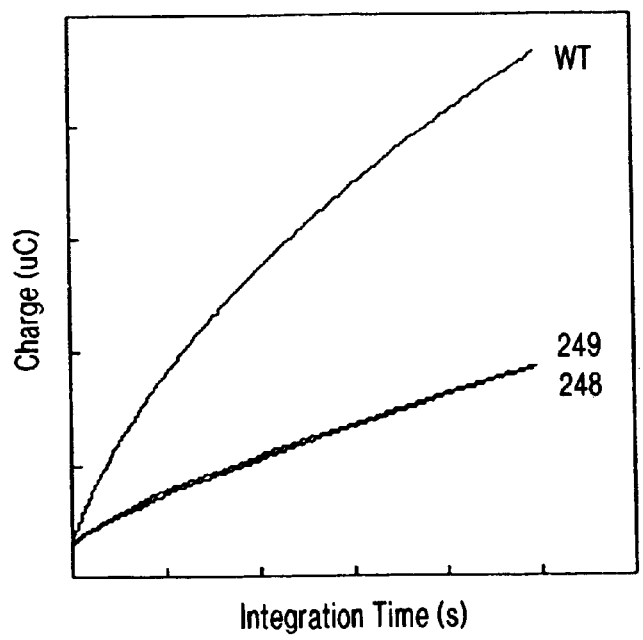

FIG. 11 illustrates the charge (uC) measured over time using electrocatalytic chronocoulometry at −350 mV with 0.5 M $MB^+$ and 2 mM $Fe(CN)_6^{3-}$ for the sequence SH-5'-ATGGG$\underline{C}$CTCCGGTTC with either a CA mismatch at the boldface C (the common 248 mutation), or a CT mismatch at the underlined $\underline{C}$ (the common 249 mutation), as distinguished from the charge over time for the native duplex (SEQ ID NO: 15).

Figure 12:
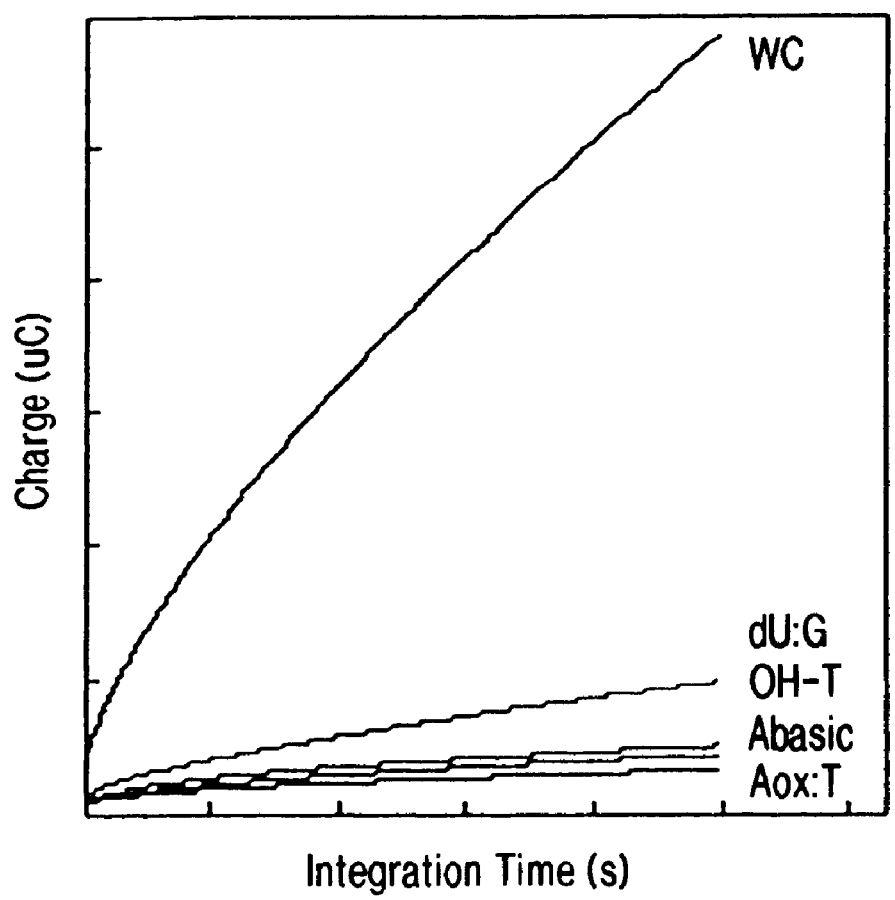

FIG. 12 illustrates the charge (uC) measured over time using electrocatalytic chronocoulometry at −350 mV with 0.5 M $MB^+$ and 2 mM $Fe(CN)_6^{3-}$ for various modifications of the sequence SH-5'AGTACAGTCATCGCG. The electrodes were modified in separate samples with double-stranded DNA sequences containing 8-oxo-adenine, 5,6-dihydro thymine, an abasic site, and deoxyuracil paired with guanine (the result of cytosine deamination). Each lesion was successfully detected within duplex DNA (SEQ ID NO: 4).

Figure 13:
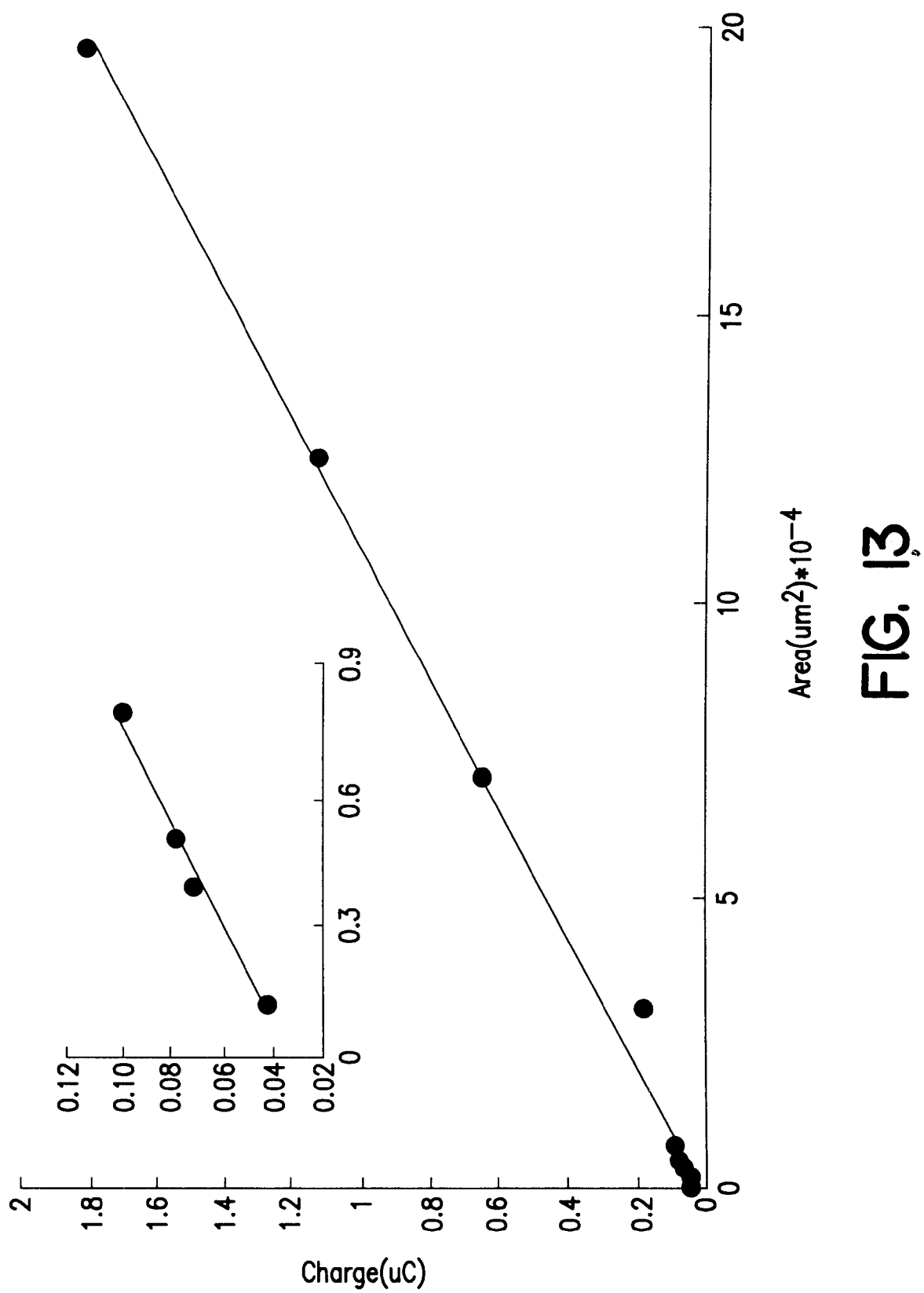

FIG. 13 illustrates the charge per area of the electrodes in a gold microarray after allowing the charge to accumulate during 5 seconds of electrocatalysis. The strictly proportional relationship between the total amount of charge accumulated and the electrode can be seen in the Figure.

Figure 14:
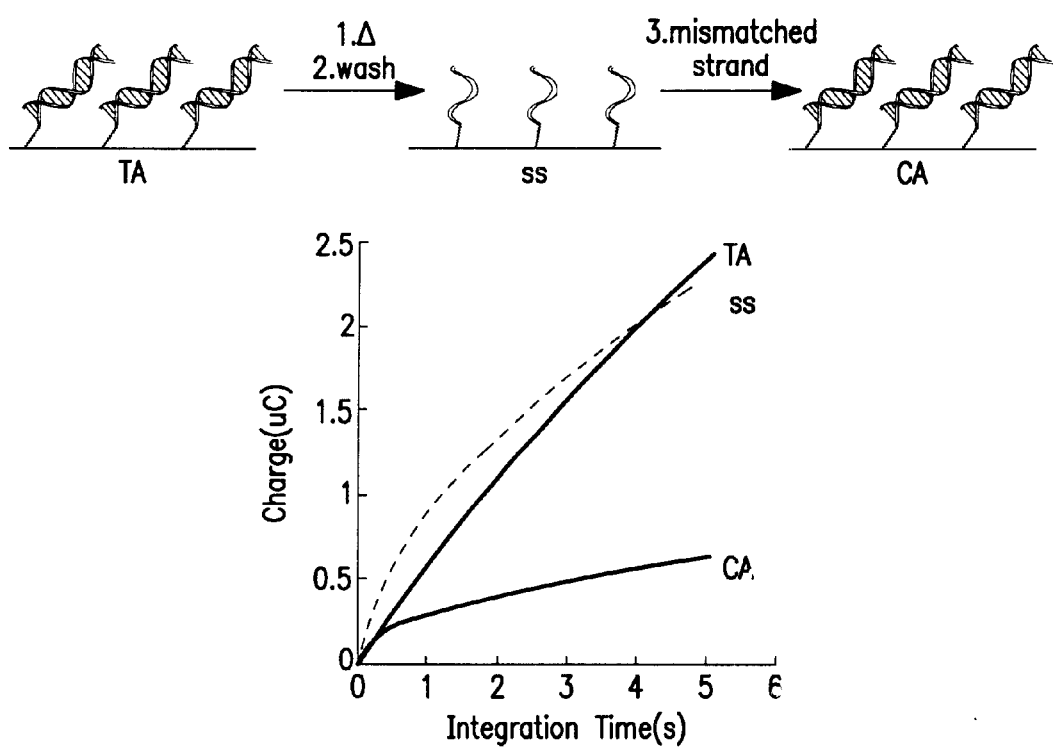

FIG. 14 illustrates the charge over time results of electrocatalysis of the monolayer on the electrode, the monolayer hybridized to the well-matched sequence SH-5'-

AGTACAGTCATCGCG-3' and the monolayer hybridized to a complement with a single CA mismatch (SEQ ID NO: 4).

Figure 15:
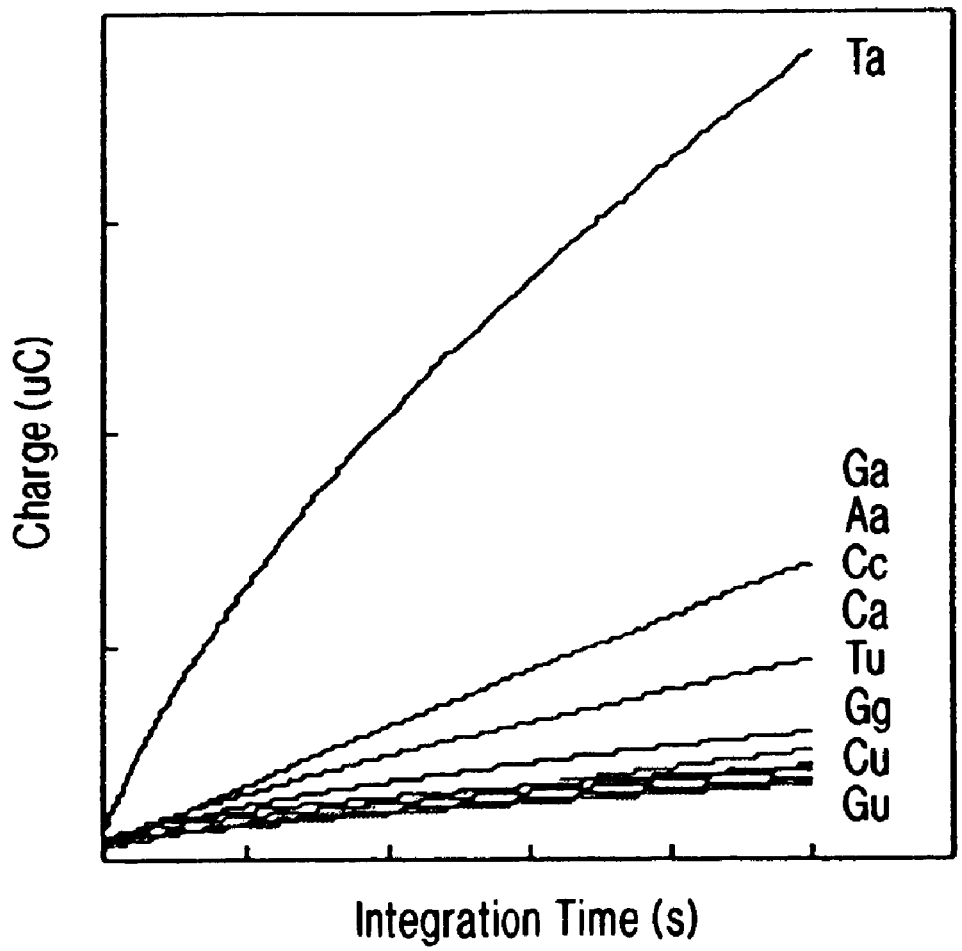

FIG. 15 illustrates the charge over time results of chronocoulometry at −350 mV of 2.0 mM Fe(CN)63-plus 0.5 mM MB+ (pH 7) at a gold electrode modified with the thiol-terminated sequence SH-5'-AGTACAGTCATCGCG hybridized to a fully base paired RNA complement (Ta) and other RNA complements that introduce single base mismatches. These experiments were carried out under completely hybridizing conditions at ambient temperatures in 5 mM sodium phosphate, 50 mM NaCl, pH 7.0. Mismatch detection is also achieved in these DNA/RNA hybrids (SEQ ID NO: 4).

Figure 16:
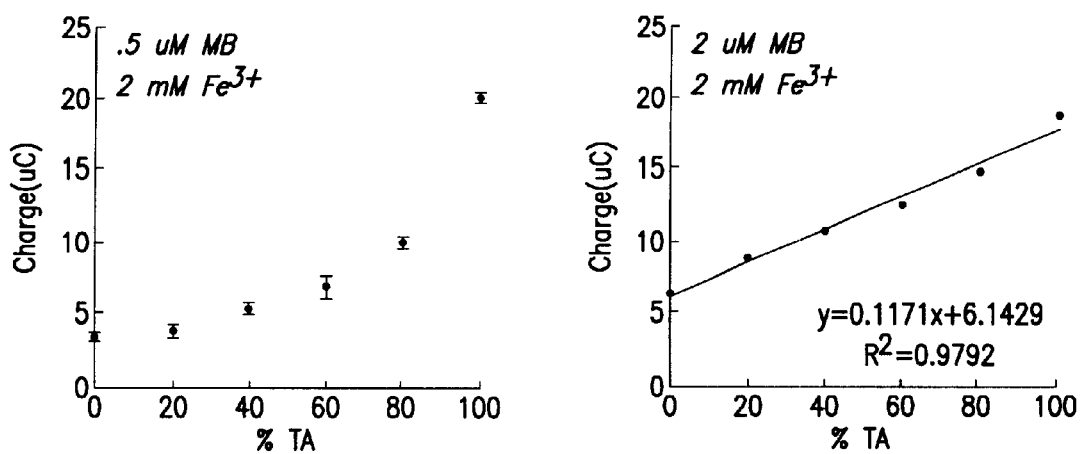

FIG. 16 illustrates a comparison of mismatch detection by electrocatalysis with varying catalyst concentrations. In lower MB+ concentrations, the electrocatalytic signal is shown to decrease rapidly in a non-linear fashion, as a function of the percent of CA duplexes in the film. In higher $MB^+$ concentrations, however, a linear response occurs.

Figure 17:
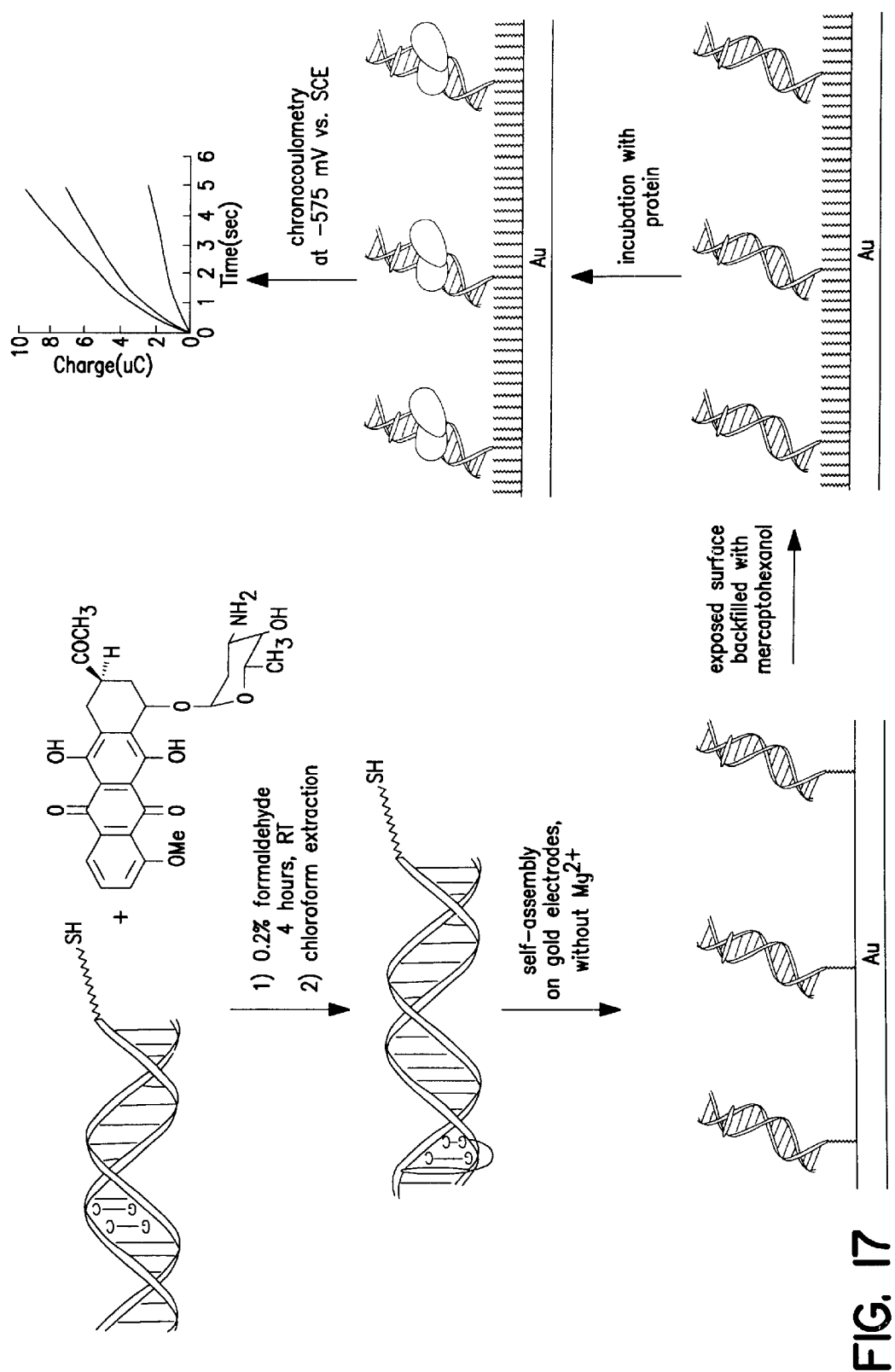

FIG. 17 illustrates the fabrication of DNA-modified gold electrodes for electrochemical analysis of protein binding and reaction. Once the gold electrode modification is complete, the electrode is incubated with approximately 1 $\mu$M of a test protein for 20 minutes and then interrogated by chronocoulometry at −575 mV vs. SCE. If the amount of charge accumulated after five seconds is significantly less than the control without protein, that particular protein disrupts the base stack of DNA upon binding.

FIG. 18 illustrates charge transport through DNA-modified surfaces, which accurately reflects DNA structure perturbation caused by protein binding. Chronocoulometry at −575 mV of DM covalently crosslinked to thiol-terminated DNA films (pH 7) on gold with and without bound protein. For the experiments illustrated in panels A-E, the DNA sequence used is above the graph with the DNA binding site underlined and the daunomycin binding site in italics. The control trace of that surface is indicated by "DM" (DM only, without protein). The test trace after incubation with protein is indicated by "M.HhaI," UDG," or "TBP" (demonstrating inhibition of DNA-mediated CT), "Q237W" or "PvuII" (demonstrating efficient CT), or "BSA" (a protein that does not bind DNA). Panels A and B contain the data obtained with M.HhaI; Panel A is using the well-matched binding site and panel B is using a binding site containing an abasic site, which facilitates base-flipping by the enzyme. Panel C contains the data obtained with UDG, another base-flipping enzyme. Panel D contains the results for electrochemical studies using TBP and panel E contains the data in the presence and absence of PvuII. Panel F is a control experiment where the DNA binding site (for PvuII) and protein (M.HhaI wildtype, Q237W) do not match or the protein used does not bind DNA at all (BSA). All of the proteins which are known from crystallographic measurements to kink the DNA result in an inhibition of the DM chronocoulometry (except in panel B, in which the DNA contains an abasic site, which itself is a base stack perturbation), while proteins that bind to DNA without disrupting the base stack do not result in significant inhibition. A small drop the in amount of charge accumulated is always observed upon protein binding. This small change in the electrical property of the film seems to be indicative of protein binding. For example, when BSA (which does not bind DNA) is used, the small drop in charge is not observed (panels A and F). However, when M.HhaI is used on a film without a binding site (panel F) but at a concentration where is should bind to DNA non-specifically, the charge accumulated is diminished a very small amount, due to protein binding without base flipping. Thus a small diminution of charge upon incubation with a protein that does not disrupt DNA structure, or a large diminution upon incubation with a protein that does disrupt the DNA structure is evidence that the electrochemical measurement is a reflection of protein binding.

Figure 19A:
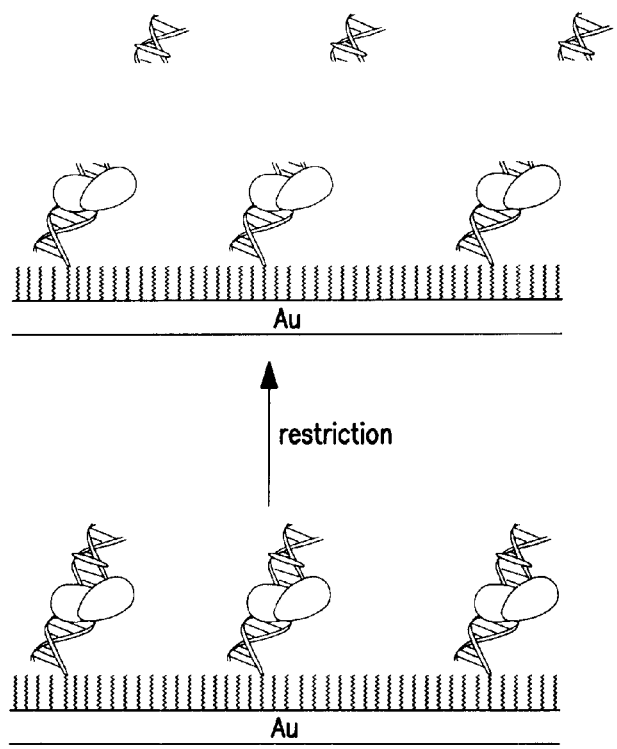
Figure 19B:
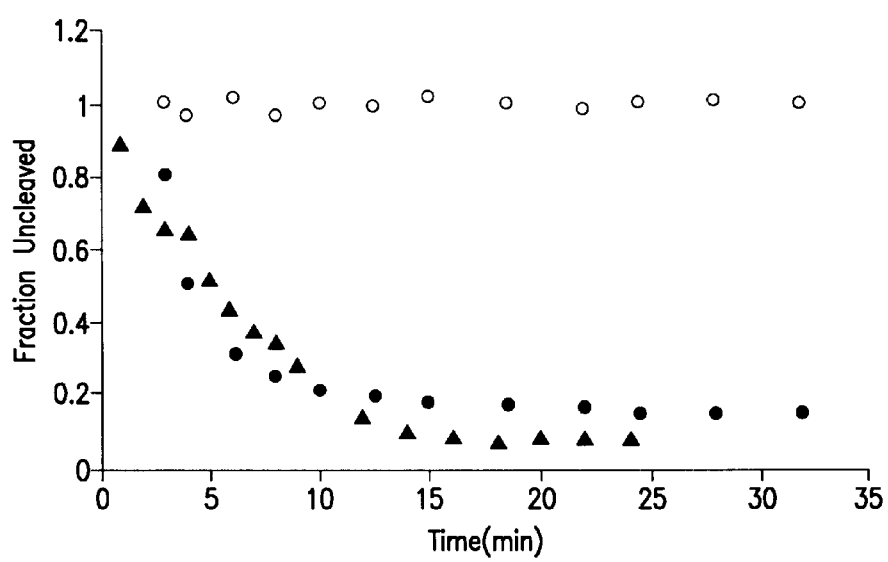

FIG. 19 illustrates charge transport through DNA-modified surfaces, which can be used to follow enzyme kinetics. FIG. 19A illustrates the inculation of DM-crosslinked, surface-bound oligonucleotide duplexes containing the restriction site for PvuII with the enzyme. As it cuts, the end of the duplex containing the redox probe is released from the surface (FIG. 19A). The release of the redox probe results in a decrease in the amount of DM reduction over time (FIG., 19B). The graph in FIG. 19B illustrates the plot of amount of charge accumulated at the DNA film as a function of enzyme reaction time. The same surface incubated without PvuII shows no decrease in DM reduction over time.

Table 1 describes the electrochemical detection of single-base mismatches based on cyclic voltammograms measured for 1.0 $\mu$M daunomycin noncovalently bound to duplex-modified electrodes.

DETAILED DESCRIPTION OF THE INVENTION

The expression "amplification of polynucleotides" includes methods such as polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf (1986).

The term "base-stacking perturbations" refers to any event that causes a perturbation in base-stacking such as, for example, a base-pair mismatch, a protein binding to its recognition site, an abasic site, a bulge, or any other entities that form oligonucleotide adducts.

The term "base flipping" refers to the process by which a target nucleic acid base is flipped out of the double helix, making that base accessible for reaction.

The term "denaturing" refers to the process by which strands of oligonucleotide duplexes are no longer base-paired by hydrogen bonding and are separated into single-stranded molecules. Methods ccof denaturation are well known to those skilled in the art and include thermal denaturation and alkaline denaturation.

The term "electrode" refers to an electric conductor that conducts a current in and out of an electrically conducting medium. The two electrodes, the anode and the cathode, receive and emit electrons, respectively. An electrode is used generally to describe the conductor. In the present invention, an electrode may also be a microarray, consisting of a number of separately addressable electrodes, or an ultramicroelectrode.

The term "hybridized" refers to two nucleic acid strands associated with each other which may or may not be fully base-paired.

The term "intercalative moieties" refers to planar aromatic or heteroaromatic moieties that are capable of partial insertion and stacking between adjacent base pairs of double-stranded oligonucleotides. These moieties may be small molecules or part of a larger entity, such as a protein. Within the context of this invention the intercalative moiety is able to generate a response or mediate a catalytic event.

The term "lesion" refers to an abnormal change in structure of DNA or RNA. The lesions may include mutations and mismatches in the DNA or RNA and may be naturally occurring, or non-naturally occurring.

The term "mismatches" refers to nucleic acid bases within hybridized duplexes which are not 100% complementary. A mismatch includes any incorrect pairing between the bases of two nucleotides located on complementary strands of DNA that are not the Watson-Crick base-pairs A:T or G:C. The lack of total homology may be due to deletions, insertions, inversions, substitutions or frameshift mutations.

The term "mutation" refers to a sequence rearrangement within DNA. The most common single base mutations involve substitution of one purine or pyrimidine for the other (e.g., A for G or C for T or vice versa), a type of mutation referred to as a "transition". Other less frequent mutations include "transversions" in which a purine is substituted for a pyrimidine, or vice versa, and "insertions" or "deletions", respectively, where the addition or loss of a small number (1, 2 or 3) of nucleotides arises in one strand of a DNA duplex at some stage of the replication process. Such mutations are also known as "frameshift" mutations in the case of insertion/deletion of one of two nucleotides, due to their effects on translation of the genetic code into proteins. Mutations involving larger sequence rearrangement also may occur and can be important in medical genetics, but their occurrences are relatively rare compared to the classes summarized above.

The term "nucleoside" refers to a nitrogenous heterocyclic base linked to a pentose sugar, either a ribose, deoxyribose, or derivatives or analogs thereof. The term "nucleotide" relates to a phosphoric acid ester of a nucleoside comprising a nitrogenous heterocyclic base, a pentose sugar, and one or more phosphate or other backbone forming groups; it is the monomeric unit of an oligonucleotide. Nucleotide units may include the common bases such as guanine (G), adenine (A), cytosine (C), thymine (T), or derivatives thereof. The pentose sugar may be deoxyribose, ribose, or groups that substitute therefore.

The terms "nucleotide analog", "modified base", "base analog", or "modified nucleoside" refer to moieties that function similarly to their naturally occurring counterparts but have been structurally modified.

The terms "oligonucleotide" or "nucleotide sequence" refers to a plurality of joined nucleotide units formed in a specific sequence from naturally occurring heterocyclic bases and pentofuranosyl equivalent groups joined through phosphorodiester or other backbone forming groups.

The terms "oligonucleotide analogs" or "modified oligonucleotides" refer to compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, which are known for use in the art.

The terms "redox-active moiety" or "redox-active species" refers to a compound that can be oxidized and reduced, i.e. which contains one or more chemical functions that accept and transfer electrons.

The term "redox protein" refers to proteins that bind electrons reversibly. The simplest redox proteins, in which no prosthetic group is present, are those that use reversible formation of a disulfide bond between two cysteine residues, as in thioredoxin. Most redox proteins however use prosthetic groups, such as flavins or NAD. Many use the ability of iron or copper ions to exist in two different redox states.

The present invention provides a highly sensitive and accurate method based on an electrochemical assay using intercalative, redox-active species to determine the presence and location of a single or multiple base-pair mismatches. Briefly, the system is comprised of (i) a reagent mixture comprising an electrode-bound oligonucleotide duplex to which an intercalative, redox-active moiety is associated and (ii) means for detecting and quantitating the generated electrical current or charge as an indication for the presence of a fully base-paired versus a mismatch containing duplex. The present invention is particularly useful in the diagnosis of genetic diseases that arise from point mutations. For example, many cancers can be traced to point mutations in kinases, growth factors, receptors binding proteins and/or nuclear proteins. Other diseases that arise from genetic disorders include cystic fibrosis, Bloom's syndrome, thalassemia and sickle cell disease. In addition, several specific genes associated with cancer, such as DCC, NF-1, RB, p53, erbA and the Wilm's tumor gene, as well as various oncogenes, such as abl, erbB, src, sis, ras, fos, myb and myc have already been identified and examined for specific mutations.

The present invention provides methods for detecting single or multiple point mutations, wherein the oligonucleotide duplex carrying the redox-active species is adsorbed and therefore continuously exposed to an electrode whose potential oscillates between a potential sufficient to effect the reduction of said chemical moiety and a potential sufficient to effect the oxidation of the chemical moiety. This method is preferred over other methods for many reasons. Most importantly, this method allows the detection of one or more mismatches present within an oligonucleotide duplex based on a difference in electrical current measured for the mismatch-containing versus the fully base-paired duplex. Thus the method is based on the differences in base-stacking of the mismatches and is independent of the sequence composition of the hybridized duplex, as opposed to existing methods that depend on thermodynamic differences in hybridization. Furthermore, this method is nonhazardous, inexpensive, and can be used in a wide variety of applications, alone or in combination with other hybridization-dependent methods.

One particular aspect of the invention relates to the method for sequential detection of mismatches within a number of nucleic acid samples which includes: at least one strand of a nucleic acid molecule is hybridized under suitable conditions with a first nucleic acid target sequence forming a duplex which potentially contains a mismatch, and wherein one of the nucleic acids is derivatized with a functionalized linker. This duplex is then deposited onto an electrode or an addressable multielectrode array forming a monolayer. An intercalative, redox-active species (e.g., daunomycin) is noncovalently adsorbed (or crosslinked, if desired) onto this molecular lawn, and the electrical current or charge generated is measured as an indication of the presence of a base pair mismatch within the adsorbed oligonucleotide complex. Subsequent treatment of the duplexes containing the intercalative, redox-active species under denaturing conditions allows separation of the complex, yielding a single-stranded monolayer of oligonucleotides which can be rehybridized to a second oligonucleotide target sequence. The steps of duplex formation, adsorption of the intercalative, redox-active species, measurement of the electrical current or charge, and denaturation of the complex to regenerate the single-stranded oligonucleotides may be repeated as often as desired to detect in a sequential manner genetic point mutations in a variety of oligonucleotide probes.

The charges passed at each of the electrodes are measured and compared to the wild-type, i.e. fully base-paired, sequences. Electrodes with attenuated signals correspond to mutated sequences, while those which exhibit no change in electrical current or charge are unmutated.

Another aspect of the invention relates to the method of detecting mutations utilizing electrocatalysis. Briefly, the modification of electrode surfaces with oligonucleotide duplexes provides a medium that is impenetrable by negatively charged species due to the repulsion by the high negative charge of oligonucleotides. However, electrons can be shuttled through the immobilized duplexes to redox-active intercalators localized on the solvent-exposed periphery of the monolayer, which in turn can catalytically reduce these negatively charged species. More specifically, this electrocatalytic method includes: at least one strand of a nucleic acid molecule is hybridized under suitable conditions with a first nucleic acid target sequence forming a duplex which potentially contains a mismatch, and wherein one of the nucleic acids is derivatized with a functionalized linker. This duplex is then deposited onto an electrode or a multielectrode array forming a monolayer. The assembly is immersed into an aqueous solution containing both an intercalative, redox-active species (e.g., methylene blue) and a non-intercalative, redox-active species (e.g., ferricyanide). The electrical currents or charges corresponding to the catalytic reduction of ferricyanide mediated by methylene blue are measured for each nucleic acid-modified electrode at the potential of methylene blue and compared to those obtained with wild-type, i.e. fully base-paired sequences. Subsequent treatment of the duplexes under denaturing conditions allows separation of the complex, yielding a single-stranded monolayer of oligonucleotides which can be rehybridized to a second oligonucleotide target sequence. The steps of duplex formation, measurement of the catalytically enhanced electrical current or charge, and denaturation of the complex to regenerate the single-stranded oligonucleotides may be repeated as often as desired to detect in a sequential manner genetic point mutations in a variety of oligonucleotide probes. This particular method based on electrocatalysis at oligonucleotide-modified surfaces is extremely useful for systems where attenuated signals resulting from the presence of mismatches are small. The addition of a non-intercalative electron acceptor amplifies the signal intensity, and allows more accurate measurements. This approach may be particularly useful to monitor assays based on redox-active proteins which bind to the oligonucleotide-modified surface, but are not easily oxidized or reduced because the redox-active center is not intercalating.

Another aspect of the invention relates to the electrocatalytic method for detecting all possible single base mismatches, a small number of mutated DNA samples within a large pool of wild-type sequences, several naturally occurring base lesions and single base lesions in either DNA or RNA/DNA hybrids. More specifically, this electrocatalytic method includes: a first single stranded nucleic acid probe sequence is contacted with a second single stranded nucleic acid target sequence in order to form a duplex. The first single stranded nucleic acid may be derivatized with a thiol-terminated alkyl chain, or other derivative. The second single stranded nucleic acid target sequence is hybridized to a monolayer of first single stranded nucleic acid probe sequences on an electrode. The monolayer of first single stranded nucleic acid probe sequences is prepared by first attaching a duplex containing the first single stranded nucleic acid probe sequence to the electrode, dehybridizing the duplex, such that the first single stranded nucleic acid probe sequence remains attached to the electrode. The hybrid of the first single stranded nucleic acid probe sequence and the second single stranded target sequence form a double stranded nucleic acid-modified film. The nucleic acid-modified film is immersed in a solution comprising an intercalative, redox-active moiety (e.g. methylene blue ($MB^+$) and a non-intercalative redox-active moiety (e.g. ferricyanide). In the electrocatalytic process, electrons flow from the electrode surface to intercalated $MB^+$ in a DNA-mediated reaction. The reduced form of $MB^+$, leucomethylene blue ($LB^+$), in turn reduces solution-borne ferricyanide, so that more electrons can flow to $MB^+$ and the catalytic cycle continues (FIG. 9). Thus in one experiment the surface-bound DNA is repeatedly interrogated. In double-stranded duplexes containing one or more mismatches, fewer $MB^+$ molecules are electrochemically reduced, so the concentration of active catalyst is greatly lowered and the overall electrocatalytic response is diminished. As a result, the catalytic reaction amplifies the absolute signal corresponding to $MB^+$ in addition to enhancing the inhibitory affect associated with a mismatch. Furthermore, due to its catalytic nature, the measured charge increases with increased sampling times, and in principle is limited only by the concentration of ferricyanide in solution. The electrical current or charges of the catalytic reduction of the non-intercalative, redox-active species by the intercalative, redox-active moiety are measured and a difference of the electric current or charge from the electrical current or charge of a nucleic acid duplex not having one or more single-base sequence lesions is indicative of the presence or absence of one or more single-base sequence lesions in the target sequence.

The present invention further relates to the nature of the redox-active species. These species have a reduced state in which they can accept electron(s) and an oxidized state in which they can donate electron(s). The intercalative, redox-active species that are adsorbed or covalently linked to the oligonucleotide duplex include, but are not limited to, intercalators and nucleic acid-binding proteins which contain a redox-active moiety. Covalent attachment of the intercalative, redox-active moiety to the DNA monolayer is not required because binding is primarily constrained to the top of individual helices within the DNA films. The non-covalently bound dye should be intercalatively stacked. Charge transport through the DNA film to the intercalative, redox-active moiety begins the catalytic cycle. Furthermore, completion of the catalytic cycle involves reaction with negatively charged ferricyanide, which is electrostatically repulsed from the interior of the anionic DNA film. Thus only the intercalative, redox-active moiety bound near the top of the film is solution accessible, and can therefore participate in the catalytic cycle.

An intercalator useful for the specified electrochemical assays is an agent or moiety capable of partial insertion between stacked base pairs in the nucleic acid double helix. Examples of well-known intercalators include, but are not limited to, phenanthridines (e.g., ethidium), phenothiazines (e.g., methylene blue), phenazines (e.g., phenazine methosulfate), acridines (e.g., quinacrine), anthraquinones (e.g., daunomycin), and metal complexes containing intercalating ligands (e.g., phi, chrysene, dppz). Some of these intercalators may interact site-selectively with the oligonucleotide duplex. For example, the chrysene ligand is known to intercalate at the mispaired site of a duplex itself (Jackson, 1997), which can be exploited for selective localization of an intercalator. This can be in particular useful to construct a duplex monolayer which contains the intercalative, redox-active species exclusively at its periphery.

The choice of a protein depends on its adsorption and binding properties to biological macromolecules, e.g. nucleic acids, and with non-biological macromolecules, whether in a homogeneous solution, or when immobilized on a surface. By changing the absorption or binding characteristics, selectivity, signal to noise ratio and signal stability in these assays can be improved. The charge of a protein affects its adsorption on surfaces, absorption in films, electrophoretic deposition on electrode surfaces, and interaction with macromolecules. It is, therefore, of importance in diagnostic and analytical systems utilizing proteins to tailor the charge of the protein so as to enhance its adsorption or its binding to the macromolecule of choice, e.g. the nucleic acid. In other cases, e.g. when the detection assay is used during several cycles, it is of equal importance to be able to facilitate desorption, removal, or stripping of the protein from the macromolecule. These assays require oligonucleotide duplexes that are designed such as to allow for site-specific binding of the protein of choice, which may require a single-stranded overhang. Once the protein is adsorbed onto the nucleic acid, electrons are relayed via the oligonucleotide duplex to the electrode.

The nature of the non-intercalative, redox-active species used in a particular electrocatalytic assay depends primarily on the redox potential of the intercalating, redox-active species utilized in that same assay. Examples include, but are not limited to, any neutral or negatively charged probes, for example ferricyanide/ferrocyanide, ferrocene and derivatives thereof (e.g., dimethylaminomethyl-, monocarboxylic acid-, dicarboxylic acid-), hexacyanoruthenate, and hexacyanoosmate.

In the case of nucleic acid-binding proteins, differences in DNA-mediated electron transfer between the duplex-bound protein and the electrode allow for the detection of base-pair mismatches, base flipping, or other base-stacking perturbations. Additionally, the protein-DNA interaction allows a method of electrical monitoring of DNA enzymatic reactions in a duplex nucleic acid sequence.

One aspect of the present invention relates to an electrochemical assay of protein binding to nucleic acid-modified electrodes based upon the detection of base flipping in the DNA base stacking, using DNA charge transport. This assay provides a method for probing protein-dependent changes in nucleic acid structure. At least one strand of a single stranded derivatized nucleic acid sequence containing a protein binding sequence and an electrochemical probe binding sequence is hybridized to a second single stranded nucleic acid sequence to form a duplex, wherein the second single stranded nucleic acid sequence is hybridized to a monolayer of first single stranded nucleic acid sequences on an electrode. The monolayer is prepared by first attaching a duplex comprising the first single stranded nucleic acid sequence to the electrode, and dehybridizing the duplex, such that the first single stranded nucleic acid sequence remains attached to the electrode, and wherein the hybrid of the first single stranded nucleic acid sequence and the second single stranded sequence form a double stranded nucleic acid-modified film. To this film is added an electrochemical probe, which binds to the electrochemical probe binding sequence of the first single stranded nucleic acid sequence. A protein is added to the double stranded nucleic acid modified film, which binds to the protein binding sequence of the first single stranded nucleic acid sequence. The charges produced are measured and compared to the charges measured without the protein and a difference of the electrical current of charge from the electrical current or charge of a nucleic acid duplex not having a protein bound to the duplex DNA is indicative of the presence or absence of base flipping due to protein binding in the duplex.

In one preferred embodiment, the electrochemical probe is daunomycin, which is covalently crosslinked to a guanine residue near the duplex terminus. In order to ensure the binding site of the redox probe, daunomycin is covalently crosslinked to the top of the DNA film. The covalent adduct is formed by reaction with the exocyclic amine in guanine residues in the presence of formaldehyde. All guanines in the duplex are replaced by inosines (I; guanine without the exocyclic amine) except those at the end of the duplex where the daunomycin is intended. In another embodiment, the double stranded nucleic acid-modified film is formed without the presence of $Mg^{2+}$. After assembly of the duplexes, the remaining exposed surface is filled, or "backfilled," with mercaptohexanol. In one illustrative example, the protein is the methyltransiferase HhaI (M.HhaI), the mutant M.HhaI Q237W, or uracil-DNA glycosylase (See examples 23–28).

Another aspect of the present invention relates to an electrochemical assay of protein binding to nucleic acid-modified electrodes based upon the detection of associated perturbations in the DNA base stacking, using DNA charge transport. This assay provides a method for probing protein-dependent changes in nucleic acid structure. At least one strand of a single stranded derivatized nucleic acid sequence containing a protein binding sequence and an electrochemical probe binding sequence is hybridized to a second single stranded nucleic acid sequence to form a duplex, wherein the second single stranded nucleic acid sequence is hybridized to a monolayer of first single stranded nucleic acid sequences on an electrode. The monolayer is prepared by first attaching a duplex comprising the first single stranded nucleic acid sequence to the electrode, and dehybridizing the duplex, such that the first single stranded nucleic acid sequence remains attached to the electrode, and wherein the hybrid of the first single stranded nucleic acid sequence and the second single stranded sequence form a double stranded nucleic acid-modified film. To this film is added an electrochemical probe, which binds to the electrochemical probe binding sequence of the first single stranded nucleic acid sequence. A protein is added to the double stranded nucleic acid modified film, which binds to the protein binding sequence of the first single stranded nucleic acid sequence. The charges produced are measured and compared to the charges measured without the protein and a difference of the electrical current of charge from the electrical current or charge of a nucleic acid duplex not having a protein bound to the duplex DNA is indicative of the presence or absence of perturbations in the DNA base stacking due to protein binding in the duplex.

In one embodiment, the electrochemical probe is daunomycin, which is covalently crosslinked to a guanine residue near the duplex terminus. In order to ensure the binding site of the redox probe, daunomycin is covalently crosslinked to the top of the DNA film. The covalent adduct is formed by reaction with the exocyclic amine in guanine residues in the presence of formaldehyde. All guanines in the duplex are replaced by inosines (I; guanine without the exocyclic amine) except those at the end of the duplex where the daunomycin is intended. In another embodiment, the double stranded nucleic acid-modified film is formed without the presence of $Mg^{2+}$. After assembly of the duplexes, the remaining exposed surface is filled with mercaptohexanol. In one illustrative example, the protein used is TATA-box binding protein (TBP) or R.PvuII (See examples 23–28).

Yet another aspect of the invention relates to a method of electrochemical monitoring of DNA enzymatic reactions in a duplex nucleic acid sequence associated with protein binding to the duplex nucleic acid sequence, using DNA charge transport. This assay provides a method for probing protein-dependent changes in nucleic acid structure. At least one strand of a single stranded derivatized nucleic acid sequence containing a protein binding sequence and an electrochemical probe binding sequence is hybridized to a second single stranded nucleic acid sequence to form a duplex, wherein the second single stranded nucleic acid sequence is hybridized to a monolayer of first single stranded nucleic acid sequences on an electrode. The monolayer is prepared by first attaching a duplex comprising the first single stranded nucleic acid sequence to the electrode, and dehybridizing the duplex, such that the first single stranded nucleic acid sequence remains attached to the electrode, and wherein the hybrid of the first single stranded nucleic acid sequence and the second single stranded sequence form a double stranded nucleic acid-modified film. To this film is added an electrochemical probe, which binds to the electrochemical probe binding sequence of the first single stranded nucleic acid sequence. A protein is added to the double stranded nucleic acid modified film, which binds to the protein binding sequence of the first single stranded nucleic acid sequence. The charges produced are measured and compared to the charges measured without the protein and a difference of the electrical current of charge from the electrical current or charge of a nucleic acid duplex not having a protein bound to the duplex DNA is indicative of the presence or absence of an enzymatic reaction of the duplex.

In one embodiment, the electrochemical probe is daunomycin, which is covalently crosslinked to a guanine residue near the duplex terminus. In order to ensure the binding site of the redox probe, daunomycin is covalently crosslinked to the top of the DNA film. The covalent adduct is formed by reaction with the exocyclic amine in guanine residues in the presence of formaldehyde. All guanines in the duplex are replaced by inosines (I; guanine without the exocyclic amine) except those at the end of the duplex where the daunomycin is intended. In another embodiment, the double stranded nucleic acid-modified film is formed without the presence of $Mg^{2+}$. After assembly of the duplexes, the remaining exposed surface is filled with mercaptohexanol. In one aspect, the protein used is a restriction endonuclease, such as PvuII (See examples 23–28).

Yet another aspect of the invention relates to a method of detecting the presence or absence of a protein inducing base-stacking perturbations in DNA duplexes, this method comprising the following steps. At least one strand of a nucleic acid molecule is hybridized under suitable conditions with a second strand of nucleic acid molecule forming a duplex, wherein one of the nucleic acids is derivatized with a functionalized linker. This duplex is designed such to contain the recognition site of a protein of choice at a distinct site along that duplex. This duplex is then deposited onto an electrode or an addressable multielectrode array forming a monolayer and an intercalative, redox-active species is adsorbed onto this molecular lawn. In a preferred embodiment, the intercalative, redox-active species is site-specifically localized. In another preferred embodiment, the intercalative, redox-active species is crosslinked to the oligonucleotide duplex. This formed complex is then exposed to a sample solution that potentially contains the specific protein and the electrical current or charge generated is measured as an indication of the presence or absence of the protein. Subsequently, the protein is removed under appropriate conditions to regenerate the duplex containing the intercalative, redox-active moiety. The steps of duplex formation, adsorption or crosslinking of the intercalative, redox-active species, measurement of the electrical current or charge, and regeneration of the duplex containing the intercalative, redox-active moiety may be repeated as often as desired to detect in a sequential manner the presence of a specific protein in multiple sample solutions.

The charges passed at each of the electrodes are measured and compared to the charges measured in a reference solution without the protein. Electrodes with attenuated signals indicate the presence of the protein in question which is binding to its recognition site, thus causing a perturbation in base-stacking. Examples of proteins that can be used for this assay include, but are not limited to, restriction enzymes, TATA-binding proteins, and base-flipping enzymes (e.g., DNA methylase).

The present invention also relates to the choice of nucleic acid probes. Any nucleic acid, DNA or RNA, can be subjected to this mismatch detection method, provided that the mismatch(es) to be detected lie within the region between the attachment site of the intercalative, redox-active moiety and the electrode in order to be able to measure a difference in electrical current. The nucleic acid probes to be compared may comprise natural or synthetic sequences encoding up to the entire genome of an organism. These probes can be obtained from any source, for example, from plasmids, cloned DNA or RNA, or from natural DNA or RNA from any source, including bacteria, yeast, viruses, organelles and higher organisms such as plants and animals. The samples may be extracted from tissue material or cells, including blood cells, amniocytes, bone marrow cells, cells obtained from a biopsy specimen and the like, by a variety of techniques as described for example by Maniatis et al., *Molecular Cloning: A Laboratory Manual,* Cold Spring Harbor Laboratory Cold Spring Harbor, N.Y. (1982), incorporated herein by reference.

Alternatively, the sequences of choice can also be prepared by well known synthetic procedures. For standard DNA and RNA synthesis methods, see for example "Synthesis and Applications of DNA and RNA" ed. S. A. Narang, Academic Press, 1987, M. J. Gait, "Oligonucleotide Synthesis", IRL Press, Wash. D.C. U.S.A., 1984, and "Oligonucleotides and Analogues" ed. F. Eckstein, IRL Press, Wash. D.C. U.S.A., 1991, as incorporated herein by reference. Briefly, oligonucleotides and oligonucleotide analogs may be synthesized, conveniently through solid state synthesis of known methodology. In a preferred embodiment, the monomeric units are added to a growing oligonucleotide chain which is covalently immobilized to a solid support. Typically, the first nucleotide is attached to the support through a cleavable linkage prior to the initiation of synthesis. Step-wise extension of the oligonucleotide chain is normally carried out in the 3' to 5' direction. When the synthesis is complete, the polymer is cleaved from the support by hydrolyzing the linkage mentioned above and the nucleotide originally attached to the support becomes the 3' terminus of the resulting oligomer. Nucleic acid synthesizers such as the Applied Biosystems, Incorporated 380B are commercially available and their use is generally understood by persons of ordinary skill in the art as being effective in generating nearly any oligonucleotide or oligonucleotide analog of reasonable length which may be desired. Triester, phosphoramidite, or hydrogen phosphonate coupling chemistries are used with these synthesizers to provide the desired oligonucleotides or oligonucleotide analogs.

In addition, the invention also relates to nucleic acid probes that are constructed with a defined sequence comprised of nucleotide and non-natural nucleotide monomers to restrict the number of binding sites of the intercalative, redox-active agent to one single site. For example, in the case of the redox-active intercalator daunomycin mixed nucleotide/non-natural nucleotide oligomers were prepared containing A-T and/or I-C basepairs and one discrete guanine binding site to which daunomycin is crosslinked. The non-natural nucleotides are constructed in a step-wise fashion to produce a mixed nucleotide/non-natural nucleotide polymer employing one of the current DNA synthesis methods well known in the art, see for example "Synthesis and Applications of DNA and RNA" ed. S. A. Narang, Academic Press, 1987, M. J. Gait, "Oligonucleotide Synthesis", IRL Press, Wash. D.C. U.S.A., 1984, and "Oligonucleotides and Analogues" ed. F. Eckstein, IRL Press, Wash. D.C. U.S.A., 1991.

Methods and conditions used for contacting the oligonucleotide strands of two DNAs, two RNAs or one DNA and one RNA molecule under hybridizing conditions are widely known in the art. Suitable hybridization conditions may be routinely determined by optimization procedures well known to those skilled in the art to establish protocols for use in a laboratory. See e.g., Ausubel et al., *Current Protocols in Molecular Biology, Vol.* 1–2, John Wiley & Sons (1989); Sambrook et al., Molecular Cloning A Laboratory Manual, 2nd Ed., Vols. 1–3, Cold Springs Harbor Press (1989); and Maniatis et al., *Molecular Cloning: A Laboratory Manual,* Cold Spring, Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

Another aspect of the invention relates to a surface-modified electrode and its use in a bioelectrochemical process, in which electrons are transferred directly between an electrode and an electroactive biological material which is capable of accepting or donating one or more electrons. Such a bioelectrochemical process can be in either direction. In particular, the invention provides electrodes having their surface modified with oligonucleotide duplexes carrying an intercalative, redox-active moiety. The electrode can be of any material compatible with the surface modifier being adsorbed or bound thereon, including, but not limited to, noble metals such as gold, silver, platinum, palladium, as well as carbon. The preferred material for the electrodes are gold and carbon.

The oligonucleotide duplex can be adsorbed onto the electrode in any convenient way. Preferably, the process of preparing such a modified electrode includes adsorbing the oligonucleotide duplex which is derivatized at the 5'-end with a functionalized linker chains onto the electrode surface in one monolayer to obtain a uniform lawn. These linkers include, but are not limited to, thiol- or amine-terminated chains. This process is generally understood by persons of ordinary skill in the art as and is relatively simple, reproducible and can easily be automated.

Furthermore, the density and composition of the monolayer is subject to variation depending on the selected assay. Methods of detecting single base-pair mismatches using intercalative, redox-active moieties require a densely packed monolayer to prevent the adsorbed intercalative, redox-active moieties from diffusing into the lawn. The method for detecting the presence or absence of a protein requires preferably an uneven monolayer comprised of duplexes of variable length to allow the protein to bind effectively to its recognition site along the duplex. Alternatively, the monolayer may be less dense. Less dense monolayers may be prepared by a combination of lowering the ionic strength of the buffer, decreasing the concentration of the derivatized oligonucleotides in the solution deposited on the electrode, or shortening the time for deposition of the duplex onto the electrode.

In addition, the present invention further relates to methods of creating a spatially addressable array of adsorbed duplexes. In a preferred embodiment, oligonucleotide duplexes of variable sequence composition that are derivatized at the 5'-end with a functionalized linker are deposited onto a multielectrode array. Subsequent treatment of these electrode-bound duplexes under denaturing conditions yields a monolayer of single-stranded oligonucleotides, which can then be hybridized with a complementary oligonucleotide probe that potentially contains a mismatch. In another preferred embodiment, short oligonucleotide duplexes (5 to 10 base-pairs in length) that are derivatized on one end with a functionalized linker and contain single-stranded overhangs (5 to 10 nucleotides in length) of designed sequence composition at the opposite end are deposited onto a multielectrode array to generate a spatially addressable matrix. These electrode-bound duplexes can then be hybridized with single-stranded or double-stranded oligonucleotides that contain the complementary overhang.

Solid supports containing immobilized molecules have been extensively used in research, in clinical analyses and in the commercial production of foods and chemicals (see e.g., U.S. Pat. No. 5.153,166; Akashi, 1992). Immobilized nucleic acids are used in hybridization assays (Lamture, 1994) and immobilized proteins in radioimmuno or ELISA assays (see, U.S. Pat. No. 5,314,830). In addition, enzymes have been immobilized to facilitate their separation from product and to allow for their efficient and repetitive use. A number of important factors have to be considered in the development of an effective immobilization procedure. First, the procedure must minimize non-specific adsorption of molecules. Second, the procedure must maintain the, functional integrity of the immobilized molecules. Third, the stability of the bond between the support and the immobilized molecule must be such to avoid leaching which would lead to reduced accuracy and sensitivity. Finally, the coupling procedure must be efficient enough to result in a support with a high capacity for the target molecules as well as be cost effective.

Another aspect of the invention relates to measuring the electrical current as a function of degree of hybridization of the oligonucleotide duplex adsorbed onto the electrode. When the intercalative, redox-active species is exposed to electrochemical or chemical energy, the electrical current may be continuously detected using techniques well known in the art. These include, but are not limited electronic methods, for example voltammetry or amperommetry, or optical methods, for example fluorescence or phosphorescence.

Generally, photoluminescence excitation and emission occur with electromagnetic radiation of between about 200 nanometers and about 900 nanometers in wavelength. Likewise, chemiluminescent and electrochemiluminescent emission generally occur with the emitted electromagnetic radiation being between about 200 nanometers and about 900 nanometers in wavelength. The potential at which the reduction or oxidation of the chemical moiety occurs depends upon its exact chemical structure as well as factors such as the pH of the solution and the nature of the electrode used. It is well known how to determine the optimal emission and excitation wavelengths in a photoluminescent system and the optimal potential and emission wavelength of an electrochemiluminescent and chemiluminescent system.

There are many methods for quantifying the amount of luminescent species present. The rate of energy input into the system can provide a measure of the luminescent species. Suitable measurements include, for example, measurements of electric current when the luminescent species is generated electrochemically, the rate of reductant or oxidant utilization when the luminescent species is generated chemically or the absorption of electromagnetic energy in photoluminescent techniques. In addition, the luminescent species can be detected by measuring the emitted electromagnetic radiation. All of these measurements can be made either as continuous, event-based measurements, or as cumulative methods which add the signal over a long period of time. Event-based measurements may be carried out with photomultiplier tubes, photodiodes or phototransistors to produce electric currents proportional in magnitude to the incident light intensity, or by using charge couple devices. Examples of cumulative methods are the integration of event-based data, and the use of photographic film to provide cumulative data directly.

The publications and other reference materials referred to herein describe the background of the invention and provide additional detail regarding its practice and are hereby incorporated by reference. For convenience, the reference materials are referenced and grouped in the appended bibliography.

The invention will be further described with reference to the following examples; however, it is to be understood that the invention is not limited to such examples.

EXAMPLES

Materials

Phosphoramidite reagents (including the $C_6$S-S thiol modifier) were obtained from Glen Research. [$\gamma$-$^{32}$P]dATP was obtained from NEN-DuPont. Potassium ferrocyanicle (Fisher) was recrystallized from aqueous solution prior to use. Daunomycin was obtained from Fluka.

Synthesis of Derivatized Duplexes

Oligonucleotides immobilized on a controlled pore glass resin were treated in succession with carbonyldiimidazole and 1,6-diaminohexane (1 g/10 ml dioxane, 30 min/ea.) at the 5'-hydroxy terminus before cleavage from the resin (Wachter, 1986). After deprotection, the free amine was treated with 2-pyridylthiopropionic acid N-succinimide ester to produce a disulfide (Harrison, 1997). The sequences were purified by reverse-phase HPLC, converted to free thiols using dithiothreitol, and repurified before hybridization to their complements. Derivatized oligonucleotides were characterized by mass-assisted laser desorption ionization time-of-flight mass spectrometry and HPLC retention times. Duplexes were hybridized in deoxygenated 5 mM phosphate/50 mM NaCl (pH 7) by heating to 90° C. followed by slow cooling to room temperature. Unprotected duplexes were stored frozen under argon to prevention oxidation of the thiol.

Atomic Force Microscopy (AFM)

All AFM images were collected using a MultiMode AFM running on the NanoScope IIIa controller (Digital Instruments, Santa Barbara, Calif.). A glass AFM chamber (Digital Instruments, Santa Barbara, Calif.) and a fluid volume of approximately 50 microliters were used for the experiments. $Si_3N_4$ cantilevers (spring constant, 0.06 N/m) with integrated, end-mounted oxide-sharpened $Si_3N_4$ probe tips were used. The applied vertical force of the AFM probe during imaging was minimized to beneath 100 pN. Continually adjusting the cantilever deflection feedback setpoint compensated for thermal drifting of the cantilever and a consistent, minimum force was maintained AFM height calibrations were carried out on a NIST-traceable 180-nm height standard and then confirmed by measuring a single-atom step in the Au gold surface. The AFM images were recorded in "Height" (or constant force) mode. Holes in the monolayer used to determine monolayer thicknesses were prepared by decreasing the scan size to approximately 100–150 nm, increasing the scan rate to 24–30 Hz, and increasing the vertical force by advancing the setpoint several units. After about one minute, the scan size, scan rate, and setpoint were returned to their previous values, and images featuring a bare gold square were captured. All images captured for height-contrast analysis were recorded at minimum vertical tip forces. This was accomplished by decreasing the set-point until the tip disengaged from the surface, then reintroducing it with the minimum force required to achieve a stable image. In several cases, the film height was also measured in tapping mode, and gave the same result as the contact-mode experiments.

Electrochemistry

Cyclic voltammetry (CV) was carried out on 0.02 $cm^2$ polycrystalline gold electrodes using a Bioanalytical Systems (BAS) Model CV-50W electrochemical analyzer at 20±2° C. in 100 mM phosphate buffer (pH 7). A normal three-electrode configuration consisting of a modified gold-disk working electrode, a saturated calomel reference electrode (SCE, Fisher Scientific), and a platinum wire auxiliary electrode was used. The working compartment of the electrochemical cell was separated from the reference compartment by a modified Luggin capillary. Potentials are reported versus SCE. Heterogeneous electron-transfer rates were determined and analyzed by CV (Nahir, 1994; Weber, 1994; Tender, 1994).

Ellipsometry

Optical ellipsometry ($\lambda$=632.8 nm) was carried out on dried samples at 25° C. using a Gaertner Model L116C ellipsometer.

Example 1

Site-Specific Incorporation of a Redox-Active Intercalator Into a DNA Duplex.

Figure 1:
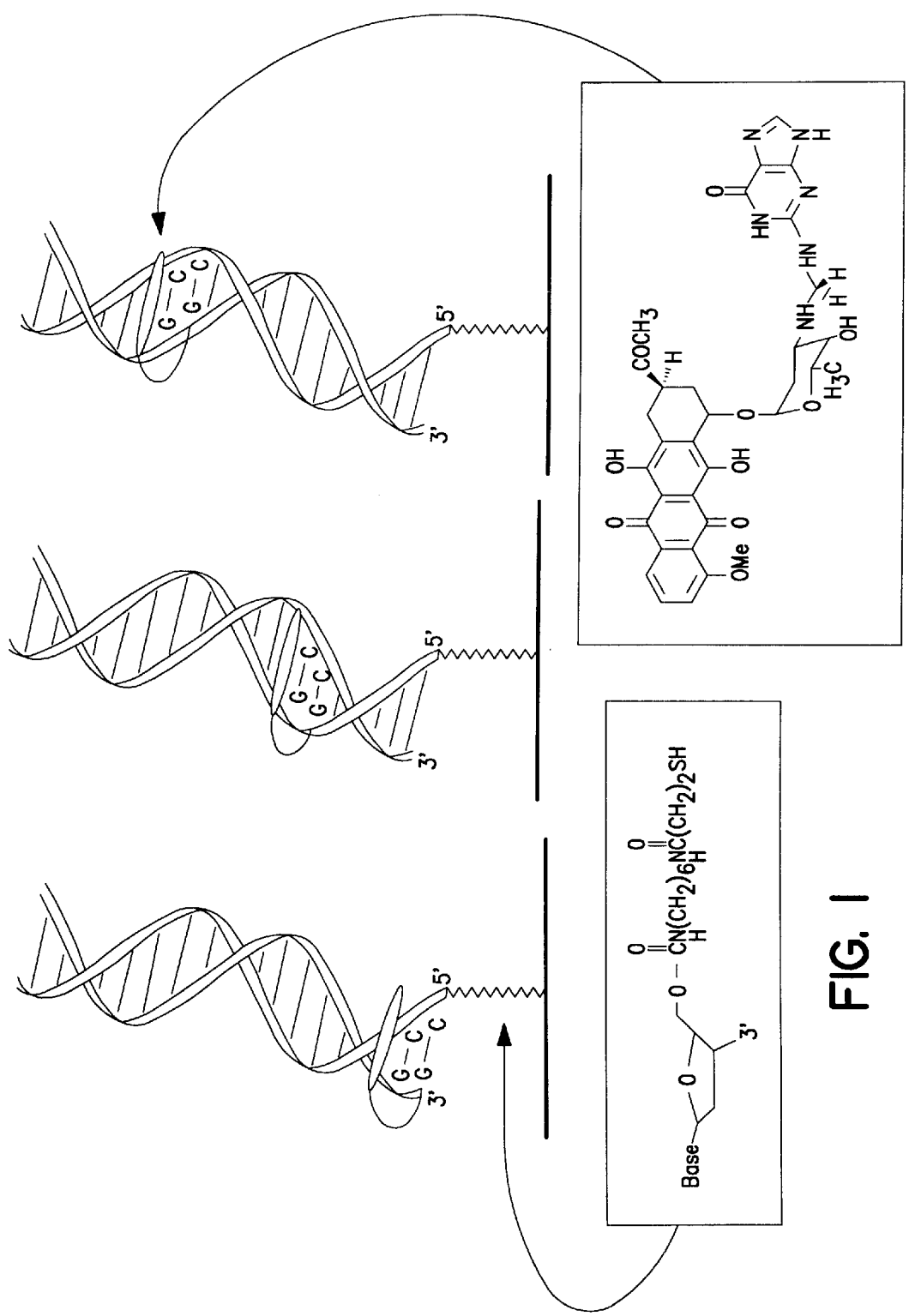
FIG. 1 is a schematic diagram depicting DNA duplexes used for study of distance-dependent reduction of daunomycin. The right insert illustrates the daunomycin-guanine crosslink. The left insert shows the thiol-terminated tether which connects the duplex to the electrode surface and provides 16 σ-bonds between the electrode and the base stack.

The redox-active intercalator daunomycin (DM) (Arcamone, 1981) was incorporated into the DNA duplex to investigate charge transduction through these duplexes (FIG. 1). DM undergoes a reversible reduction (Molinier- Jumel, 1978; Berg, 1981) within the potential window of the monolayers (Kelley, 1997a), and covalent adducts of intercalated DM crosslinked to the 2-amino group of guanine (Leng, 1996) have been crystallographically characterized within duplex DNA (Wang, 1991). Thus, a series of oligonucleotides primarily containing A-T or inosine (I)-C pairs were constructed with discrete guanine binding sites to which DM was crosslinked. Preferably, thiol-terminated duplexes (0.1 mM) containing an adjacent pair of guanines were hybridized, incubated with 0.2% formaldehyde and 0.2 mM DM in 5 mM phosphate, 50 mM NaCl, pH 7 for 1 h, and phenol extracted to remove excess DM.

Moving the guanine site along the duplex resulted in a systematic variation of the through-helix DM/gold separation, and allowed an investigation of the effect of distance on the dynamics of charge transport through the monolayers (FIG. 1).

Example 2

Characterization of DNA Duplexes Modified with a Redox-Active Intercalator.

Modified duplexes were characterized by mass spectrometry, ultraviolet/visible absorption spectroscopy, and thermal denaturation experiments, all of which were consistent with a 1:1 DM-duplex stoichiometry. For example, the duplex SH—$(CH_2)CONH(CH_2)_6NHCO_2$-5'ATCCTACTCATGGAC with its inosine complement modified with DM was analyzed by MALDI-TOF spectrometry. Mass-to-charge ratios (found/calc) of 5284/(5282) (DM+SH strand), 4541/(4540) (complement), and 4742/(4742) (SH strand) were detected. These values correspond to the calculated masses for fragments expected from this duplex. UV-visible absorption spectroscopy also revealed a 1:1 duplex/DM stoichiometry based upon comparison of the duplex absorbance at 260 nm (M=14.9×$10^3 M^{-1}$ $cm^{-1}$) and the absorbance of intercalated DM at 480 nm (M=5.1× $10^3 M^{-1}$ $cm^{-1}$). In the presence of 100 mM phosphate, 100 mM $MgCl_2$, and at pH 7, thermal denaturation studies of 5 DM duplexes (monitored by absorbance at 260 nm) revealed melting temperatures of 48 and 50° C. for the native and daunomycin-crosslinked duplexes, respectively. A similar melting profile was obtained by monitoring hypochromicity at 482 nm for the DM duplex.

Example 3

Preparation of Gold Electrodes Derivatized with DNA Duplexes.

Electrodes were conveniently prepared by modifying gold surfaces with 15 base-pair DNA duplexes derivatized at the 5' end with a thiol-terminated alkane chain. Bulk gold electrodes were polished successively with 0.3- and 0.5-$\mu$M alumina (Buhler), sonicated for 30 min, and etched in 1.0 M sulfuric acid. Au(111) surfaces were prepared by vapor deposition onto mica or glass (Widrig, 1991; Zei, 1983). Electrodes were then modified by incubation in 0.1 mM solutions of derivatized DNA duplexes in 5 mM phosphate/ 50 mM NaCl (pH 7) for 12–48 h at ambient temperature. Modified electrodes were rinsed in buffer prior to use.

Before deposition of the duplexes onto the gold surfaces, the presence of the free thiols was confirmed using a spectroscopic assay based on dithionitrobenzene (Riddles, 1979). Subsequently, the samples were deposited onto the gold surfaces for 12–24 h.

Electrochemical assays, radioactive tagging experiments, and atomic force microscopy (AFM) (Kelley, 1997a, 1997b) all indicate that the oligonucleotides form densely packed monolayers oriented in an upright position with respect to the gold surface.

Example 4

Characterization of Modified DNA Duplexes Monolayers on Gold Surfaces

The DM-modified duplexes readily formed self-assembled monolayers on gold. AFM studies of modified films reveal densely packed monolayers with heights greater than 45 Å at open circuit. More specific, AFM studies were carried out under electrochemical control, and revealed that the DNA films undergo a potential-dependent change in structure. At open circuit, the monolayer film height is 45(3) Å. Based on the anisotropic dimensions of the 15-base pair duplexes (20Å in diameter vs. 60 Å in length), this thickness indicates that the helical axis is oriented ~45" from the gold surface. At applied voltages negative of the potential of zero charge, film thickness of ~60 Å are observed; more positive potential cause a drop in the film height to a limiting value of 20 Å at low surface coverages.

Based on the crossectional area of DNA (~3 $nm^2$) and the geometrical area of the gold electrodes (0.02 $cm^2$), the maximum surface coverage of DNA was calculated as ~6×$10^{-11}$ mol/$cm^2$. Coulometry at electrodes modified with duplexes containing crosslinked DM revealed a DM surface coverage of 7.5(7)×$10^{-11}$ mol/$cm^2$, indicating that the surface is densely packed with the modified duplexes. The DM value appeared to exceed slightly the theoretical Γ for DNA, and likely resulted from additional electrode surface roughness.

To assess routinely the surface coverage of DM-derivatized DNA on gold, the electrochemical response of $Fe(CN)_6^{4-}$ (2 mM) was monitored. This negatively charged ion is repelled from the modified-electrode surface by the polyanionic DNA, and exhibits essentially no response when the surface is well covered. While not a direct measure of surface coverage, this technique allowed the convenient assay of individual electrodes for adequate modification.

Cyclic voltammograms of these surfaces showed the reversible reduction of DM at −0.65 V versus SCE (Molinier-Jumel, 1978; Berg, 1981). These films were extremely stable and exhibited responses characteristic of surface-bound species (e.g., linear plots of peak current versus scan rate) (Bard, 1980).

Example 5

Measurement of Electrochemical Response of a Redox-Active Intercalator Crosslinked to a Fully Base-Paired DNA Duplex on a Gold Surface Integration of the electrochemical response yielded a surface coverage (Γ) of electroactive daunomycin of 7.5(7)× $10^{-11}$ mol/$cm^2$, a value in good agreement with the coverages of 15-base pair duplexes previously measured via $^{32}P$ labeling (Kelley, 1997a). However, significant fluctuations in the surface coverages of DM-modified duplexes were observed. Therefore, only electrodes which exhibited both large integrated currents for the reduction of crosslinked DM and an attenuated responses for the oxidation of ferrocyanide in solution were studied.

Given the 1:1 stoichiometry of crosslinked DM to DNA, the observed data indicated that all of the bound DM was electrochemically reduced. Doping these films with increasing percentages of DM-free duplexes resulted in a linear decrease in the observed electrochemical signals (as determined from coulometric assays), consistent with each of the bound intercalators being electrochemically active.

Figure 2A:
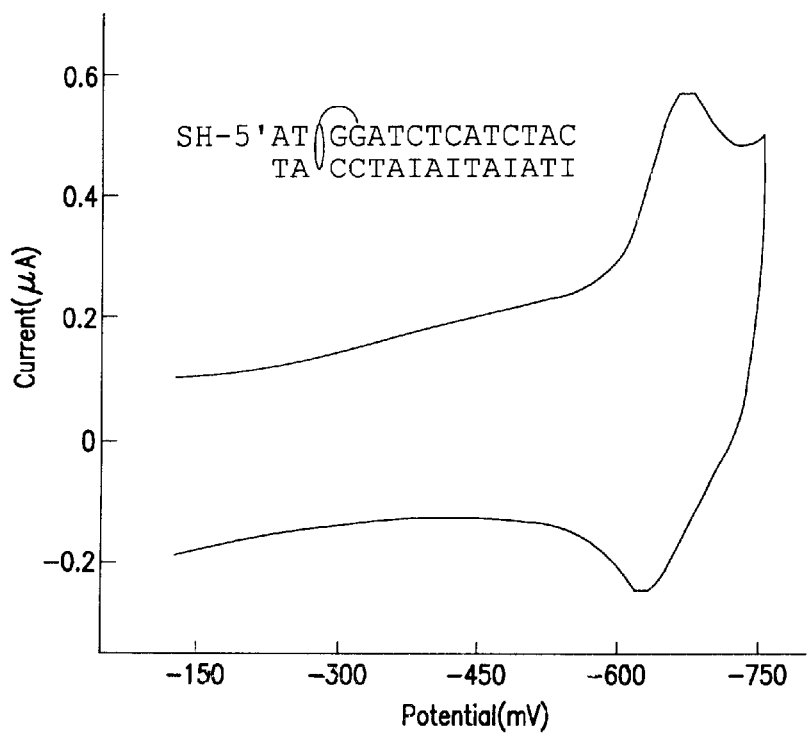
FIG. 2 illustrates cyclic voltammograms of gold electrodes modified with daunomycin-crosslinked thiol-terminated duplexes (A) SH-5'ATGGATCTCATCTAC+complement and (B) SH-5'ATCCTACTCATGGAC+complement, where the bold Gs represent the daunomycin crosslinking site.
Figure 2B:
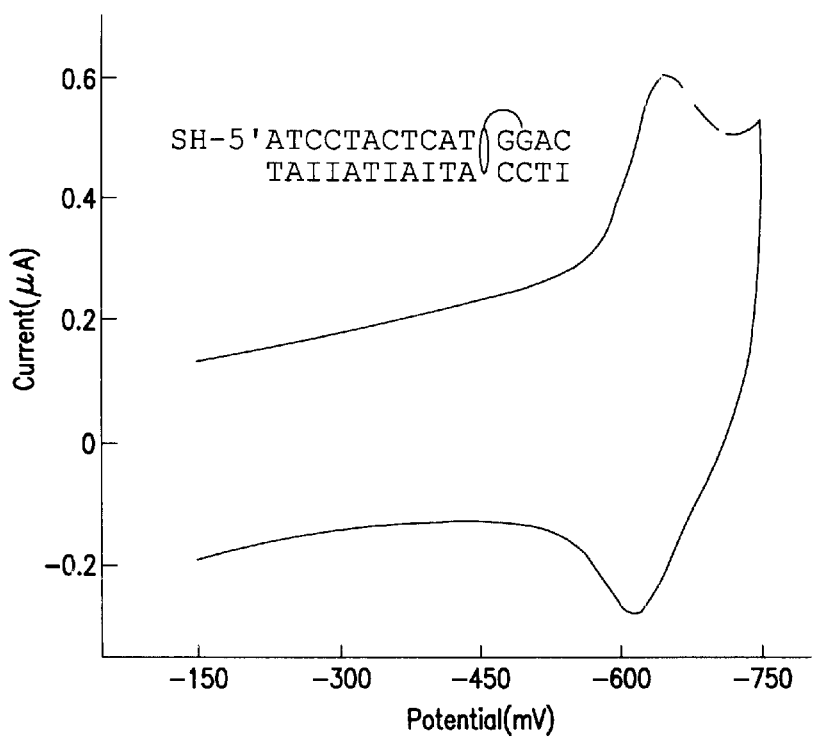

Remarkably, efficient reduction of DM was observed regardless of its position along the 15-base-pair sequence as illustrated in FIG. 2. Based on molecular modeling, the DM/gold separations span ~25 Å. The through-helix DM-electrode separation is >10 Å for DM bound at the end of the duplex closest to the electrode (FIG. 2A), and the DM-electrode separation is >35Å (FIG. 2B) for DM crosslinked to the end of the duplex farthest from the electrode. The surface coverage of electroactive daunomycin for these 15 base-pair duplexes as measured by integrating the currents within the illustrated voltammograms were $0.65 \times 10^{-10}$ mol/cm$^2$ and $0.80 \times 10^{-10}$ mol/cm$^2$, respectively. The DM:DNA stoichiometry for these same samples, measured by absorption spectroscopy were 0.9:1 and 1.1:1, respectively. Thus, the charge did not depend on distance, but did reflect the yield of crosslinking.

Example 6

Figure 3:
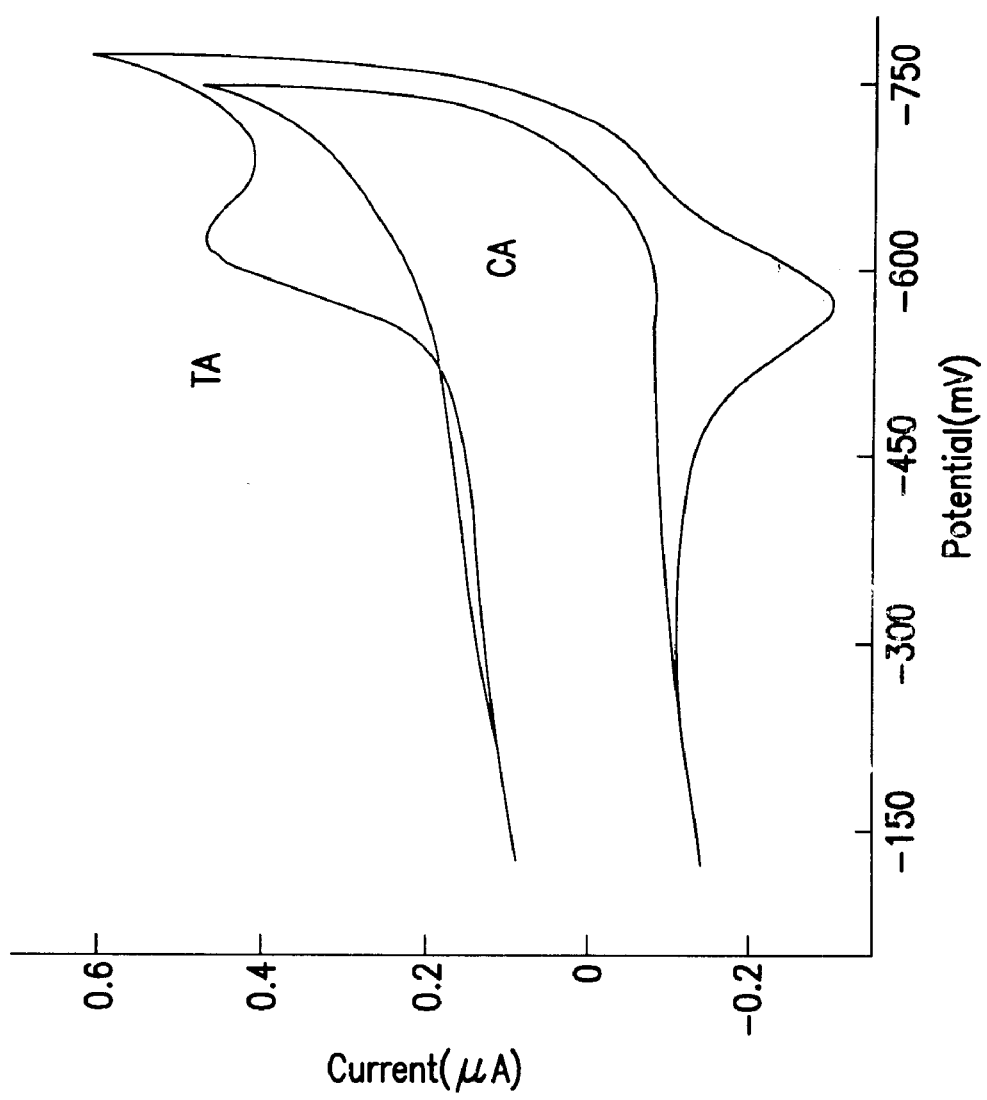
FIG. 3 illustrates cyclic voltammograms of gold electrodes modified with daunomycin-crosslinked thiol-terminated duplexes containing TA and CA basepairs. The oligonucleotide SH-5'ATTAT$\underline{A}$TAATTGCT was hybridized with the corresponding complements containing either a T or a C opposite from the underlined A (SEQ ID NO: 3).

Measurement of Electrochemical Response of a Redox-Active Intercalator Crosslinked to a Mismatch-Containing DNA Duplex on a Gold Surface Electrochemical responses of a redox-active intercalator crosslinked to a mismatch-containing DNA duplex on a gold surface were measured to determine whether these observed rates were a result of direct contact between the redox-active cofactor and the electrode surface (which has previously been shown to yield apparently distance-independent heterogeneous electron transfer (Feng, 1995, 1997)). A single site within the 15-base-pair duplex was mutated to produce a CA mismatch (known to cause local disruptions in the DNA base stack (Patel, 1984; Aboul-ela, 1985) between the intercalated DM and the electrode surface. FIG. 3 illustrates that such a simple change virtually eliminated the electrochemical response.

The coulometry of DM at electrodes modified with CA-containing duplexes varied to some degree as a function of the surface coverage. At high surface coverages (as determined by the ferrocyanide assay), essentially no signal was observed with the mismatched duplexes. However, at more moderate surface coverages, small signals corresponding to the reduction of DM were found. These typically did not exceed 30% of the signals found for the TA duplexes. The morphology of partial DNA monolayers is unknown.

Significantly, sequences in which the positions of the DM and CA mismatch were reversed (such that the mismatch was located above the DM relative to the gold) showed no diminution in the electrochemical response. AFM images of the CA-mutated sequences were identical to those of the TA analogs (monolayer thicknesses of ~40Å at open circuit), revealing that the bulk structure of the DNA films was not significantly altered by the presence of a mismatch. Moreover, the oxidation of ferrocyanide was similarly attenuated at both surfaces. Expected masses for DM-crosslinked DNA duplexes (accounting for the single base change) were measured by mass spectrometry, and spectrophotometric assays revealed that the extent of crosslinking was identical in both fully paired and mismatched sequences.

The exquisite sensitivity of the electrochemistry of DM to intervening lesions in the base stack provides therefore the basis for an exceptionally versatile DNA-mismatch sensor.

Example 7

Analysis of the Electrochemical Behavior of Fully Base-Paired or Mismatch-Containing DNA Duplexes Containing Non-Crosslinked Intercalators A practical method to detect mismatches utilizes a system based on non-crosslinked, intercalative, redox-active species. The electrochemistry of DM non-covalently intercalated into DNA-modified films was studied in order to develop a general approach to test heterogeneous sequences that may possess more than one guanine-binding site. Coulometric titrations confirmed that DM strongly binds to surfaces modified with fully base-paired duplexes, and yielded affinity constants very similar to those determined for homogeneous solutions (Arcamone, 1981; Molinier-Jumal, 1978; Berg, 1981). At bulk DM concentrations $\geq 1$ $\mu$M, the modified electrodes were saturated with intercalator, and hold approximately one intercalator per surface-confined duplex. Furthermore, intercalators non-covalently bound to these films exhibited electrochemical properties quite similar to those described for crosslinked DM, with the exception that the binding was reversible, i.e. in pure buffer solutions, decreasing voltammetric signals were observed until total dissociation was evident.

In accord with the studies of covalently bound DM, incorporation of a single CA mismatch into these duplexes dramatically decreased the electrochemical response (Table 1). The magnitude of this mismatch effect depended strongly on the location of the CA base step along the sequence: when the mutation was buried deep within the monolayer, the measured charge drops by a factor-of 3.5(5) (relative to the Watson-Crick duplex), but by only 2.3(4) when it was located near the solvent-exposed terminus. These observations were consistent with DM occupying sites near the top of the densely packed monolayer, as suggested in earlier studies of methylene blue bound to these same surfaces (Kelley, 1997b). The intensity of the electrochemical signals therefore not only reports the presence of the mismatch but also may describe the location of the disruption.

In addition, lateral charge diffusion within these monolayers was analyzed. For example, a series of fully base-paired films (sequence: SH-5'AGTACAGTCATCGCG) doped with increasing fractions of CA-mismatched helices were prepared (the mismatch was localized at the base step denoted by the bold C in the above sequence.) The coulometric response of DM non-covalently bound to these surfaces was strongly dependent on the film composition such that the electrochemical signals decreased linearly with increasing percentages of mutated duplexes. As there is no measurable difference in the affinities of DM toward TA-versus CA-containing films, this linear response indicated that the electroinactive intercalators (presumably those molecules bound to mutated helices) are not reduced by lateral charge transfer from the electroactive species. This result further supports a through-helix pathway for charge transduction, as intermolecular interactions between intercalators bound to different duplexes in the film evidently do not mediate efficient electron transfer.

Example 8

Analysis of Mutation Dependence of Electrochemical Response

To explore the scope of this mismatch detection strategy, the charge ($Q_c$) for DM at DNA-modified electrodes containing different single-base mismatches was analyzed (FIG.

4). The seven different mismatched duplexes were obtained by hybridization of the thiol-modified sequence, SH-5'AGTACAGTCATCGCG, with the following seven different complements (the mismatch is indicated in bold, and the specific basepair and the melting temperature of the duplex is given in parentheses):

5'CGCGATGACTGTACT (TA, $T_m$ = 68° C.),

5'CGCGACGACTGTACT (CA, $T_m$ = 56° C.),

5'CGCGATGTCTGTACT (TT, $T_m$ = 57° C.),

5'CGCGATCACTGTACT (CC, $T_m$ = 56° C.),

5'CGCGATGGCTGTACT (GT, $T_m$ = 62° C.),

5'CGCGATGAATGTACT (GA, $T_m$ = 60° C.),

5'CGCGATGCCTGTACT (CT, $T_m$ = 58° C.).

The charges were then calculated by integrating background-subtracted cyclic voltammograms. The obtained values were based on >5 trials, and the results were comparable for experiments run side-by-side or utilizing different sample preparations. The melting temperatures of the oligomers in solution were measured by monitoring duplex hypochromicity at 260 nm using samples that contained 10 $\mu$M duplex, 100 mM $MgCl_2$, and 100 mM phosphate at pH 7.

Coulometric analysis confirmed that the attenuation of the characteristic DM response was strongly dependent upon the identity of the mutation. In general, pyrimidine—pyrimidine and purine-pyrimidine mismatches caused marked decreases in the electrochemical signals; the one purine—purine pair studied (a GA mismatch, which is notoriously well-stacked within duplex DNA (Patel, 1984; Aboul-ela, 1985)) did not show a measurable effect. Surprisingly, a significant decrease was caused by a GT pair, which is also not highly disruptive to the helix. This wobble base pair, although thermodynamically stable, appears to mediate electron transfer poorly.

Figure 4:
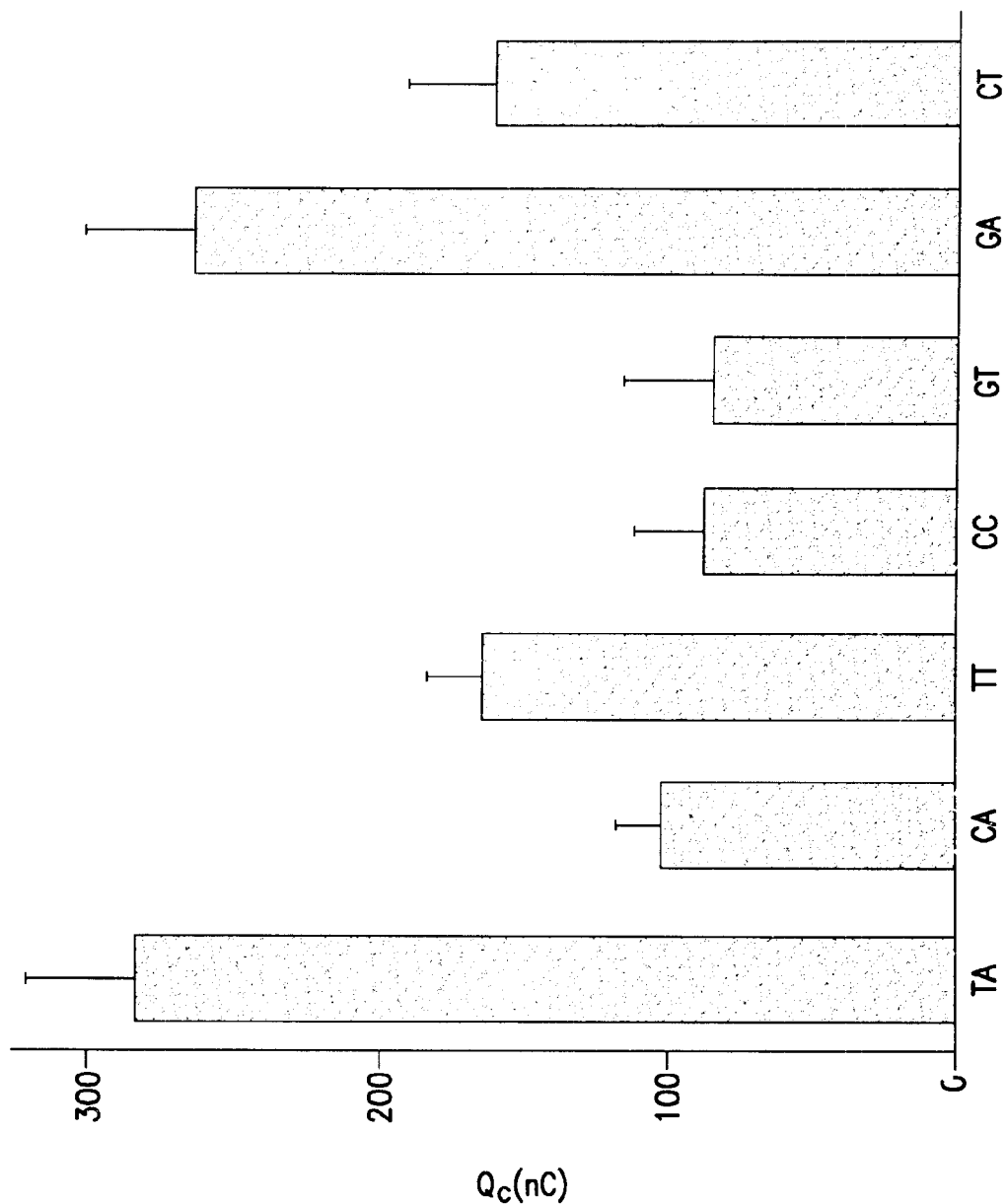
FIG. 4 describes the charges ($Q_c$) measured for daunomycin at DNA-modified electrodes containing different single-base mismatches. To obtain the seven different mismatched duplexes the thiol-modified sequence, SH-5'AGTACAGTCATCGCG, was hybridized with the following seven different complements (the mismatch is indicated in bold, and the specific basepair and the melting temperature of the duplex is given in parentheses)

FIG. 4 illustrates that across a very narrow range of duplex thermal stabilities, large differences in the electrochemical response were observed. Overall, the electrochemical properties of films containing the different mismatches correlated with the degree of disruption to base stacking with the individual duplexes. These results underscore the sensitivity of this electrochemical assay to base stacking within DNA, and demonstrate the viability of detecting mismatches based upon charge transduction through thin films.

Example 9

Analysis of Sequence Dependence of Mismatch Detection Assay

A single CA mismatch was incorporated into three different DNA duplexes to test for the sequence dependence of the assay. The duplexes featured varying percentages of GC content, representing a wide range of duplex stabilities. The melting temperatures for these duplexes, as determined by thermal denaturation measurements obtained by monitoring hypochromicity at 260 nm in duplex solutions containing 10 $\mu$M duplex, 100 mM phosphate, and 100 mM $MgCl_2$ were: (SH-5'-ATATAATATATGGAT): TA=47° C., CA=32° C.; (SH-5'AGTACACGTCATCGCG): TA=68° C., CA=56° C.; (SH-5'-GGCGCCCGGCGCCGG): GC=82° C., CA=69° C. The charge was quantitated from integrating background-subtracted cyclic voltammograms obtained at $\upsilon$=100 mV/s and was corrected for electrode area. As illustrated in FIG. 5, the characteristic drop in coulometric signals for DNA duplexes containing a single CA mismatch compared to fully base-paired DNA films was essentially invariant across AT-rich to GC-rich sequences. This sequence-independent response is not achievable using traditional mismatch detection assays based upon differential hybridization.

Example 10

Analysis of Electrochemical Response During Repeated Cycles

To extend this methodology to single-stranded targets, techniques for in situ hybridization were developed. Thiol-modified duplexes were deposited on the gold surface, heat denatured, thoroughly rinsed, then rehybridized with the desired target by incubation in $\geq$50 pmol of single-stranded oligonucleotide. The electrochemical properties of the resulting surfaces were identical to those described above, suggesting the suitability of this system for genomic testing.

For example, a 15-base-pair oligonucleotide, 5'AGTACAGTCATCGCG (SEQ ID NO: 4), which was derivatized with a thiol-terminated linker, was hybridized both to its native complement and to a mutated complement (at the site underlined in the sequence), generating a fully base-paired duplex and a CA mismatch-containing duplex, respectively (FIG. 6). These duplexes were deposited on separate electrodes and the electrochemical responses of DM non-covalently bound to these duplexes were measured using cyclic voltammetry (v=100 mV/s, 1.0 $\mu$M DM). FIG. 6 illustrates that DM exhibited electrochemical responses characteristic of fully base-paired and CA-mutated films, respectively. The surfaces were then denatured by immersing the electrodes in 90° C. pure buffer for 2 min to yield single-stranded monolayers of identical sequence. Cyclic voltammetry of DM at these electrodes now revealed nearly identical responses, with the reduction appearing highly irreversible, broadened, and becoming smaller as a function of increasing scans. Importantly, the electrode that initially possessed the CA mismatch displayed a large signal (for the first scan) after denaturation, while the reverse was true for the corresponding TA analog. New duplexes were formed by incubating the electrodes with 100 pmol of the opposite complement in the presence of buffered 100 mM $MgCl_2$ such that the complements were traded (TA→CA, CA→TA), and the electrochemistry at the duplex-modified films again showed the characteristic behavior expected for fully base-paired and CA-mutated films. Finally, the electrodes were again heated to denature the duplexes and quantitation of the response showed again the characteristics for single-stranded oligonucleoltides. Thus, electrodes can be cycled through this sequence of events repeatedly, indicating a practical means to detect point mutations within natural DNAs.

Example 11

Detection of Genetic Mutations Within a Specific Region of the p53 Gene Using Direct Current Measurement of Thiol-Modified Duplexes on Gold Surfaces A specific embodiment utilizes a gold-microelectrode array with approximately thirty addressable sites. A different 20-base pair duplex derivatized with a hexylthiol linker is attached to each of these sites by deposition form a concentrated duplex solution overnight. The sequences are chosen to correspond to the 600-base pair region within exons 5 through 8 of the p53 gene where most of the cancer-related mutations are found. The array is immersed in aqueous solution at 90° C. for 60 seconds to denature the immobilized duplexes and remove the complementary strands. The human sample containing the p53 gene is fragmented either before or after amplification. A solution containing the fragmented genomic single-stranded DNA is deposited on the array for one hour to allow hybridization to occur. Then, in the presence of a 1.0 μM DM solution, the charge passed at each of the electrodes is measured, and the response for each sequence is compared to that obtained from the wild-type (i.e. fully base-paired) sequences. Electrodes with attenuated signals correspond to mutated subsequences, while those which exhibited the expected charge are classified as unmutated.

Example 12

Detection of Mutations Using Electrocatalytic Currents Generated at DNA-Modified Surfaces The signals corresponding to mismatched and fully-paired sequences can be more highly differentiated by monitoring catalytic currents at DNA-modified surfaces. Electrons can be shuttled through the immobilized duplexes to redox-active intercalators localized on the solvent-exposed periphery of the monolayer, and then negatively-charged solution-borne species (which are electrostatically prohibited from the interior of the monolayer) are catalytically reduced by the intercalating mediators. Since the catalytic reaction essentially amplifies the signal corresponding to the intercalator, the attenuation of this response in the presence of the mismatch is significantly more pronounced. In a specific embodiment, the sequence SH-5'AGTACAGTCATCGCG (SEQ ID NO: 4) was deposited on an electrode both hybridized with a fully base-paired complement, and with a complement containing a CA mismatch (the position of the mismatch is denoted in bold). These duplexes were immersed in a solution containing 1.0 μM methylene blue and 1 mM ferricyanide. In the presence of either of these reagents alone, only small direct currents were measured. However, in the presence of a mixture of the intercalator and the negatively charged probe, pronounced currents were measured corresponding to the electrocatalytic reduction of ferricyanide by methylene blue. The amount of current observed for the TA and CA containing films differ dramatically; using electrocatalysis, the mismatched duplex can be differentiated from the fully base-paired duplexes by a factor of approximately 3. Moreover, as illustrated in FIG. 8, the peak potentials for the TA and CA duplexes are significantly separated, allowing the presence of the mismatch to be detected potentiometrically. This approach therefore represents an extremely sensitive means to detect genetic mutations electrochemically.

Example 13

Detection of Genetic Mutations Within a Specific Region of the p53 Gene Using Electrocatalytic Current Measurement of Thiol-Modified Duplexes on Gold Surfaces Another specific embodiment involves detecting the mutations within the p53 gene using electrocatalysis. A different 20-base pair duplex derivatized with a hexylthiol linker is attached to each of approximately thirty addressable sites of a gold-microelectrode array by deposition form a concentrated duplex solution overnight. The sequences are chosen to correspond to the 600-base pair region within exons 5 through 8 of the p53 gene where most of the cancer-related mutations are found. The array is immersed in aqueous solution at 90° C. for 60 seconds to denature the immobilized duplexes and remove the complementary strands. The human sample containing the p53 gene is fragmented either before or after amplification. A solution containing the fragmented genomic single-stranded DNA is deposited on the array for one hour to allow hybridization to occur. The array is rinsed and submerged in a solution containing 1.0 μM methylene blue and 1.0 mM ferricyanide. The pronounced currents that are observed result from the electrocatalytic reduction of the solution-borne ferricyanide by methylene blue adsorbed at the solvent-exposed duplex sites. These catalytic currents are measured for each addressable electrode and compared with those obtained with the wild-type sequence to detect potential sites of mutations.

Example 14

Detection of Genetic Mutations Within a Gene of Interest Using Direct or Electrocatalytic Current Measurement of Amine-Modified Duplexes on Carbon Surfaces Another embodiment utilizes a carbon electrode. The electrode is oxidized at +1.5 V (vs. Ag/AgCl) in the presence of $K_2Cr_2O_7$ and $HNO_3$, and treated with 1-[3-(dimethylamino)propyl]-3-ethylcarbodiimide hydrochloride (EDC) and N-hydroxysulfosuccinimide (NHS). Duplexes corresponding to mutated sequences of a specific gene of interest are derivatized with a hexylamine linker and applied to the electrode surface. The device is immersed in aqueous solution at 90 ° C for 60 seconds to, generate a single-stranded monolayer, and the fragmented genomic DNA sample is hybridized to the immobilized probes at room temperature for 1 hour. The detection of mutations is accomplished by (i) measuring direct currents in the presence of 1.0 μM daunomycin solution, or (ii) by measuring catalytic currents in the presence of 1.0 μM methylene blue and 1.0 mM ferricyanide. Charges passed at each electrode are measured, and the response for each sequence is compared to that obtained with wild-type, i.e. fully base-paired, sequences. Attenuated signals correspond to mutated subsequences, while those which exhibit no change in current are classified unmutated.

Although the invention has been described with reference to particular applications, the principles involved may be used in other applications which will be apparent to those skilled in the art. The invention is accordingly to be limited only by the scope of the claims which follow.

Example 15

Fabrication of DNA-Modified Films for Electrocatalysis

DNA-modified electrodes were prepared by derivatizing single-stranded oligonucleotides (typically 15-mers) at the 5' end with a thiol-terminated alkyl chain [$SH(CH_2)_2CONH(CH_2)_6NHCO$-DNA], herein referred to as SH-5'-DNA. The derivatized single-stranded oligonucleotides were hybridized to their unmodified complements. The ionic strength of the resulting duplex solution was increased with 100 mM $MgCl_2$ and a drop of this solution was placed on the gold surface. After 12–24 h, the electrodes were rinsed thoroughly with buffer and used for electrocatalytic studies.

Analyses by radioactive labeling and scanning-probe microscopy indicated that the duplexes formed densely packed monolayers (50 pmol/cm$^2$) oriented in an upright position with respect to the gold surface.

Less dense monolayers (~1 pmol/cm$^2$) were made using the above process, and of lowering the ionic strength of the buffer, decreasing the concentration of the SH-5'-DNA in the deposition solution, or shortening the deposition time.

After self-assembly, the exposed gold surface was passivated electrochemically by polymerization of 2-napthol in order to prevent direct association of the intercalative probe molecules with the electrode surface, so that electron transfer occurred only through electrode-bound duplexes.

Example 16

Detection of All Single Base Mismatches By Electrocatalytic Reduction of Methylene Blue In separate experiments, all possible single base mismatches were incorporated into DNA duplexes using SH-5'-AGTACAGTCATCGCG-3' (SEQ ID NO: 4). Electrode surfaces were modified with these duplexes and were interrogated using chronocoulometry (applied potential=–350 mV; 0.5 μM methylenie blue (MB$^+$); and 2.0 mM Fe(CN)$_6^{3-}$). The marked sensitivity of this assay is evidenced by the detection of all mismatches, including purine—purine mismatches, without any manipulation of experimental conditions (FIG. 10). Improved signal differentiation is achieved with increasing sampling time, a result that reflects the catalytic nature of this assay.

Mismatched duplexes are easily distinguished from canonical duplex DNA, but the mismatches cannot be readily distinguished from one another, as most yield approximately the same electrocatalytic response. Although GA and AA do yield electrocatalytic currents slightly higher than the other mismatches, these differences are not great in comparison to the overall attenuation in signal compared to fully matched sequences. Nonetheless, this methodology provides a clear strategy to detect a GA mismatch. GA mismatches have not been effectively detected using traditional methods owing to their high thermodynamic stability. In fact, even the repair machinery of the cell inefficiently recognizes the GA mismatch.

Indeed GA mismatches could not be detected significantly by DNA charge transport without using the electrocatalysis assay. Mismatches are generally stacked in a DNA duplex but undergo somewhat greater dynamical motion than well-paired bases. DNA charge transport detection, which depends upon the electronic coupling within the base stack, is sensitive to those motions; electrocatalysis allows for the amplification of this sensitivity.

Therefore, the electrocatalytic detection of mismatches relies not upon their thermodynamic stability but instead upon how well or poorly the mispair is electronically coupled into the base pair stack. This, in turn, affects how efficiently MB$^+$ can be reduced to generate active catalyst. The ability to detect single-base mismatches, irrespective of sequence, underscores the relevance of this method for mutational assays and genetic variability (SNPs).

Example 17

Single-Base Mismatch Detection in Sequences From the Human p53 Gene

The p53 tumor suppressor gene encodes a multifunctional transcription factor that plays a key role in the prevention of human cancer. Although tumor-inducing mutations have been observed at more than 100 sites in the p53 gene, more than 90% are found in regions that encode the DNA binding domain (residues 100–293). Of these, 25% occur at five "hot spots," in codons 175, 245, 248, 249, and 273. Hot spot mutations are separated into two categories, class I mutations that affect key residues at the DNA binding surface (e.g. Arg 248 and Arg 273) and class II mutations that affect residues responsible for holding the protein in a conformation that readily binds DNA (e.g. Arg 175 and Arg 249).

Two of these mutational hot spots, in codons 248 and 249, were chosen for initial examination using electrocatalysis. The mutation in codon 248 is a class I mutation caused by cigarette smoke that results in lung cancer and the 249 mutation is a class II mutation caused by Aflatoxin B1 exposure that results in liver cancer. The sequence SH-5'-ATGGGCCTCCGGTTC includes both of these hot spots and was synthesized with an alkanethiol linker at the 5' end. In separate samples, electrodes were modified with duplexes containing a CA mismatch at the boldface C (the common 248 mutation) or a CT mutation at the underlined C (the common 249 mutation). As evident in FIG. 11, both of these mismatches were successfully differentiated from the native duplex with electrocatalytic chronocoulometry at –350 mV with 0.5 M MB$^+$ and 2 mM Fe(CN)$_6^{3-}$.

It is therefore possible to detect mutations within natural sequences of double-stranded DNA using electrocatalysis. These methods should be fully transferable to other genes and sequences.

Example 18

Detection of Naturally Occurring DNA Lesions

The DNA in living cells is subject to spontaneous alteration as well as reaction with a variety of chemical compounds and physical agents present in the cell. For example, the deamination of cytosine gives rise to a CG to AT transition. Reactive oxygen species are generated through several pathways including mitochondrial leakage and ionizing radiation. 8-oxo-adenine is a possible oxidation product of DNA that results from the addition of a hydroxyl radical to the C8 position of the purine base. Hydroxy pyrimidines, such as 5,6-dihydroxy thymines, are another example of base damage products formed via the hydroxyl radical during the exposure of DNA to ionizing radiation.

Several of these possible DNA lesions were incorporated into the sequence SH-5'-AGTACAGTCATCGCG. Electrodes were modified (in separate samples) with double-stranded DNA sequences containing 8-oxo-adenine, 5,6-dihydro thymine, an abasic site, and deoxyuracil paired with guanine (the result of cytosine deamination). The films, once formed, were then examined by electrocatalysis at –350 mV with 0.5 M MB$^+$ and 2 mM Fe(CN)$_6^{3-}$. These lesions appeared to perturb electronic coupling within the DNA duplex. As a result, DNA mediated charge transport coupled to electrocatalysis was sensitive to those perturbations. Each lesion was successfully detected within the duplex DNA (FIG. 12).

Example 19

Sensitivity and Detection Limit of the Electrocatalytic Process With an Electrode Microarray An electrocatalysis assay was run with a gold microarray, consisting of 18 separately addressable gold electrodes ranging in size on a micron scale. As can be seen in FIG. 13, the total amount of charge accumulated after 5 seconds of electrocatalysis was found to be strictly proportional to the electrode area, down to electrodes as small as 30 µm or less in diameter.

Example 20

Sensitivity and Detection Limit of the Electrocatalytic Process With an Ultramicroelectrode Mismatch detection with sequences hybridized at the gold surface on the ultramicroelectrodes is also possible. The mismatched sequence after in situ hybridization was examined. As illustrated in FIG. 14, the electrodes on the chip were first modified with the well-matched sequence SH-5'-AGTACAGTCATCGCG (SEQ ID NO: 4) and investigated by electrocatalysis. Then they were gently washed with 90° C. buffer for 2 min followed by rinsing and incubation with a complement containing a single mismatch. Once fully hybridized, electrocatalysis was measured again and the accumulated charge was found to be characteristic of a mismatched DNA-monolayer.

The charge accumulated from the single-stranded monolayer on the ultramicroelectrodes was also examined. It is evident that electrocatalysis on the single-stranded monolayer results in charges similar to films with no mismatch. This is attributed to the fact that in a single-stranded monolayer (formed by denaturation of the double-stranded monolayer) the gold surface is more exposed. Thus $MB^+$ and ferricyanide are allowed access to the electrode for direct catalysis (not through DNA). Furthermore, the line shape for the single-stranded monolayer is different from double-stranded monolayers, which is consistent with a different mechanism for electrocatalysis (direct verses through DNA). The observations with single-stranded DNA also provided a control demonstrating that detection is not a measure of hybridization. Both double-stranded (with no mismatches) and single-stranded films yielded similar responses. In contrast, the mismatched complement, although fully hybridized, yielded an attenuated signal.

Example 21

Mismatch Detection in DNA/RNA Hybrids

In assays for interrogating cellular samples, it may be preferable to test mRNA transcripts rather than genomic DNA. In this scenario, patient mRNA was hybridized to a chip or electrode modified with single stranded DNA, resulting in DNA/RNA hybrids. The structure of such duplexes is a hybrid between A- and B-form nucleic acid, which results in different base stacking than in pure B-form DNA. Thus all single base mismatches within DNA/RNA hybrids were examined by electrocatalysis to ensure sensitivity to base stacking perturbations in this alternate duplex structure.

In separate experiments, all possible single-base mismatches were incorporated into DNA/RNA hybrids formed using SH-5'-AGTACAGTCATCGCG-3' (the surface-bound strand was DNA and the complements were RNA). Electrode surfaces modified with these duplexes were interrogated using chronocoulometry. As evident in FIG. 15, all possible mutations were detected readily. In fact, sensitivity to mutations was almost identical to the DNA/DNA results (FIG. 10). This means that when testing for mutations in clinical samples, genomic DNA, cDNA, or MRNA can be utilized, making electrocatalytic assays flexible and practical for routine use.

Example 22

Detection of Small Percentages of Mismatched Duplexes Within Wild-Type Films In order to investigate the ability of the electrocatalysis assay to detect small numbers of mismatched duplexes within a sea of fully Watson-Crick paired duplexes on a DNA film, monolayers were constructed in which the percentage of helices featuring a CA base step was varied between 0 and 100%. As illustrated in FIG. 16, using the appropriate experimental conditions (e.g., 0.2 µM $MB^+$ and 2 mM ferricyanide) the electrocatalytic signal decreases rapidly in a non-linear fashion as a function of the % CA duplexes in the film. Consequently, even small amounts of mismatched duplexes in the monolayer result in a pronounced decrease in the electrocatalytic response. Alternatively, using higher concentrations of $MB^+$ (e.g., 5 µM) a linear response occurs (FIG. 16). Such conditions may be useful in the detection of heterozygous genetic traits, in which half of the genes in a diploid organism carry the potentially harmful variation, and in the detection of somatic mutations as are associated with cancer.

Example 23

Comparison of CT of DNA-bound Electrodes Formed in the Presence and Absence of Mg2+

DNA-bound electrodes were formed in the presence of and in the absence of Mg2+. The two types of surfaces were characterized by scanning probe microscopy with chemically modified Si3N4 tips. Surfaces with bound 15 mer oligonucleotide duplexes formed in the presence of Mg2+ were found to produce smooth featureless films with a depth of 45 Å. However, images of DNA surfaces formed without Mg2+ were found to have a very different morphology. The images of DNA surfaces formed without Mg2+ were seen to have less ordered duplexes on the surface and the gold surface was visible in some areas. It was seen that without Mg2+, the duplexes were therefore significantly more loosely packed.

Square wave voltammograms obtained for the electrodes formed with and without Mg2+ showed a reversible reduction of DM at −580 mV versus Ag, and possessed features characteristic of surface-bound species. DNA adsorbed on Au(111) without Mg2+ in the self-assembly solution was quantitated in a 32P radioactive labeling experiment. The assay yielded an average surface coverage of 12 pmol/cm2 after 24 hours of modification, corresponding to a fractional coverage of 0.19. These values reflected a much lower surface coverage than previous studies with monolayers formed in the presence of high Mg2+ concentrations. The stoichiometry of crosslinked DM to DNA as being 1:1 was confirmed by UV-Vis spectroscopy and integration of the electrochemical signal. All data indicated that the crosslinked DM is electrochemically active.

Example 24

Detection of Base Flipping Due to Binding of Proteins on DM-DNA Modified Surfaces Chronocoulometry results for DM-DNA-modified surfaces in the absence and presence of different DNA-binding proteins are shown in FIG. 17. For the well-matched DNA duplex sequences tested, in the absence of bound protein, chronocoulometry at −575 mV (versus Ag) yielded a substantial signal upon integration over 5 sec. In the presence of some proteins, however, signal attenuation was observed, and this diminution in signal depended upon whether the protein structurally perturbed the DNA.

The protein-dependent changes are illustrated clearly for DNA films containing the methyltransferase HhaI (M.HhaI) target sequence in the presence and absence of M.HhaI. This enzyme catalyzes the methylation of cytosine in the sequence 5'-GCGC-3', and a M.HhaI-DNA co-crystal structure revealed that M.HhaI flips the cytosine out from the duplex and inserts glutamine 237 into the resulting space in the base stack. An electrode was prepared containing the duplex sequence SH-5'-AIAIATICICAIATCC(DM)T-3' (SEQ ID NO: 16) (protein binding site in boldface, DM binding site in italics). The methyl group source cofactor, S-adenosylmethionine, was omitted to test binding but not reaction on the electrode surface. As is evident in FIG. 18A, with M.HhtI bound to the DNA-modified electrode, the amount of charge passing through the film was greatly diminished. When BSA, a protein that does not bind DNA, was tested, no inhibition of current flow resulted. The diminution in current flow with M.HhaI can be understood based upon the interruption in the base pair stack as a result of base flipping and glutamine insertion by M.HhaI.

Also tested was a mutant M.HhaI, Q237W, that inserts instead an aromatic amino acid side chain, tryptophan, into the base pair stack upon base flipping. With binding of this mutant protein, and restoration of the π-stack, current flow was restored. Also, a small drop in charge was observed in the binding of the mutant enzyme but not with BSA (vide infra).

These results support previous observations made in solution, where CT was measured through studies of long range oxidative damage on DNA assemblies containing guanine doublets, as sites of oxidation, and a spatially separated rhodium photooxidant. Oxidative damage at the site distal to protein binding was substantially diminished in the presence of native M.HhaI but was restored in the presence of the Q237W mutant. Parallel results were obtained between these experiments irrespective of whether the reaction being monitored involved oxidation chemistry, with the rhodium photooxidant, or reduction chemistry, here with DM.

Example 25

Effects of Proteins on DM-DNA Modified Surfaces, Where the DNA Films Contained an Abasic Site in the Protein Binding Site Analogous results were also shown on DNA films containing an abasic site within the protein binding site (5'-GAbGC-3'). M.HhaI was seen to bind more tightly to the abasic substrate, but because of helix disruption, the presence of the abasic site without protein led to a diminution in integrated charge compared to the well-matched substrate. As can be seen in FIG. 18B, binding of the mutant protein with insertion of the Trp residue, however, completed the π-stack and restored current flow. Thus, the efficient DM reduction observed with Q237W cannot be explained by a loss of protein binding affinity.

Square wave voltammetry studies also yielded consistent results. Without protein or with Q237W bound to the film, a reversible peak was observed at −580 mV, the reduction potential of DM, but there was no peak with the wild type enzyme. Therefore only the base stack of DNA within protein-DNA complexes was able to be sensitively assayed.

Example 26

Detection of Base Flipping Due to Binding of Additional Proteins on DM-DNA Modified Surfaces Several other structurally well characterized protein-DNA complexes were also probed. Uracil-DNA glycosylase, is a base flipping enzyme important to base excision repair. The Au electrode surface was modified with the sequence SH-5'-AICTIAATCAITCC(DM)T-3' with a 2'-fluoro-uracil, to prevent enzyme turnover, incorporated onto the complementary strand opposite the boldface A. After backfilling with mercaptohexanol and incubation with 1 μM UDG, the surface was interrogated at −575 mV by chronocoulometry (FIG. 18C). Again, very little charge was transported through this protein-DNA complex. This result further supported the structural model, where base flipping by uracil DNA glycosylase perturbs base stacking and hence current flow to DM.

Example 27

Detection of Perturbations to the Base Stack of a DM-DNA Modified Duplex

The assay also provided a measurement of current flow associated with perturbations to the base stack, in addition to base flipping. The TATA-box binding protein (TBP), for example, kinked DNA approximately 90° upon binding to its target site, completely disrupting base stacking but not base pairing. Binding of TBP to its recognition site was examined on electrodes modified with the sequence SH-5'-IAIATATAAAICACC(DM)T-3' (SEQ ID NO: 18) and mercaptohexanol. As evident in FIG. 18D, with protein binding (1 μM), the ability to reduce DM through DNA-mediated CT was significantly diminished.

DNA binding by the restriction endonuclease PvuII (R.PvuII) at a surface modified SH-5'-TCTTCAIMTIAIA CC(DM)T-3' (SEQ ID NO: 19), passivated with mercaptohexanol, and incubated with 1 μM enzyme was also investigated. A methylated cytosine (M) was incorporated to prevent cleavage of the DNA film during the electrochemical investigation. As predicted from the presence or absence of even this small change in chronocoulometry is indicative of protein binding. This was also seen in M.HhaI binding to an electrode modified with PvuII DNA (FIG. 18F). Here, M.HhaI was bound to the surface but did not base flip because there was no 5'-GCGC-3' site. BSA, on the other hand, did not bind to DNA and thus no drop in charge was observed.

Example 28

Use of CT for Electrical Probes of Enzyme Reaction Kinetics

It was also tested whether this assay might be amenable to electrical probes of DNA enzyme reaction kinetics (FIG. 19). The restriction activity of PvuII (1 μM) was assayed on the Au surface modified with SH-5'-TCTTCAICTIAIACC (DM)T-3' (SEQ ID NO: 20), but with the native non-methylated restriction site incorporated into the monolayer to monitor endonuclease activity. As the enzyme cuts the DNA, the DM probe is released from the surface resulting in a diminution in CT in the film. Indeed, the amount of charge accumulated at this surface after five seconds of chronocoulcmetry decreased with increasing reaction time while the amount of DM reduction in an identical surface without protein remained constant. The decrease in charge is exponential as expected for the kinetics of PvuII. Furthermore, the electrochemical data agree with a gel based cleavage assay performed under the electrochemical conditions. DNA-modified films may therefore be employed also in electrical monitoring of DNA enzymatic reactions.

REFERENCES

Aboul-ela, F., Koh, D., Tinoco, I., Martin, F. H. (1985) *Nucl. Acids Res.* 13: 4811.

Akashi et al. (1992) *Bioconjugate Chem.* 3: 363.

Alivisatos, A. P., Johnsson, K. P., Peng, X. G., Wilson, T. E., Loweth, C. J., Bruchez, M. P., Schultz, P. G. (1996) *Nature* 382: 609.

Arcamone, F. *Doxorubicin: Anticancer Antibiotics*, Academic Press, New York (1981).

Arkin, M. R., Stemp, E. D. A., Barton, J. K. (1997) *Chem. and Biol.* 4: 389.

Bard A. J. and Faulkner, L. R. *Electrochemical Methods*, Wiley and Sons, New York (1980).

Beratan, D. N., Priyadarshy, S., Risser S. M. (1997) *Chem. and Biol.* 4: 3.

Berg, H., Horn, G., Luthardt, U. (1981) *Biolectrochem. Bioenerg.* 8: 537.

Boon, E. M., Kisko, J. K. & Barton, J. K. Detection of DNA base mismatches using DNA intercalators. *Methods in Enyzmology*, submitted.

Boon, E. M., Ceres, D. M., Drummond, T. G., Hill, M. G. & and Barton, J. K. Mutation detection by electrocatalysis at DNA-modified electrodes. *Nature Biotechnology* 18, 1096–1100 (2000).

Bos (1989) *Canc. Res.* 49: 4682.

Brun A. M. and Harriman A. (1992) *J. Am. Chem. Soc.* 114: 3656.

Carter, M. T. et al. (1989) *J. Am. Chem. Soc.* 111: 8901.

Carter, M. T. et al. (1990) Biocnjugate Chem. 1: 257.

Chee, M., Yang, R., Hubbell, E., Bemo, A., Huang, X. C., Stem, D., Winkler, J., Lockhard, D. J., Morris, M. S., Fodor, S.P.A. (1996) *Science* 274:610–614.

Cheng, X., Kumar, S., Posfai, J. Pflugrath, J. W. & Roberts, R. J. Crystal-structure of the HhaI DNA methyltransferase complexed with S-adenosyl-L-methionine. *Cell* 74, 2199–307 (1993). 299.

Cheng, X., Balendiran, K., Schildkraut, I. & Anderson, J. E. Structure of PvuII endonuclease with cognate DNA. *EMBO J.* 13, 3927–3935 (1994).

Dandliker, P. J., Homlin, R. E., Barton, J. K. (1997) Science 275: 1465.

Drmanac, R., Drnanac, S., Strezoska, Z., Paunesku, T., Labat, I., Zeremski, M., Snoddy, J., Funkhouser, W. K., Koop, B., Hood, L. et al. (1993) Science 260:1649–1652.

Elghanian, R., Storhoff, J. J., Mucic, R. C., Letsinger, R. L., Mirkin, C. A. (1997) Science 277: 1078.

Eng, C. and Vijg, J. (1997) Nat. Biotech. 15: 422.

Feng, Z. Q., Imabayashi, S., Kakiuchi, T., Niki, K. (1995) J. Electroanal. Chem. 394:149.

Feng, Z. Q., Imabayashi, S., Kakiuchi, T., Niki, K. (1997) J. Chem. Soc. Faraday Trans. 93: 1367.

Garcia, R. A., Bustamante, C. J. & Reich, N. O. Sequence-specific recognition by cytosine C-5 and adenine N-6 DNA methyltransferases requires different deformations of DNA. P. Natl. Acad. Sci. USA 93, 7618–7622 (1996).

Hacia, J. G., Brody, L. C., Chee, M. S., Fodor, S. P., Collins, F. S. (1996) Nat. Genet. 14:441–447.

Hall, D. B., Homlin, R. E., Barton, J. K. (1996) Nature 382: 731.

Hall D. B. and Barton, J. K. (1997) J. Am. Chem. Soc. 119: 5045.

Harrison J. G. and Balasubramanian, S. (1997) Bioorg. Med. Chem. Lett. 7: 1041.

Hashimoto, K. et al. (1994a) Anal. Chem. 66: 3830.

Hashimoto, K. et al. (1994b) Anal. Chim. Acta 286: 219.

Herne, T. M. & Tarlov, M. J. Characterization of DNA probes immobilized on gold surfaces. J. Am. Chem. Soc. 119, 8916–8920 (1997).

Homlin, R. E., Dandliker, P. J., Barton, J. K. (1997) Angew. Chem. Int. Ed., in press.

Innis et al. (1990) PCR Protocols: A Guide to Methods and Applications, Academic Press, San Diego.

Jackson, B. A. and Barton, J. K. (1997) J. Am. Chem. Soc. 119: 12986–12987.

Johnston, D. H. et al. (1995) J. Am. Chem. Soc. 117: 8933.

Johnston, P. J. & Bryant, P. E. Lack of interference of DNA single-strand breaks with the measurement of double-strand breaks in mammalian-cells using the neutral filter elution assay. Nucleic Acids Res. 19, 2735–2738 (1991).

Kelley, S. O., Jackson, N. M., Barton, J. K. & Hill, M. G. Electrochemistry of methylene blue bound to a DNA-modified electrode. Bioconjug. Chem. 8, 31–37 (1997).

Kelley, S. O., Barton, J. K., Jackson, N. M., McPherson, L., Potter, A., Spain, E. M., Allen, M. J., Hill, M. G., submitted (1997b)

Kelley, S. O., Holmlin, R. E., Stemp, E. D. A. & Barton, J. K. Photoinduced electron transfer in ethidium-modified DNA duplexes—dependence on distance and base stacking. J. Am. Chem. Soc. 119, 9861–9870 (1997).

Kelley S. O. and Barton, J. K. submitted (1997d).

Kelley, S. O., Jackson, N. M., Hill, M. G. & Barton, J. K. Long-range electron transfer through DNA films. Angew. Chem. Int. Ed. Eng. 38, 941–945 (1998).

Kelley, S. O., Boon, E. M., Jackson, N. M., Hill, M. G. & Barton, J. K. Single-base mismatch detection based on charge transduction through DNA. Nucleic Acids Res. 27, 4830–4837 (1999).

Kelley, S. O. & Barton, J. K. Radical migration through the DNA helix: Chemistry at a distance. Metal Ions in Biologial Systems 36, 211–249 (1999).

Kelley, S. O., et al. Orienting DNA helices on gold using applied electric fields. Langmuir 14, 6781–6784 (1998).

Kelly, J. M. et al. (1986) In: Electrochemistry, Sensors, and Analysis, eds. Smyth, M. R. and Vos, J. G., Elsevier, Amsterdam, pp. 205.

Kim, J. L., Nikolov, D. B. & Burley, S. K. Co-crystal structure of TBP recognizing the minor-groove of a TATA element. Nature 365, 520–527 (1993).

Kim, Y., Geiger, J. H., Hahn, S. & Sigler, P. B. Crystal-structure of a yeast TBP TATA-box complex. Nature 365, 512–520 (1993).

Kobayashi, H. Horton, E. L., Brown, (1996) Nat. Biotech. 14: 1675.

Kojic-Prodic, B., & Kroon, J. (Bio)crystallography at the turn of the millennium. Croat. Chem. Acta 74,1–35 (2001).

Korriyoussoufi, H., Gamier, F., Srivastava, P., Godillot, A., Yassar, (1997) J. Am. Chem. Soc. 119: 7388.

Lamture et al. (1994) Nucl. Acids Res. 22: 2121.

Landegren et. al. (1988) Science 241: 1077.

Leng, F., Savkur, R., Fokt, I., Prewloka, T., Priebe, W., Chaires, J. B. (1996) J. Am. Chem. Soc. 118: 4732.

Lewis, F. D., Wu, T., Zhang, Y., Lestsinger, R. L., Greenfield, S. R., Wasielewski M. R. (1997) Science 277: 673.

Lin, S. V. -Y., Motesharei, K., Dancil, K. -P. S., Sailor, M. J., Ghadiri, M. R. (1997) Science 278: 840.

Lipshutz, R. J., Morris, D., Chee, M., Hubbell, E., Kozal, M. J., Shah, N., Shen, N., Yang, R., Fodor, S. P. (1995) Biotechniques 19:442–447.

Maeda, M. et al. (1992) Anal. Sci. 8: 83.

Maeda, M. et al.(1994) Chem. Lett. 1805.

Marcus R. A. and Sutin N. (1985) Biochim. Biophys. Acta 811: 265.

Maxam and Gilbert (1980) Meth. Enz. 65:499–560.

Meade, T. J. and Kayyem, J. F. (1995) Angew. Chem. Int. Ed. Engl. 34: 352.

Mi., S., Alonso, D. & Roberts, R. J. Functional-analysis of gln-237 mutants of HhaI methyltransferase. Nucleic Acids Res. 23, 620–627 (1995).

Millan, K. M. and Mikkelsen, S. R. (1993) Anal. Chem. 65: 2317.

Mvlolinier-Jumel, C., Malfoy, B., Reynaud, J. A., Aubel-Sadron, G (1978). Biochem. Biophys. Res. Comm. 84: 441.

Mui, S., Boon, E. M., Hill, M. G., Barton, J. K., & Spain, E. M. Morphology of 15-mer duplexes tethered to Au(111) probed using scanning probe microscopy. Langmuir, submitted.

Murphy, C. J., Arkin; M. A., Jenkins, Y., Ghatlia, N. D., Bossman, S., Turro, N. J., Barton, J. K. (1993) Science 262: 1025.

Nahir, T. M., Clark, R. A., Bowden, E. F. (1994) Anal. Chem. 66: 2595.

Netzel T. L. J. (1997) Chem. Educ. 74: 646.

Nunez, M. E. & Barton, J. K. Probing DNA charge transport with metallointercalators. Current Opinion in Chemical Biology 4, 199–206 (2000).

O'Gara, M., Klimasauskas, S., Robers, R. J. & Cheng, X. D. Enzymatic C5-cytosine methylation of DNA: Mechanistic implications of new crystal structures for HhaI methyltransferase-DNA-AdoHcy complexes. J. Mol. Biol. 261, 634–645 (1996).

O'Gara, M., Horton, J. R., Roberts, R. J. & Cheng, X. Structures of HhaI methyltransferase complexed with substrates containing mismatches at the target base. Nature Sructural Biology 5, 872–877 (1998).

Okahata, J. et al. (1992) J. Am. Chem. Soc. 114: 8300.

Patel, D. J., Kozlowski, S. A., Ikuta, S., Itakura, K. (1984) FASEB 11: 2664.

Plambeek, J. and Lown, J. W. (1984) J. Electrochem. Soc. 131: 2556.

Priyadarshy, S., Risser, S. M., Beratan, D. N. (1996) J. Phys. Chem. 100: 17678.

Rajski, S. R. & Barton, J. K. How different DNA-binding proteins affect long-range oxidative damage to DNA. Biochemistry 40, 5556–5564 (2001).

Rajski, S. R. & Barton, J. K. DNA-mediated electron transfer: A sensitive probe of DNA-protein interactions. Journal of Biomolecular Structure & Dynamics S2, 285–291 (2000).

Rajski, S. R., Kumar, S. R., Roberts, R. J., & Barton, J. K. Protein-modulated DNA electron transfer. J. Am. Chem. Soc. 121, 5615–5616 (1999).

Riddles, P. W., Blakeley, R. L., Zerner, B. (1979) Anal. Biochem, 94: 75.

Rodriguez, M. and Bard, A. J. (1990) Anal. Chem. 62: 2658.

Saiki et al. (1985) Science 230: 1350.

Sanger et al. (1977) Proc. Natl. Acad. Sci. 74: 5463.

Scharf (1986) Science 233: 1076.

Skogerboe, K. J. (1993) Anal. Chem. 65: 416R.

Slupphaug, G., et al. A nucleotide-flipping mechanism from the structure of human uracil-DNA glycosylase bound to DNA. Nature 384, 87–92 (1996).

Southern, E. M. (1996) Trends in Genetics 12: 110.

Stivers, J. T., Pankiewicz, K. W. & Watanabe, K. A. Kinetic mechanism of damage site recognition and uracil flipping by Escherichia coli uracil DNA glycosylase. Biochemistry 38, 952–963 (1999).

Szent-Györgyi, A. (1941) Nature 148: 157.

Tender, L., Carter, M. T., Murray, R. W. (1994) Anal. Chem. 66: 3173.

Wachter, L., Jablonski, J. A., Ramachandran, K. L. (1986) Nucl. Acids Res. 14: 7985.

Wagenknecht, H. A., Rajski, S. R., Pascaly, M., Stemp, E. D. A., & Barton, J. K. Direct observation of radical intermediates in protein-dependent DNA charge transport. J. Am. Chem. Soc. 123, 4400–4407 (2001).

Wang, A. H. -J., Gao, Y. -G., Liaw, Y. C., Li, Y. K. (1991) Biochemistry 30: 3812.

Warman, J. M., de Haas, M. P., Rupprecht, A. (1996) Chem. Phys. Lett. 249: 319.

Weber, K., Creager, S. E. (1994) Anal. Chem. 66: 3164.

Welch, T. W. et al. (1995) J. Phys. Chem. 99 11757.

Widrig, C. A., Alves, C. A., Porter, M. D. (1991) J. Am. Chem. Soc. 113: 2805.

Wu, D. Y. et al. (1989a). Genomics 4:560–569.

Xu, X. -H. et al. (1994) J. Am. Chem. Soc. 116: 8386.

Xu, X. -H. and Bard, A. J. (1995) J. Am. Chem. Soc. 117: 2627.

Zei, M. S., Nakai, Y., Lehmpfuhl, G., Kolb, D. M. (1983) J. Electroanal. Chem. 150: 201.

While the invention has been described in detail with reference to certain preferred embodiments thereof, it will be understood that modifications and variations are within the spirit and scope of that which is described and claimed.

SEQUENCE LISTING

```
<160> NUMBER OF SEQ ID NOS: 31

<210> SEQ ID NO 1
<211> LENGTH: 15
<212> TYPE: DNA
<213> ORGANISM: Artificial Sequence
<220> FEATURE:
<223> OTHER INFORMATION: Oligonucleotide probe
```

<400> SEQUENCE: 1
atggatctca tctac                                                    15

<210> SEQ ID NO 2
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 2
atcctactca tggac                                                    15

<210> SEQ ID NO 3
<211> LENGTH: 14
<212> TYPE: DNA
<213> ORGANISM: Artificial Sequence
<220> FEATURE:
<223> OTHER INFORMATION: Oligonucleotide probe

<400> SEQUENCE: 3
attatataat tgct                                                     14

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 4
agtacagtca tcgcg                                                    15

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 5
cgcgatgact gtact                                                    15

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 6
cgcgacgact gtact                                                    15

<210> SEQ ID NO 7
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 7
cgcgatgtct gtact                                                    15

```
<210> SEQ ID NO 8
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 8
cgcgatcact gtact                                                        15

<210> SEQ ID NO 9
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 9
cgcgatggct gtact                                                        15

<210> SEQ ID NO 10
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 10
cgcgatgaat gtact                                                        15

<210> SEQ ID NO 11
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 11
cgcgatgcct gtact                                                        15

<210> SEQ ID NO 12
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 12
atataatata tggat                                                        15

<210> SEQ ID NO 13
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 13
agtacagtca tcgcg                                                        15

<210> SEQ ID NO 14
<211> LENGTH: 15
<212> TYPE: DNA
<213> ORGANISM: Artificial Sequence
<220> FEATURE:
```

<223> OTHER INFORMATION: Oligonucleotide probe

<400> SEQUENCE: 14
ggcgcccggc gccgg                                                        15

<210> SEQ ID NO 15
<211> LENGTH: 15
<212> TYPE: DNA
<213> ORGANISM: Artificial sequence
<220> FEATURE:
<223> OTHER INFORMATION: Oligonucleotide probe

<400> SEQUENCE: 15
atgggcctcc ggttc                                                        15

<210> SEQ ID NO 16
<211> LENGTH: 17
<212> TYPE: DNA
<213> ORGANISM: Artificial sequence
<220> FEATURE:
<223> OTHER INFORMATION: Oligonucleotide probe
<221> NAME/KEY: misc_feature
<222> LOCATION: (1)..(17)
<223> OTHER INFORMATION: n is inosine (I)

<400> SEQUENCE: 16
ananatncnc anatcct                                                      17

<210> SEQ ID NO 17
<211> LENGTH: 15
<212> TYPE: DNA
<213> ORGANISM: Artificial sequence
<220> FEATURE:
<223> OTHER INFORMATION: Oligonucleotide probe
<221> NAME/KEY: misc_feature
<222> LOCATION: (1)..(15)
<223> OTHER INFORMATION: n is inosine (I)

<400> SEQUENCE: 17
anctnaatca ntcct                                                        15

<210> SEQ ID NO 18
<211> LENGTH: 16
<212> TYPE: DNA
<213> ORGANISM: Artificial sequence
<220> FEATURE:
<223> OTHER INFORMATION: Oligonucleotide probe
<221> NAME/KEY: misc_feature
<222> LOCATION: (1)..(16)
<223> OTHER INFORMATION: n is inosine (I)

<400> SEQUENCE: 18
nanatataaa ncacct                                                       16

<210> SEQ ID NO 19
<211> LENGTH: 16
<212> TYPE: DNA
<213> ORGANISM: Artificial sequence
<220> FEATURE:
<223> OTHER INFORMATION: Oligonucleotide probe
<221> NAME/KEY: misc_feature
<222> LOCATION: (1)..(16)
<223> OTHER INFORMATION: n is inosine (I)
<221> NAME/KEY: misc_feature
<222> LOCATION: (8)..(8)
<223> OTHER INFORMATION: n is Methylated cytosine

<400> SEQUENCE: 19
tcttcanntn anacct                                                16

<210> SEQ ID NO 20
<211> LENGTH: 16
<212> TYPE: DNA
<213> ORGANISM: Artificial sequence
<220> FEATURE:
<223> OTHER INFORMATION: Oligonucleotide probe
<221> NAME/KEY: misc_feature
<222> LOCATION: (1)..(16)
<223> OTHER INFORMATION: n is inosine (I)

<400> SEQUENCE: 20
tcttcanctn anacct                                                16

<210> SEQ ID NO 21
<211> LENGTH: 15
<212> TYPE: DNA
<213> ORGANISM: Artificial Sequence
<220> FEATURE:
<223> OTHER INFORMATION: Complement of SEQ ID NO:1
<221> NAME/KEY: misc_feature
<222> LOCATION: (1)..(15)
<223> OTHER INFORMATION: n is inosine (I)

<400> SEQUENCE: 21
tacctanant anatn                                                 15

<210> SEQ ID NO 22
<211> LENGTH: 15
<212> TYPE: DNA
<213> ORGANISM: Artificial Sequence
<220> FEATURE:
<223> OTHER INFORMATION: Complement of SEQ ID NO:2
<221> NAME/KEY: misc_feature
<222> LOCATION: (1)..(15)
<223> OTHER INFORMATION: n is inosine (I)

<400> SEQUENCE: 22
tannatnant acctn                                                 15

<210> SEQ ID NO 23
<211> LENGTH: 17
<212> TYPE: DNA
<213> ORGANISM: Artificial sequence
<220> FEATURE:
<223> OTHER INFORMATION: Complement of SEQ ID NO:16
<221> NAME/KEY: misc_feature
<222> LOCATION: (1)..(17)
<223> OTHER INFORMATION: n is inosine (I)

<400> SEQUENCE: 23
tctctacncn tctagga                                               17

<210> SEQ ID NO 24
<211> LENGTH: 16
<212> TYPE: DNA
<213> ORGANISM: Artificial sequence
<220> FEATURE:
<223> OTHER INFORMATION: Oligonucloetide probe
<221> NAME/KEY: misc_feature
<222> LOCATION: (9)..(9)
<223> OTHER INFORMATION: n is inosine (I)

<400> SEQUENCE: 24
tctctaccnt ctagga                                                16

<210> SEQ ID NO 25
<211> LENGTH: 15
<212> TYPE: DNA
<213> ORGANISM: Artificial sequence
<220> FEATURE:
<223> OTHER INFORMATION: Complement of SEQ ID NO:17
<221> NAME/KEY: misc_feature
<222> LOCATION: (1)..(15)
<223> OTHER INFORMATION: n is inosine (I)

<400> SEQUENCE: 25
tcnactuant cagga                                                    15

<210> SEQ ID NO 26
<211> LENGTH: 16
<212> TYPE: DNA
<213> ORGANISM: Artificial sequence
<220> FEATURE:
<223> OTHER INFORMATION: Complement of SEQ ID NO:18
<221> NAME/KEY: misc_feature
<222> LOCATION: (1)..(16)
<223> OTHER INFORMATION: n is inosine (I)

<400> SEQUENCE: 26
ctctatattt cntgga                                                   16

<210> SEQ ID NO 27
<211> LENGTH: 16
<212> TYPE: DNA
<213> ORGANISM: Artificial sequence
<220> FEATURE:
<223> OTHER INFORMATION: Oligonucleotide probe
<221> NAME/KEY: misc_feature
<222> LOCATION: (1)..(16)
<223> OTHER INFORMATION: n is inosine (I)
<221> NAME/KEY: misc_feature
<222> LOCATION: (7)..(7)
<223> OTHER INFORMATION: n is Methylated cytosine

<400> SEQUENCE: 27
anaantnnac tctgga                                                   16

<210> SEQ ID NO 28
<211> LENGTH: 16
<212> TYPE: DNA
<213> ORGANISM: Artificial sequence
<220> FEATURE:
<223> OTHER INFORMATION: Complement of SEQ ID NO:20
<221> NAME/KEY: misc_feature
<222> LOCATION: (1)..(16)
<223> OTHER INFORMATION: n is inosine (I)

<400> SEQUENCE: 28
anaantcnac tctgga                                                   16

<210> SEQ ID NO 29
<211> LENGTH: 15
<212> TYPE: DNA
<213> ORGANISM: Artificial sequence
<220> FEATURE:
<223> OTHER INFORMATION: Complement of SEQ ID NO:12

<400> SEQUENCE: 29
tatatyatat accta                                                    15

<210> SEQ ID NO 30
<211> LENGTH: 15

```
<212> TYPE: DNA
<213> ORGANISM: Artificial sequence
<220> FEATURE:
<223> OTHER INFORMATION: Complement of SEQ ID NO:4

<400> SEQUENCE: 30
tcatgtcagy agcgc                                                        15

<210> SEQ ID NO 31
<211> LENGTH: 15
<212> TYPE: DNA
<213> ORGANISM: Artificial sequence
<220> FEATURE:
<223> OTHER INFORMATION: Complement of SEQ ID NO:14

<400> SEQUENCE: 31
ccgcrggccg cggcc                                                        15
```

What is claimed is:

1. A method of detecting one or more single-base sequence lesions in a target nucleic acid sequence, comprising:
   a) contacting a first single stranded nucleic acid probe sequence with a second single stranded nucleic acid target sequence to form a duplex, wherein the second single stranded nucleic acid target sequence is hybridized to a monolayer of first single stranded nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in the target sequence.

2. The method of claim 1, wherein the first single stranded nucleic acid probe sequence contains a thiol terminated 5' end.

3. The method of claim 2, wherein the thiol-terminated 5' end is a thiol terminated alkyl chain.

4. The method of claim 1, wherein the second single stranded nucleic acid target sequence is DNA.

5. The method of claim 1, wherein the second single stranded nucleic acid target sequence is RNA.

6. The method of claim 1, wherein the intercalative, redox-active moiety is methylene blue.

7. The method of claim 1, wherein the non-intercalative, redox-active moiety is ferricyanide.

8. A method of detecting one or more single-base sequence lesions in a target nucleic acid sequence, comprising:
   a) contacting a first single stranded, derivatized nucleic acid probe sequence with a second single stranded nucleic acid target sequence to form a duplex, wherein the second single stranded nucleic acid target sequence is hybridized to a monolayer of first single stranded derivatized nucleic acid probe sequences on an electrode, wherein the monolayer is prepared by first attaching a duplex comprising the first single stranded, derivatized nucleic acid probe sequence to the electrode, and dehybridizing the duplex, such that the first single stranded, derivatized nucleic acid probe sequence remains attached to the electrode, and wherein the hybrid of the first single stranded, derivatized nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in the target sequence.

9. The method of claim 8, wherein the derivatized nucleic acid probe sequence is an oligonucleotide with a thiol-terminated alkyl chain on the 5' end.

10. The method of claim 9, wherein the oligonucleotide is a DNA sequence.

11. The method of claim 8, wherein the second single stranded nucleic acid target sequence is DNA.

12. The method of claim 8, wherein the second single stranded nucleic acid target sequence is RNA.

13. The method of claim 8, wherein the electrode is gold.

14. The method of claim 8, wherein the electrode is carbon.

15. The method of claim 8, wherein a salt is added to the duplex nucleic acid, before the duplex nucleic acid is deposited onto the electrode.

16. The method of claim 15, wherein the salt is $MgCl_2$.

17. The method of claim 15, wherein the salt added has a concentration of greater than 10 mM.

18. The method of claim 17, wherein the salt has a concentration of 100 mM.

19. The method of claim 8, wherein the monolayer of first single stranded derivatized nucleic acid probe sequences is from about 35 pmol/cm$^2$ to about 60 pmol/cm$^2$.

20. The method of claim 19, wherein the monolayer of first single stranded derivatized nucleic acid probe sequences is about 50 pmol/cm$^2$.

21. The method of claim 8, wherein the monolayer of first single stranded derivatized nucleic acid probe sequences is from about 0.5 pmol/cm$^2$ to about 35 pmol/cm$^2$.

22. The method of claim 21, wherein the monolayer of first single stranded derivatized nucleic acid probe sequences is about 1 pmol/cm$^2$.

23. A method of detecting one or more single-base sequence lesions in a target nucleic acid sequence, comprising:
   a) contacting a first single stranded nucleic acid probe sequence with a second single stranded nucleic acid target sequence to form a duplex, wherein the second single stranded nucleic acid target sequence is hybridized to a monolayer of first single stranded nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety, wherein the intercalative, redox-active moiety is intercalatively stacked and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in the target sequence.

24. The method of claim 23, wherein the intercalative, redox-active moiety is methylene blue.

25. The method of claim 23, wherein the non-intercalative, redox-active moiety is ferricyanide.

26. The method of claim 23, wherein the second single stranded nucleic acid target sequence is DNA.

27. The method of claim 23, wherein the second single stranded nucleic acid target sequence is RNA.

28. The method of claim 23, wherein the intercalative, redox-active moiety is not covalently bound to the nucleic acid-modified film.

29. A method of detecting one or more single-base mismatches in a target nucleic acid sequence, comprising:
   a) contacting a first single stranded, derivatized nucleic acid probe sequence with a second single stranded nucleic acid target sequence to form a duplex, wherein the second single stranded nucleic acid target sequence is hybridized to a monolayer of first single stranded derivatized nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence mismatches is indicative of the presence or absence of one or more single-base sequence mismatches in the target sequence.

30. The method of claim 29, wherein the single-base mismatch is a guanine-adenine pairing.

31. The method of claim 29, wherein the single-base mismatch is an adenine—adenine pairing.

32. The method of claim 29, wherein the single base mismatch is a guanine—guanine pairing, a thymine—thymine pairing, a cytosine—cytosine pairing, a guanine-thymine pairing, a cytosine-thymine pairing, or a cytosine-adenine pairing.

33. The method of claim 29, wherein the first single stranded derivatized nucleic acid probe sequence is an oligonucleotide with a thiol-terminated alkyl chain on the 5' end.

34. The method of claim 29, wherein the second single stranded nucleic acid target sequence is DNA.

35. The method of claim 29, wherein the second single stranded nucleic acid target sequence is RNA.

36. A method of detecting one or more single-base sequence lesions in a portion of a gene sequence, wherein the one or more single-base sequence lesions is associated with a disease, comprising:
   a) contacting a first single stranded nucleic acid probe sequence, comprising a derivatized portion of the sequence of a gene, with a second single stranded nucleic acid target sequence comprising a wild type portion of the gene, to form a duplex, wherein the second single stranded nucleic acid target sequence is hybridized to a monolayer of first single stranded nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in the gene sequence wherein the base stacking perturbation or single-base sequence lesion is associated with a disease.

37. The method of claim 36, wherein the portion of the gene sequence is up to 200 nucleotides in length.

38. The method of claim 36, wherein the portion of the gene sequence is from 10 to 50 nucleotides in length.

39. The method of claim 38, wherein the portion of the gene sequence is from 15 to 35 nucleotides in length.

40. The method of claim 36, wherein the gene is a human p53 gene.

41. The method of claim 36, wherein the second single stranded nucleic acid target sequence is DNA.

42. The method of claim 36, wherein the second single stranded nucleic acid target sequence is RNA.

43. A method of detecting one or more naturally occurring DNA lesions in a target nucleic acid sequence, comprising:
   a) contacting a first single stranded nucleic acid probe sequence containing a DNA lesion with a second single stranded nucleic acid target sequence to form a duplex, wherein the second single stranded nucleic acid target sequence is hybridized to a monolayer of first single stranded nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more DNA lesions is indicative of the presence or absence of one or more DNA lesions in the target sequence.

44. The method of claim 43, wherein the DNA lesion is an oxidized nucleotide.

45. The method of claim 44, wherein the oxidized nucleotide is 8-oxo-adenine.

46. The method of claim 43, wherein the DNA lesion is a hydroxy pyrimidine.

47. The method of claim 46, wherein the hydroxy pyrimidine is 5,6-dihydro thymine.

48. The method of claim 43, wherein the DNA lesion is an abasic site.

49. The method of claim 43, wherein the DNA lesion is deamination of a nucleotide.

50. The method of claim 49, wherein the deaminated nucleotide is cytosine.

51. The method of claim 43, wherein the DNA lesion is deoxyuracil paired with guanine.

52. The method of claim 43, wherein the second single stranded nucleic acid target sequence is DNA.

53. The method of claim 43, wherein the second single stranded nucleic acid target sequence is RNA.

54. A method of detecting one or more single-base sequence lesions in a target nucleic acid sequence, comprising:
   a) contacting a first single stranded nucleic acid probe sequence with a second single stranded nucleic acid target sequence to form a duplex, wherein the second single stranded nucleic acid target sequence is hybridized to a monolayer of first single stranded nucleic acid probe sequences on an addressable multielectrode array, wherein the monolayer is prepared by first attaching a duplex comprising the first single stranded nucleic acid probe sequence to the addressable multielectrode array, and dehybridizing the duplex, such that the first single stranded nucleic acid probe sequence remains attached to the addressable multielectrode array, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in the target sequence.

55. The method of claim 54, wherein the multielectrode array comprises gold electrodes.

56. The method of claim 54, wherein the multielectrode array comprises carbon electrodes.

57. The method of claim 54, wherein the electrodes of the multielectrode array are 500 µm or less in diameter.

58. The method of claim 54, wherein the second single stranded nucleic acid target sequence is DNA.

59. The method of claim 54, wherein the second single stranded nucleic acid target sequence is RNA.

60. A method of detecting one or more single-base sequence lesions in a target nucleic acid sequence, comprising:
   a) contacting a first single stranded nucleic acid probe sequence with a second single stranded nucleic acid target sequence to form a duplex, wherein the second single stranded nucleic acid target sequence is hybridized to a monolayer of first single stranded nucleic acid probe sequences on an ultramicroelectrode, wherein the monolayer is prepared by first attaching a duplex comprising the first single stranded nucleic acid probe sequence to the ultramicroelectrode, and dehybridizing the duplex, such that the first single stranded nucleic acid probe sequence remains attached to the ultramicroelectrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in the target sequence.

61. The method of claim 60, wherein the second single stranded nucleic acid target sequence is DNA.

62. The method of claim 60, wherein the second single stranded nucleic acid target sequence is RNA.

63. A method of detecting one or more single-base sequence lesions in a hybrid of DNA and RNA, comprising:
   a) contacting a first single stranded nucleic acid probe sequence with a second single stranded nucleic acid target sequence to form a duplex, wherein the second single stranded nucleic acid target sequence is hybridized to a monolayer of first single stranded nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge to the electrical current or charge of a nucleic acid duplex not having one or more single-base sequence lesions is indicative of the presence or absence of the one or more single-base sequence lesions in a hybrid of DNA and RNA.

64. The method of claim 63, wherein the first single stranded nucleic acid probe sequence is DNA and the second single stranded nucleic acid target sequence is RNA.

65. The method of claim 64, wherein the RNA is mRNA.

66. The method of claim 64, wherein the DNA is cDNA.

67. A method of detecting one or more single-base sequence lesions in a portion of a derivatized wild type target nucleic acid sample, comprising:
   a) contacting a first single stranded nucleic acid probe sequence with a second single stranded nucleic acid target sequence, comprising a portion of a derivatized wild type target nucleic acid sample, to form a duplex, wherein the second single stranded nucleic acid target sequence is hybridized to a monolayer of first single stranded nucleic acid probe sequences on an electrode, wherein the monolayer is prepared by first attaching a duplex comprising the first single stranded nucleic acid probe sequence to the electrode, and dehybridizing the duplex, such that the first single stranded nucleic acid probe sequence remains attached to the electrode, and wherein the hybrid of the first single stranded nucleic acid probe sequence and the second single stranded target sequence form a double stranded nucleic acid-modified film;
   b) immersing the nucleic acid-modified film in a solution comprising an intercalative, redox-active moiety and a non-intercalative redox-active moiety; and
   c) measuring the electrical current or charges of the catalytic reduction of the non-intercalative, redox-active species by the intercalative, redox-active moiety wherein a difference of the electric current or charge relative to the electrical current or charge of a nucleic acid duplex not having one or more single-base sequence lesions is indicative of the presence or absence of one or more single-base sequence lesions in a portion of the derivatized wild type target nucleic acid sample.

68. The method of claim 67, wherein the second single stranded nucleic acid target sequence is DNA.

69. The method of claim 67, wherein the second single stranded nucleic acid target sequence is RNA.

* * * * *

UNITED STATES PATENT AND TRADEMARK OFFICE
CERTIFICATE OF CORRECTION

PATENT NO. : 6,649,350 B2
DATED : November 18, 2003
INVENTOR(S) : Jacqueline K. Barton et al.

It is certified that error appears in the above-identified patent and that said Letters Patent is hereby corrected as shown below:

<u>Column 43, line 55 through Column 55, line 20,</u>
Please replace the sequence listing with the attached substitute sequence listing:

Signed and Sealed this

Second Day of November, 2004

JON W. DUDAS
*Director of the United States Patent and Trademark Office*

```
<210>  1
<211>  15
<212>  DNA
<213>  Artificial Sequence

<220>
<223>  Oligonucleotide probe

<400>  1
atggatctca tctac                                                    15

<210>  2
<211>  15
<212>  DNA
<213>  Artificial Sequence

<220>
<223>  Oligonucleotide probe

<400>  2
atcctactca tggac                                                    15

<210>  3
<211>  14
<212>  DNA
<213>  Artificial Sequence

<220>
<223>  Oligonucleotide probe

<400>  3
attatataat tgct                                                     14

<210>  4
<211>  15

<212>  DNA
<213>  Artificial Sequence

<220>
<223>  Oligonucleotide probe

<400>  4
agtacagtca tcgcg                                                    15
```

```
<210>  5
<211>  15
<212>  DNA
<213>  Artificial Sequence

<220>
<223>  Oligonucleotide probe

<400>  5
cgcgatgact gtact                                                    15

<210>  6
<211>  15
<212>  DNA
<213>  Artificial Sequence

<220>
<223>  Oligonucleotide probe

<400>  6
cgcgacgact gtact                                                    15

<210>  7
<211>  15
<212>  DNA
<213>  Artificial Sequence

<220>
<223>  Oligonucleotide probe

<400>  7
cgcgatgtct gtact                                                    15

<210>  8
<211>  15
<212>  DNA
<213>  Artificial Sequence

<220>
<223>  Oligonucleotide probe

<400>  8
cgcgatcact gtact                                                    15

<210>  9
<211>  15
<212>  DNA
```

```
<213>   Artificial Sequence

<220>
<223>   Oligonucleotide probe

<400>   9
cgcgatggct gtact                                                    15

<210>   10
<211>   15
<212>   DNA
<213>   Artificial Sequence

<220>
<223>   Oligonucleotide probe

<400>   10
cgcgatgaat gtact                                                    15

<210>   11
<211>   15
<212>   DNA
<213>   Artificial Sequence

<220>
<223>   Oligonucleotide probe

<400>   11
cgcgatgcct gtact                                                    15

<210>   12
<211>   15
<212>   DNA
<213>   Artificial Sequence

<220>
<223>   Oligonucleotide probe

<400>   12
atataatata tggat                                                    15

<210>   13
<211>   15
<212>   DNA
<213>   Artificial Sequence

<220>
<223>   Oligonucleotide probe

<400>   13
agtacagtca tcgcg                                                    15

<210>   14
<211>   15
<212>   DNA
<213>   Artificial Sequence
```

```
<220>
<223>   Oligonucleotide probe

<400>   14
ggcgcccggc gccgg                                                        15

<210>   15
<211>   15
<212>   DNA
<213>   Artificial sequence

<220>
<223>   Oligonucleotide probe

<400>   15
atgggcctcc ggttc                                                        15

<210>   16
<211>   17
<212>   DNA
<213>   Artificial sequence

<220>
<223>   Oligonucleotide probe

<220>
<221>   misc_feature
<222>   (1)..(17)
<223>   n is inosine (I)

<400>   16
ananatncnc anatcct                                                      17

<210>   17
<211>   15
<212>   DNA
<213>   Artificial sequence

<220>
<223>   Oligonucleotide probe

<220>
<221>   misc_feature
<222>   (1)..(15)
<223>   n is inosine (I)

<400>   17
anctnaatca ntcct                                                        15

<210>   18
<211>   16
<212>   DNA
<213>   Artificial sequence

<220>
<223>   Oligonucleotide probe
```

```
<220>
<221>  misc_feature
<222>  (1)..(16)
<223>  n is inosine (I)

<400>  18
nanatataaa ncacct                                                        16

<210>  19
<211>  16
<212>  DNA
<213>  Artificial sequence

<220>
<223>  Oligonucleotide probe

<220>
<221>  misc_feature
<222>  (1)..(16)
<223>  n is inosine (I)

<220>
<221>  misc_feature
<222>  (8)..(8)
<223>  n is Methylated cytosine

<400>  19
tcttcanntn anacct                                                        16

<210>  20
<211>  16
<212>  DNA
<213>  Artificial sequence

<220>
<223>  Oligonucleotide probe

<220>
<221>  misc_feature

<222>  (1)..(16)
<223>  n is inosine (I)

<400>  20
tcttcanctn anacct                                                        16

<210>  21
<211>  15
<212>  DNA
<213>  Artificial Sequence

<220>
<223>  Complement of SEQ ID NO:1

<220>
<221>  misc_feature
<222>  (1)..(15)
```

```
<223>   n is inosine (I)

<400>   21
ntanatnana tccat                                                    15

<210>   22
<211>   15
<212>   DNA
<213>   Artificial Sequence

<220>
<223>   Complement of SEQ ID NO:2

<220>
<221>   misc_feature
<222>   (1)..(15)
<223>   n is inosine (I)

<400>   22
ntccatnant annat                                                    15

<210>   23
<211>   17
<212>   DNA
<213>   Artificial sequence

<220>
<223>   Complement of SEQ ID NO:16

<220>
<221>   misc_feature
<222>   (1)..(17)
<223>   n is inosine (I)

<400>   23
aggatctncn catctct                                                  17

<210>   24
<211>   16
<212>   DNA
<213>   Artificial sequence

<220>
<223>   Oligonucloetide probe

<220>
<221>   misc_feature
<222>   (9)..(9)
<223>   n is inosine (I)

<400>   24
aggatctncc atctct                                                   16

<210>   25
<211>   15
<212>   DNA
<213>   Artificial sequence
```

```
<220>
<223>  Complement of SEQ ID NO:17

<220>
<221>  misc_feature
<222>  (1)..(15)
<223>  n is inosine (I)

<400>  25
aggactnaut canct                                                    15

<210>  26
<211>  16
<212>  DNA
<213>  Artificial sequence

<220>
<223>  Complement of SEQ ID NO:18

<220>
<221>  misc_feature
<222>  (1)..(16)
<223>  n is inosine (I)

<400>  26
aggtncttta tatctc                                                   16

<210>  27
<211>  16
<212>  DNA
<213>  Artificial sequence

<220>
<223>  Oligonucleotide probe

<220>
<221>  misc_feature
<222>  (1)..(16)
<223>  n is inosine (I)

<220>
<221>  misc_feature
<222>  (10)..(10)
<223>  n is Methylated cytosine

<400>  27
aggtctcann tnaana                                                   16

<210>  28
<211>  16
<212>  DNA
<213>  Artificial sequence

<220>
<223>  Complement of SEQ ID NO:20

<220>
```

```
<221>  misc_feature
<222>  (1)..(16)
<223>  n is inosine (I)

<400>  28
aggtctcanc tnaana                                                    16

<210>  29
<211>  15
<212>  DNA
<213>  Artificial sequence

<220>
<223>  Complement of SEQ ID NO:12

<400>  29
atccatatay tatat                                                     15

<210>  30
<211>  15
<212>  DNA
<213>  Artificial sequence

<220>
<223>  Complement of SEQ ID NO:4

<400>  30
cgcgaygact gtact                                                     15

<210>  31
<211>  15
<212>  DNA
<213>  Artificial sequence

<220>
<223>  Complement of SEQ ID NO:14

<400>  31
ccggcgccgg rcgcc                                                     15
```